(12) United States Patent
Kshirsagar et al.

(10) Patent No.: US 8,088,788 B2
(45) Date of Patent: Jan. 3, 2012

(54) SUBSTITUTED FUSED[1,2] IMIDAZO[4,5-C] RING COMPOUNDS AND METHODS

(75) Inventors: Tushar A. Kshirsagar, Saint Paul, MN (US); Karl J. Manske, Saint Paul, MN (US); Larry R. Krepski, Saint Paul, MN (US); Joan T. Moseman, Saint Paul, MN (US); George W. Griesgraber, Saint Paul, MN (US); Sarah Johannessen Slania, Saint Paul, MN (US); Scott E. Langer, Saint Paul, MN (US); Philip D. Heppner, Saint Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 653 days.

(21) Appl. No.: 12/281,728

(22) PCT Filed: Mar. 14, 2007

(86) PCT No.: PCT/US2007/063972
§ 371 (c)(1),
(2), (4) Date: Jan. 6, 2009

(87) PCT Pub. No.: WO2007/106852
PCT Pub. Date: Sep. 20, 2007

(65) Prior Publication Data
US 2009/0221551 A1    Sep. 3, 2009

Related U.S. Application Data

(60) Provisional application No. 60/743,491, filed on Mar. 15, 2006, provisional application No. 60/807,156, filed on Jul. 12, 2006.

(51) Int. Cl.
*A61K 31/4745*   (2006.01)
*C07D 471/14*   (2006.01)

(52) U.S. Cl. ............ 514/287; 546/64; 544/63; 544/89; 544/233; 544/247; 540/546; 514/211; 514/229.5; 514/248; 514/257

(58) Field of Classification Search .................. 514/287, 514/211, 229.5, 248, 257; 546/64; 544/63, 544/89, 233, 247; 540/546
See application file for complete search history.

(56) References Cited

U.S. PATENT DOCUMENTS

| | | | |
|---|---|---|---|
| 4,689,338 A | 8/1987 | Gerster | 514/293 |
| 5,175,296 A | 12/1992 | Gerster | 546/82 |
| 5,352,784 A | 10/1994 | Nikolaides et al. | 544/126 |
| 5,367,076 A | 11/1994 | Gerster | 546/82 |
| 5,389,640 A | 2/1995 | Gerster et al. | 514/293 |
| 5,482,936 A * | 1/1996 | Lindstrom | 514/183 |
| 6,194,425 B1 | 2/2001 | Gerster et al. | 514/293 |
| 6,245,776 B1 | 6/2001 | Skwierczynski et al. | 514/293 |
| 6,525,064 B1 | 2/2003 | Dellaria et al. | 514/303 |
| 7,091,214 B2 | 8/2006 | Hays et al. | 514/292 |
| 2003/0139364 A1 | 7/2003 | Krieg et al. | 435/345 |
| 2003/0185835 A1 | 10/2003 | Braun | 424/404 |
| 2004/0076633 A1 | 4/2004 | Thomsen et al. | 514/44 |
| 2004/0176367 A1 | 9/2004 | Griesgraber et al. | 514/227.8 |
| 2004/0258698 A1 | 12/2004 | Wightman et al. | 514/291 |
| 2004/0265351 A1 | 12/2004 | Miller et al. | 514/183 |
| 2005/0009858 A1 | 1/2005 | Martinez-Colon et al. | 514/292 |
| 2006/0111387 A1 | 5/2006 | Hays et al. | 514/292 |
| 2007/0060754 A1 | 3/2007 | Lindstrom et al. | 546/82 |
| 2007/0213356 A1 | 9/2007 | Merrill et al. | 514/293 |
| 2007/0219228 A1 | 9/2007 | Niwas et al. | 514/292 |
| 2008/0085895 A1 | 4/2008 | Griesgraber et al. | 514/233.2 |
| 2008/0188469 A1 | 8/2008 | Thomsen et al. | 514/229.8 |
| 2008/0269192 A1 | 10/2008 | Griesgraber et al. | 514/211.09 |

FOREIGN PATENT DOCUMENTS

| | | |
|---|---|---|
| WO | WO0236592 | 5/2002 |
| WO | WO2005020999 | 3/2005 |
| WO | WO2006026760 | 3/2006 |
| WO | WO2006091394 | 8/2006 |

OTHER PUBLICATIONS

Higuchi, T., et al., "Pro-drugs as Novel Delivery Systems", 1975, A.C.S. Symposium Series, vol. 14, pp. 14-15.
Bundgaard, H., "Bioreversible Carriers in Drug Design", 1987, American Pharmaceutical Association, In: E.B. Roche (Ed.), Theory and Application, Pergamon Press, New York, p. 13.
Lebreton, L., et al., "Structure-Immunosuppressive Activity Relationships of New Analogues of 15-Deoxyspergualin.2.Structural Modifications of the Spermidine Moiety", Journal of Medicinal Chemistry, 1999, p. 4749-4763, vol. 42, No. 23.
Testerman, et al., "Cytokine Induction by Immunomodulators Imiquimod and S-27609", Journal of Leukocyte Biology, Sep. 1995, pp. 365-372, vol. 58.

* cited by examiner

*Primary Examiner* — Charanjit Aulakh

(57) ABSTRACT

[1,2]Imidazo[4,5-c] ring compounds (e.g., imidazo[4,5-c]quinolines, imidazo[4,5-c]naphthyridines, and imidazo[4,5-c]pyridines) substituted with a fused ring containing an oxygen and/or nitrogen atom attached at the 1- and/or 2-position, pharmaceutical compositions containing the compounds, intermediates, methods of making the compounds, and methods of use of these compounds as immunomodulators, for inducing cytokine biosynthesis in animals and in the treatment of diseases including viral and neoplastic diseases, are disclosed.

19 Claims, No Drawings

SUBSTITUTED FUSED[1,2] IMIDAZO[4,5-C] RING COMPOUNDS AND METHODS

CROSS REFERENCE TO RELATED APPLICATIONS

The present invention claims priority to U.S. Provisional Application Ser. No. 60/743,491, filed Mar. 15, 2006, and to U.S. Provisional Application Ser. No. 60/807,156, filed Jul. 12, 2006, both of which are incorporated herein by reference.

BACKGROUND

Certain compounds have been found to be useful as immune response modifiers (IRMs), rendering them useful in the treatment of a variety of disorders. However, there continues to be interest in and a need for compounds that have the ability to modulate the immune response, by induction of cytokine biosynthesis or other means.

SUMMARY

It has now been found that certain [1,2]imidazo[4,5-c] ring compounds substituted with a fused ring containing an oxygen and/or nitrogen atom attached at the 1- and/or 2-position are useful in modulating cytokine biosynthesis in animals. The present invention, therefore, provides such compounds, which are of the following Formula I:

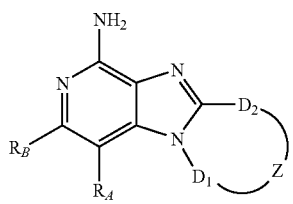

I wherein $D_1$, $D_2$, Z, $R_A$, and $R_B$ are as defined below.

The compounds of Formula I are useful, for example, as immune response modifiers (IRMs) due to their ability to modulate cytokine biosynthesis (e.g., induce the biosynthesis or production of one or more cytokines) and otherwise modulate the immune response when administered to animals. The ability to modulate cytokine biosynthesis, for example, induce the biosynthesis of one or more cytokines, makes the compounds useful in the treatment of a variety of conditions such as viral diseases and neoplastic diseases, that are responsive to such changes in the immune response.

The invention further provides pharmaceutical compositions containing an effective amount of a compound of Formula I and methods of inducing cytokine biosynthesis in an animal, treating a viral infection and/or treating a neoplastic disease in an animal by administering an effective amount of a compound of Formula I to the animal.

In addition, methods of synthesizing compounds of Formula I and intermediates useful in the synthesis of these compounds are provided.

As used herein, "a", "an", "the", "at least one", and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formula I:

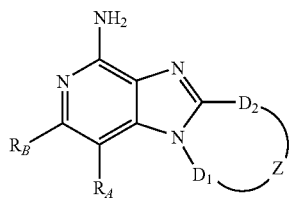

I and, more particularly, compounds of the following Formulas II, III, IV, and V:

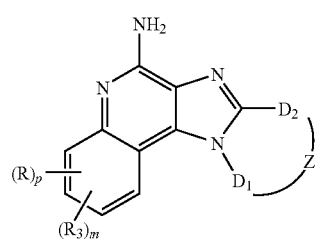

II

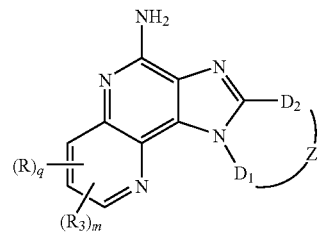

III

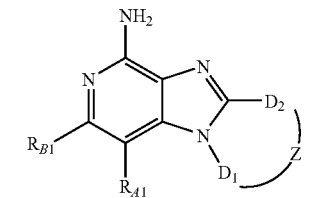

IV

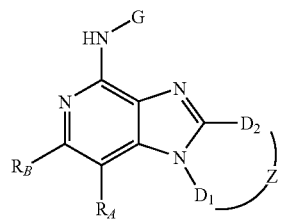

V wherein $D_1$, $D_2$, G, Z, R, $R_3$, $R_A$, $R_B$, $R_{A1}$, $R_{B1}$, m, p, and q are as defined below; and pharmaceutically acceptable salts thereof.

In one embodiment, the present invention provides a compound of Formula I:

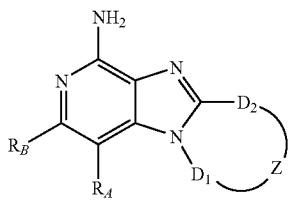

I wherein:

$D_1$ is selected from the group consisting of —O—, —N(-$Q_1$-$R_4$)—, and —CH($R_1$)—;

$D_2$ is selected from the group consisting of —O—, —N(-$Q_2$-$R_4$)—, and —CH$_2$—;

with the proviso that when $D_1$ is —CH($R_1$)— then $D_2$ is —O— or —N(-$Q_2$-$R_4$)—;

Z is selected from the group consisting of —(CH$_2$)$_n$— and —(CH$_2$)$_c$—C($R_{2a}$)($R_2$)—(CH$_2$)$_d$—;

or -$D_1$-Z-$D_2$-, together with the imidazo ring atoms to which $D_1$ and $D_2$ are attached, forms a fused ring selected from the group consisting of

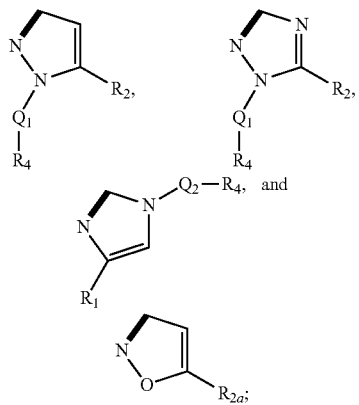

wherein the highlighted bond indicates the position where the ring is fused;

$R_1$ is selected from the group consisting of:
—$X_1$—$R_4$,
—$X_1$—Y—$R_4$,
—$X_1$—Y—X"—Y—$R_4$, and
—$X_1$—$R_5$;

$R_{2a}$ is selected from the group consisting of hydrogen and $C_{1-4}$ alkyl optionally substituted by hydroxy or halogen;

$R_2$ is selected from the group consisting of hydrogen, hydroxy, $C_{1-4}$ alkoxy, and $C_{1-4}$ alkyl optionally substituted by hydroxy or halogen;

c and d are independently 0, 1, or 2 with the proviso that c+d is ≦2;

with the proviso that when c and/or d is 0 then $R_2$ is other than hydroxy or $C_{1-4}$ alkoxy;

n is 1, 2, or 3;

$R_A$ and $R_B$ are each independently selected from the group consisting of:
hydrogen,
halogen,
alkyl,
alkenyl,
alkoxy,
alkylthio, and
—N($R_9$)$_2$;

or when taken together, $R_A$ and $R_B$ form a fused aryl or heteroaryl ring containing one heteroatom selected from the group consisting of N and S, wherein the fused aryl or heteroaryl ring is unsubstituted or substituted by one or more R groups, or substituted by one $R_3$ group, or substituted by one $R_3$ group and one R group;

or when taken together, $R_A$ and $R_B$ form a fused 5 to 7 membered saturated ring, optionally containing one heteroatom selected from the group consisting of N and S, and unsubstituted or substituted by one or more R groups;

R is selected from the group consisting of:
halogen,
hydroxy,
alkyl,
alkenyl,
haloalkyl,
alkoxy,
alkylthio, and
—N($R_9$)$_2$;

$R_3$ is selected from the group consisting of:
—Z'—$R_4$,
—Z'—X"—$R_4$,
—Z'—X"—Y—$R_4$,
—Z'—X"—Y—X"—Y—$R_4$, and
—Z'—X"—$R_5$;

$X_1$ is selected from the group consisting of alkylene, alkenylene, and alkynylene, wherein the alkylene, alkenylene, and alkynylene are optionally interrupted by one or more —O— groups, and optionally substituted by a hydroxy or methoxy group;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,
—C(=N—O—$R_8$)—,
—CH(—N(—O—$R_8$)-Q-$R_4$)—,

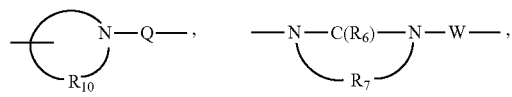

-continued

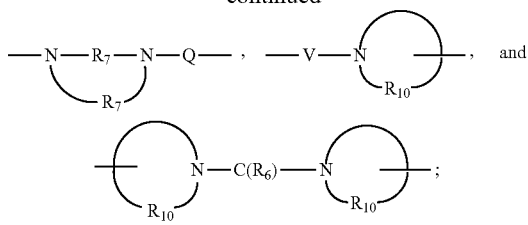

Z' is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo; with the proviso that when $R_4$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_4$ is heterocyclyl, then the one or more substituents may also be independently selected from the group consisting of arylalkylenyl, and aminocarbonyl;

$R_5$ is selected from the group consisting of:

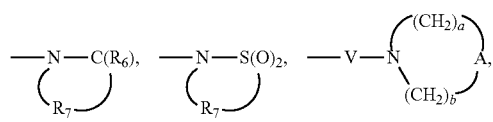

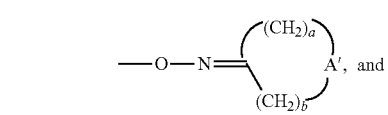

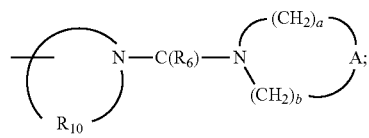

$R_6$ is selected from the group consisting of $=O$ and $=S$;
$R_7$ is $C_{2-7}$ alkylene;
$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;

$R_9$ is selected from the group consisting of hydrogen and alkyl;

$R_{10}$ is $C_{3-8}$ alkylene;

A is selected from the group consisting of —$CH_2$—, —O—, —C(O)—, —$S(O)_{0-2}$—, and —N(-Q-$R_4$)—;

A' is selected from the group consisting of —O—, —$S(O)_{0-2}$—, —N(-Q-$R_4$)—, and —$CH_2$—;

Q, $Q_1$, and $Q_2$ are each independently selected from the group consisting of a bond, —$C(R_6)$—, —$C(R_6)$—$C(R_6)$—, —$S(O)_2$—, —$C(R_6)$—N($R_8$)—W—, —$S(O)_2$—N($R_8$)—, —$C(R_6)$—O—, —$C(R_6)$—S—, and —$C(R_6)$—N($OR_9$)—;

with the proviso that when $Q_2$ is a bond then $R_4$ is hydrogen, $C_{1-3}$ alkyl, or pyridin-3-ylmethyl;

V is selected from the group consisting of —$C(R_6)$—, —O—$C(R_6)$—, —N($R_8$)—$C(R_6)$—, and —$S(O)_2$—;

W is selected from the group consisting of a bond, —C(O)—, and —$S(O)_2$—; and a and b are independently integers from 1 to 6 with the proviso that a+b is ≦7;

with the proviso that $X_1$ can also be a bond when:

$R_4$ is bonded to $X_1$; or

Y is bonded to $X_1$ and Y is —$C(R_6)$—, —$C(R_6)$—O—, —$C(R_6)$—N($R_8$)—, —$C(R_6)$—N($OR_9$)—, —C(=N—O—$R_8$)—, —CH(—N(—O—$R_8$)-Q-$R_4$)—, wherein V is —$C(R_6)$—, or $R_5$ is bonded to $X_1$ and $R_5$ is wherein V is —$C(R_6)$— or or a pharmaceutically acceptable salt thereof.

In another embodiment, there is provided a compound of Formula II:

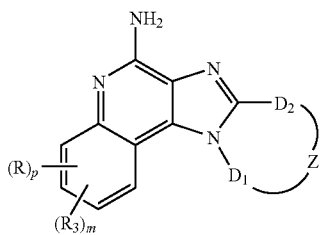

wherein:

$D_1$ is selected from the group consisting of —O—, —N(-$Q_1$-$R_4$)—, and —CH($R_1$)—;

$D_2$ is selected from the group consisting of —O—, —N(-$Q_2$-$R_4$)—, and —CH$_2$—;

with the proviso that when $D_1$ is —CH($R_1$)— then $D_2$ is —O— or —N(-$Q_2$-$R_4$)—;

Z is selected from the group consisting of —(CH$_2$)$_n$— and —(CH$_2$)$_c$—C($R_{2a}$)($R_2$)—(CH$_2$)$_d$—;

or -$D_1$-Z-$D_2$-, together with the imidazo ring atoms to which $D_1$ and $D_2$ are attached, forms a fused ring selected from the group consisting of

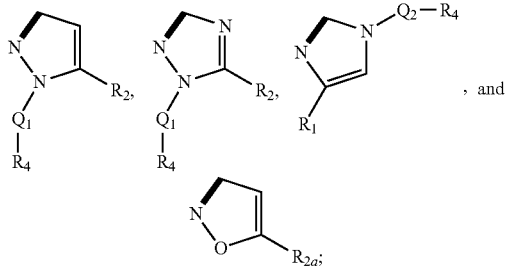

wherein the highlighted bond indicates the position where the ring is fused;

$R_1$ is selected from the group consisting of:
—$X_1$—$R_4$,
—$X_1$—Y—$R_4$,
—$X_1$—Y—X"—Y—$R_4$, and
—$X_1$—$R_5$;

$R_{2a}$ is selected from the group consisting of hydrogen and $C_{1-4}$ alkyl optionally substituted by hydroxy or halogen;

$R_2$ is selected from the group consisting of hydrogen, hydroxy, $C_{1-4}$ alkoxy, and $C_{1-4}$ alkyl optionally substituted by hydroxy or halogen;

c and d are independently 0, 1, or 2 with the proviso that c+d is $\leq 2$;

with the proviso that when c and/or d is 0 then $R_2$ is other than hydroxy or $C_{1-4}$ alkoxy;

n is 1, 2, or 3;

R is selected from the group consisting of:
halogen,
hydroxy,
alkyl,
alkenyl,
haloalkyl,
alkoxy,
alkylthio, and
—N($R_9$)$_2$;

p is an integer from 0 to 4;

$R_3$ is selected from the group consisting of:
—Z'—$R_4$,
—Z'—X"—Y—$R_4$,
—Z'—X"—Y—X"—Y—$R_4$, and
—Z'—X"—$R_5$;

m is 0 or 1; with the proviso that when m is 1, then p is 0 or 1;

$X_1$ is selected from the group consisting of alkylene, alkenylene, and alkynylene, wherein the alkylene, alkenylene, and alkynylene are optionally interrupted by one or more —O— groups, and optionally substituted by a hydroxy or methoxy group;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_9$)—,
—C($R_6$)—N(O$R_9$)—,
—O—N($R_8$)-Q-,
—O—N=C($R_4$)—,
—C(=N—O—$R_8$)—,
—CH(—N(—O—$R_8$)-Q-$R_4$)—,

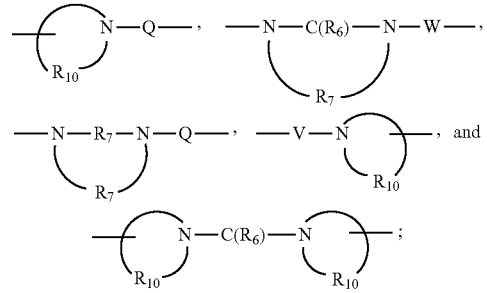

Z' is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo; with the proviso that when $R_4$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_4$ is heterocyclyl, then the one or more substituents may also be independently selected from the group consisting of arylalkylenyl, and aminocarbonyl;

$R_5$ is selected from the group consisting of:

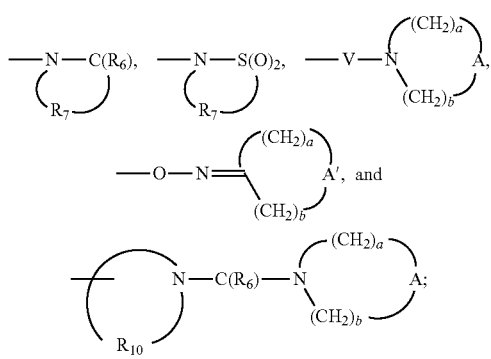

$R_6$ is selected from the group consisting of =O and =S;
$R_7$ is $C_{2-7}$ alkylene;
$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;
$R_9$ is selected from the group consisting of hydrogen and alkyl;
$R_{10}$ is $C_{3-8}$ alkylene;
A is selected from the group consisting of —$CH_2$—, —O—, —C(O)—, —S(O)$_{0-2}$—, and —N(-Q-$R_4$)—;
A' is selected from the group consisting of —O—, —S(O)$_{0-2}$—, —N(-Q-$R_4$)—, and —$CH_2$—;
Q, $Q_1$, and $Q_2$ are each independently selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—; with the proviso that when $Q_2$ is a bond then $R_4$ is hydrogen, $C_{1-3}$ alkyl, or pyridin-3-ylmethyl;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—; and
a and b are independently integers from 1 to 6 with the proviso that a+b is ≦7;
with the proviso that $X_1$ can also be a bond when:
$R_4$ is bonded to $X_1$; or
Y is bonded to $X_1$ and Y is —C($R_6$)—, —C($R_6$)—O—, —C($R_6$)—N($R_8$)—, —C($R_6$)—N(O$R_9$)—, —C(=N—O—$R_8$)—, —CH(—N(—O—$R_8$)-Q-$R_4$)—,

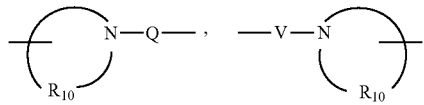

wherein V is —C($R_6$)—, or

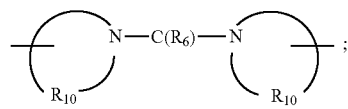

or
$R_5$ is bonded to $X_1$ and $R_5$ is

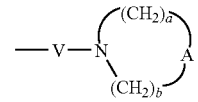

wherein V is —C($R_6$)— or

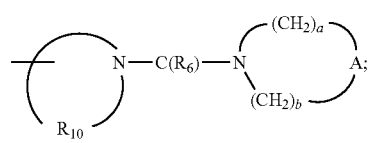

or a pharmaceutically acceptable salt thereof.

In another embodiment, there is provided a compound of Formula III:

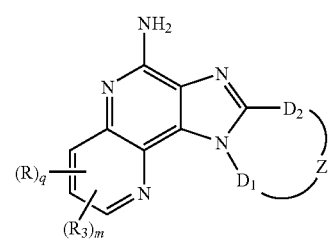

wherein:
$D_1$ is selected from the group consisting of —O—, —N(-$Q_1$-$R_4$)—, and —CH($R_1$)—;
$D_2$ is selected from the group consisting of —O—, —N(-$Q_2$-$R_4$)—, and —$CH_2$—;
with the proviso that when $D_1$ is —CH($R_1$)— then $D_2$ is —O— or —N(-$Q_2$-$R_4$)—;
Z is selected from the group consisting of —(CH$_2$)$_n$— and —(CH$_2$)$_c$—C($R_{2a}$)($R_2$)—(CH$_2$)$_d$—;
or -$D_1$-Z-$D_2$-, together with the imidazo ring atoms to which $D_1$ and $D_2$ are attached, forms a fused ring selected from the group consisting of

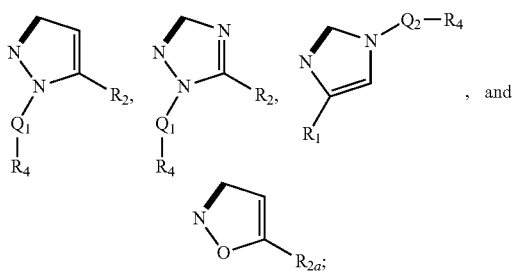

wherein the highlighted bond indicates the position where the ring is fused;

$R_1$ is selected from the group consisting of:
—$X_1$—$R_4$,
—$X_1$—Y—$R_4$,
—$X_1$—Y—X"—Y—$R_4$, and
—$X_1$—$R_5$;

$R_{2a}$ is selected from the group consisting of hydrogen and $C_{1-4}$ alkyl optionally substituted by hydroxy or halogen;

$R_2$ is selected from the group consisting of hydrogen, hydroxy, $C_{1-4}$ alkoxy, and $C_{1-4}$ alkyl optionally substituted by hydroxy or halogen;

c and d are independently 0, 1, or 2 with the proviso that c+d is $\leq 2$;

with the proviso that when c and/or d is 0 then $R_2$ is other than hydroxy or $C_{1-4}$ alkoxy;

n is 1, 2, or 3;

R is selected from the group consisting of:
halogen,
hydroxy,
alkyl,
alkenyl,
haloalkyl,
alkoxy,
alkylthio, and
—N($R_9$)$_2$;

q is an integer from 0 to 3;

$R_3$ is selected from the group consisting of:
—Z'—$R_4$,
—Z'—X"—$R_4$,
—Z'—X"—Y—$R_4$,
—Z'—X"—Y—X"—Y—$R_4$, and
—Z'—X"—$R_5$;

m is 0 or 1; with the proviso that when m is 1, then q is 0 or 1;

$X_1$ is selected from the group consisting of alkylene, alkenylene, and alkynylene, wherein the alkylene, alkenylene, and alkynylene are optionally interrupted by one or more —O— groups, and optionally substituted by a hydroxy or methoxy group;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,
—C(=N—O—$R_8$)—,
—CH(—N(—O—$R_8$)-Q-$R_4$)—,

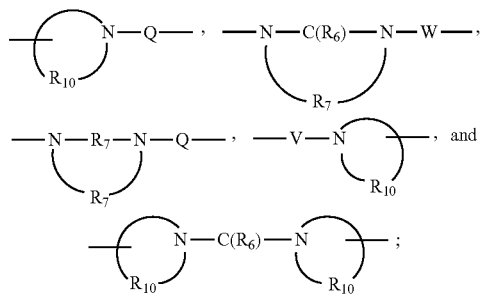

Z' is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo; with the proviso that when $R_4$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_4$ is heterocyclyl, then the one or more substituents may also be independently selected from the group consisting of arylalkylenyl, and aminocarbonyl;

$R_5$ is selected from the group consisting of:

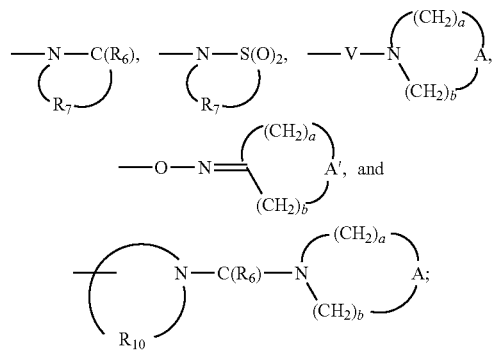

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;

$R_9$ is selected from the group consisting of hydrogen and alkyl;

$R_{10}$ is $C_{3-8}$ alkylene;

A is selected from the group consisting of —$CH_2$—, —O—, —C(O)—, —$S(O)_{0-2}$—, and —N(-Q-$R_4$)—;

A' is selected from the group consisting of —O—, —$S(O)_{0-2}$—, —N(-Q-$R_4$)—, and —$CH_2$—;

Q, $Q_1$, and $Q_2$ are each independently selected from the group consisting of a bond, —C($R_6$)—, —C($R_6$)—C($R_6$)—, —$S(O)_2$—, —C($R_6$)—N($R_8$)—W—, —$S(O)_2$—N($R_8$)—, —C($R_6$)—O—, —C($R_6$)—S—, and —C($R_6$)—N(O$R_9$)—; with the proviso that when $Q_2$ is a bond then $R_4$ is hydrogen, $C_{1-3}$ alkyl, or pyridin-3-ylmethyl;

V is selected from the group consisting of —C($R_6$)—, —O—C($R_6$)—, —N($R_8$)—C($R_6$)—, and —$S(O)_2$—;

W is selected from the group consisting of a bond, —C(O)—, and —$S(O)_2$—; and a and b are independently integers from 1 to 6 with the proviso that a+b is ≦7;

with the proviso that $X_1$ can also be a bond when:
$R_4$ is bonded to $X_1$; or
Y is bonded to $X_1$ and Y is —C($R_6$)—, —C($R_6$)—O—, —C($R_6$)—N($R_8$)—, —C($R_6$)—N(O$R_9$)—, —C(=N—O—$R_8$)—, —CH(—N(—O—$R_8$)-Q-$R_4$)—,

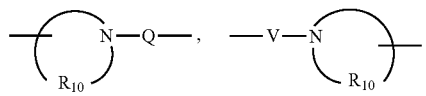

wherein V is —C($R_6$)—, or

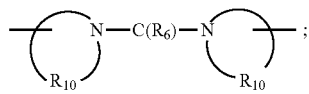

or
$R_5$ is bonded to $X_1$ and $R_5$ is

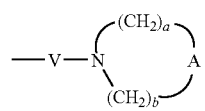

wherein V is —C($R_6$)— or

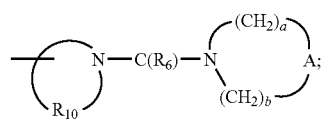

or a pharmaceutically acceptable salt thereof.

In another embodiment, there is provided a compound of Formula IV:

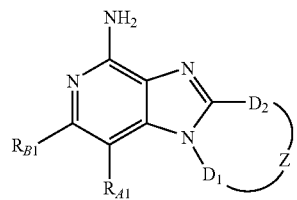

IV wherein:
$D_1$ is selected from the group consisting of —O—, —N(-$Q_1$-$R_4$)—, and —CH($R_1$)—;
$D_2$ is selected from the group consisting of —O—, —N(-$Q_2$-$R_4$)—, and —$CH_2$—;
with the proviso that when $D_1$ is —CH($R_1$)— then $D_2$ is —O— or —N(-$Q_2$-$R_4$)—;
Z is selected from the group consisting of —$(CH_2)_n$— and —$(CH_2)_c$—C($R_{2a}$)($R_2$)—$(CH_2)_d$—;
or -$D_1$-Z-$D_2$-, together with the imidazo ring atoms to which $D_1$ and $D_2$ are attached, forms a fused ring selected from the group consisting of

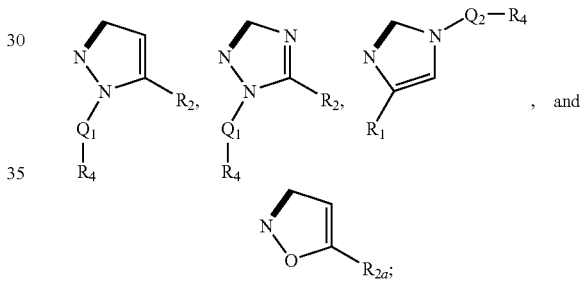

wherein the highlighted bond indicates the position where the ring is fused;

$R_1$ is selected from the group consisting of:
—$X_1$—$R_4$,
—$X_1$—Y—$R_4$,
—$X_1$—Y—X"—Y—$R_4$, and
—$X_1$—$R_5$;

$R_{2a}$ is selected from the group consisting of hydrogen and $C_{1-4}$ alkyl optionally substituted by hydroxy or halogen;

$R_2$ is selected from the group consisting of hydrogen, hydroxy, $C_{1-4}$ alkoxy, and $C_{1-4}$ alkyl optionally substituted by hydroxy or halogen;

c and d are independently 0, 1, or 2 with the proviso that c+d is ≦2;

with the proviso that when c and/or d is 0 then $R_2$ is other than hydroxy or $C_{1-4}$ alkoxy;

n is 1, 2, or 3;

$R_{A1}$ and $R_{B1}$ are each independently selected from the group consisting of:
hydrogen,
halogen,
alkyl,
alkenyl,
alkoxy,
alkylthio, and
—N($R_9$)$_2$;

R is selected from the group consisting of:
halogen,
hydroxy,
alkyl,
alkenyl,
haloalkyl,
alkoxy,
alkylthio, and
—N($R_9$)$_2$;

$X_1$ is selected from the group consisting of alkylene, alkenylene, and alkynylene, wherein the alkylene, alkenylene, and alkynylene are optionally interrupted by one or more —O— groups, and optionally substituted by a hydroxy or methoxy group;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,
—C(=N—O—$R_8$)—,
—CH(—N(—O—$R_8$)-Q-$R_4$)—,

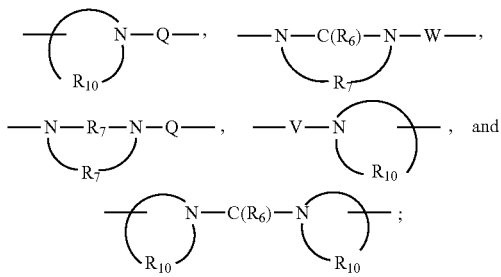

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo; with the proviso that when $R_4$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_4$ is heterocyclyl, then the one or more substituents may also be independently selected from the group consisting of arylalkylenyl, and aminocarbonyl;

$R_5$ is selected from the group consisting of:

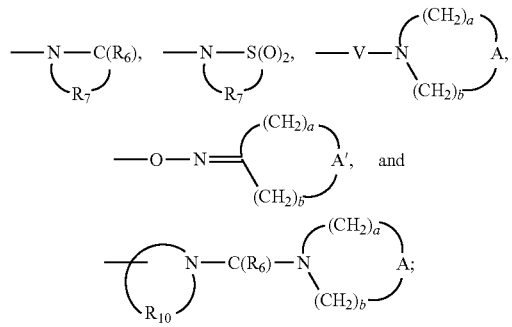

$R_6$ is selected from the group consisting of =O and =S;
$R_7$ is $C_{2-7}$ alkylene;
$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;
$R_9$ is selected from the group consisting of hydrogen and alkyl;
$R_{10}$ is $C_{3-8}$ alkylene;

A is selected from the group consisting of —CH$_2$—, —O—, —C(O)—, —S(O)$_{0-2}$—, and —N(-Q-$R_4$)—;
A' is selected from the group consisting of —O—, —S(O)$_{0-2}$—, —N(-Q-$R_4$)—, and —CH$_2$—;

Q, $Q_1$, and $Q_2$ are each independently selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—;
with the proviso that when $Q_2$ is a bond then $R_4$ is hydrogen, $C_{1-3}$ alkyl, or pyridin-3-ylmethyl;

V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—; and
a and b are independently integers from 1 to 6 with the proviso that a+b is ≦7;

with the proviso that $X_1$ can also be a bond when:
$R_4$ is bonded to $X_1$; or
Y is bonded to $X_1$ and Y is —C($R_6$)—, —C($R_6$)—O—, —C($R_6$)—N($R_8$)—, —C($R_6$)—N(O$R_9$)—, —C(=N—O—$R_8$)—, —CH(—N(—O—$R_8$)-Q-$R_4$)—,

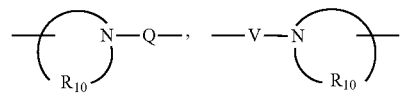

wherein V is —C($R_6$)—, or

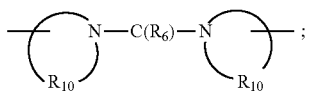

or $R_5$ is bonded to $X_1$ and $R_5$ is

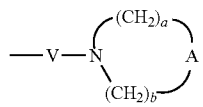

wherein V is —C($R_6$)— or

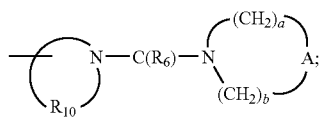

or a pharmaceutically acceptable salt thereof.

In another embodiment, there is provided a compound of Formula V, which is a prodrug:

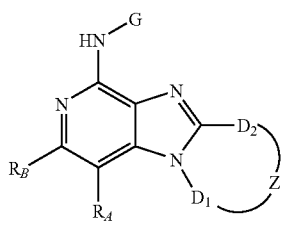

V wherein:

G is selected from the group consisting of:
—C(O)—R',
α-aminoacyl,
α-aminoacyl-α-aminoacyl,
—C(O)—O—R',
—C(O)—N(R")R',
—C(=NY')—R',
—CH(OH)—C(O)—OY',
—CH(O$C_{1-4}$ alkyl)$Y_0$,
—$CH_2Y_1$, and
—CH($CH_3$)$Y_1$;

R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —S(O)$_2$—$NH_2$, with the proviso that R" can also be hydrogen;

α-aminoacyl is an α-aminoacyl group derived from an α-amino acid selected from the group consisting of racemic, D-, and L-amino acids;

Y' is selected from the group consisting of hydrogen, $C_{1-6}$ alkyl, and benzyl;

$Y_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N—$C_{1-6}$ alkylamino-$C_{1-4}$ alkylenyl;

$Y_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl;

$D_1$ is selected from the group consisting of —O—, —N(-$Q_1$-$R_4$)—, and —CH($R_1$)—;

$D_2$ is selected from the group consisting of —O—, —N(-$Q_2$-$R_4$)—, and —$CH_2$—;

with the proviso that when $D_1$ is —CH($R_1$)— then $D_2$ is —O— or —N(-$Q_2$-$R_4$)—;

Z is selected from the group consisting of —($CH_2$)$_n$— and —($CH_2$)$_c$—C($R_{2a}$)($R_2$)—($CH_2$)$_d$—;

or -$D_1$-Z-$D_2$-, together with the imidazo ring atoms to which $D_1$ and $D_2$ are attached, forms a fused ring selected from the group consisting of

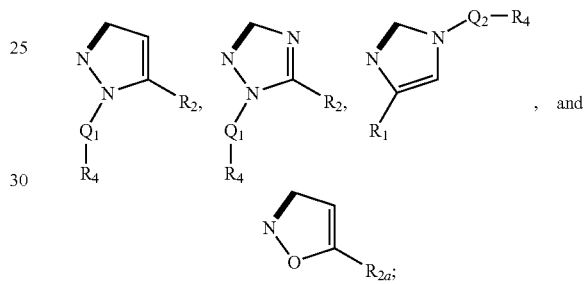

wherein the highlighted bond indicates the position where the ring is fused;

$R_1$ is selected from the group consisting of:
—$X_1$—$R_4$,
—$X_1$—Y—$R_4$,
—$X_1$—Y—X"—Y—$R_4$, and
—$X_1$—$R_5$;

$R_{2a}$ is selected from the group consisting of hydrogen and $C_{1-4}$ alkyl optionally substituted by hydroxy or halogen;

$R_2$ is selected from the group consisting of hydrogen, hydroxy, $C_{1-4}$ alkoxy, and $C_{1-4}$ alkyl optionally substituted by hydroxy or halogen;

c and d are independently 0, 1, or 2 with the proviso that c+d is ≦2;

with the proviso that when c and/or d is 0 then $R_2$ is other than hydroxy or $C_{1-4}$ alkoxy;

n is 1, 2, or 3;

$R_A$ and $R_B$ are each independently selected from the group consisting of:
hydrogen,
halogen,
alkyl,
alkenyl,
alkoxy,
alkylthio, and
—N($R_9$)$_2$;

or when taken together, $R_A$ and $R_B$ form a fused aryl or heteroaryl ring containing one heteroatom selected from the group consisting of N and S, wherein the fused aryl or heteroaryl ring is unsubstituted or substituted by one or more R groups, or substituted by one $R_3$ group, or substituted by one $R_3$ group and one R group;

or when taken together, $R_A$ and $R_B$ form a fused 5 to 7 membered saturated ring, optionally containing one heteroatom selected from the group consisting of N and S, and unsubstituted or substituted by one or more R groups;

R is selected from the group consisting of:
halogen,
hydroxy,
alkyl,
alkenyl,
haloalkyl,
alkoxy,
alkylthio, and
—N($R_9$)$_2$;

$R_3$ is selected from the group consisting of:
—Z'—$R_4$,
—Z'—X"—$R_4$,
—Z'—X"—Y—$R_4$,
—Z'—X"—Y—X"—Y—$R_4$, and
—Z'—X"—$R_5$;

$X_1$ is selected from the group consisting of alkylene, alkenylene, and alkynylene, wherein the alkylene, alkenylene, and alkynylene are optionally interrupted by one or more —O— groups, and optionally substituted by a hydroxy or methoxy group;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,
—C(=N—O—$R_8$)—,
—CH(—N(—O—$R_8$)-Q-$R_4$)—,

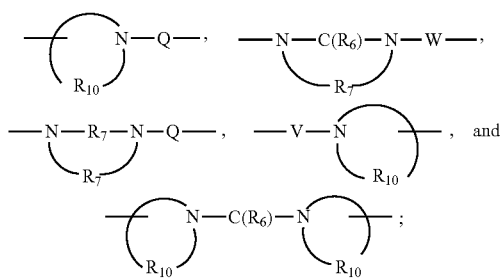

Z' is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo; with the proviso that when $R_4$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_4$ is heterocyclyl, then the one or more substituents may also be independently selected from the group consisting of arylalkylenyl, and aminocarbonyl;

$R_5$ is selected from the group consisting of:

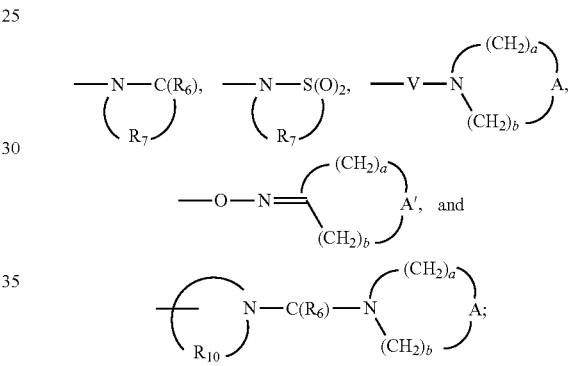

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;

$R_9$ is selected from the group consisting of hydrogen and alkyl;

$R_{10}$ is $C_{3-8}$ alkylene;

A is selected from the group consisting of —CH$_2$—, —O—, —C(O)—, —S(O)$_{0-2}$—, and —N(-Q-$R_4$)—;

A' is selected from the group consisting of —O—, —S(O)$_{0-2}$—, —N(-Q-$R_4$)—, and —CH$_2$—;

Q, $Q_1$, and $Q_2$ are each independently selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—; with the proviso that when $Q_2$ is a bond then $R_4$ is hydrogen, $C_{1-3}$ alkyl, or pyridin-3-ylmethyl;

V is selected from the group consisting of —C($R_6$)—, —O—C($R_6$)—, —N($R_8$)—C($R_6$)—, and —S(O)$_2$—;

W is selected from the group consisting of a bond, —C(O)—, and —S(O)$_2$—; and a and b are independently integers from 1 to 6 with the proviso that a+b is ≦7;

with the proviso that $X_1$ can also be a bond when:
$R_4$ is bonded to $X_1$; or Y is bonded to $X_1$ and Y is —C($R_6$)—, —C($R_6$)—O—, —C($R_6$)—N($R_8$)—, —C($R_6$)—N(O$R_9$)—, —C(=N—O—$R_8$)—, —CH(—N(—O—$R_8$)-Q-$R_4$)—,

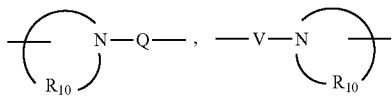

wherein V is —C($R_6$)—, or

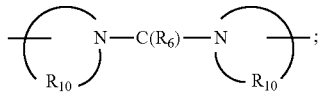

or $R_5$ is bonded to $X_1$ and $R_5$ is

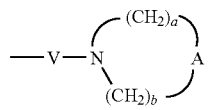

wherein V is —C($R_6$)— or

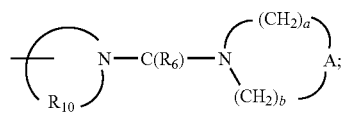

or a pharmaceutically acceptable salt thereof.

As used herein, the terms "alkyl", "alkenyl", "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene", "alkenylene", and "alkynylene" are the divalent forms of the "alkyl", "alkenyl", and "alkynyl" groups defined above. The terms, "alkylenyl", "alkenylenyl", and "alkynylenyl" are used when "alkylene", "alkenylene", and "alkynylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. In some embodiments, the term "heteroaryl" includes one ring that contains 2-5 carbon atoms, 1-3 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. In some embodiments, the term "heterocyclyl" includes one ring that contains 2-5 carbon atoms, 1-3 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicyclic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene", "heteroarylene", and "heterocyclylene", respectively, are substituted. For example, an alkylarylenyl group comprises an arylene moiety to which an alkyl group is attached.

The term "fused aryl ring" includes fused carbocyclic aromatic rings or ring systems. Examples of fused aryl rings include benzo, naphtho, fluoreno, and indeno.

The term "fused heteroaryl ring" includes the fused forms of 5 or 6 membered aromatic rings that contain one heteroatom selected from S and N. Examples of fused heteroaryl rings include pyrido and thieno.

The term "fused 5 to 7 membered saturated ring" includes rings which are fully saturated except for the bond where the ring is fused. In one example, the ring is a cyclohexene ring.

In other examples wherein one heteroatom (N or S) is present, the ring is tetrahydropyrido or dihydrothieno.

When a group (or substituent or variable) is present more than once in any Formula described herein, each group (or substituent or variable) is independently selected, whether explicitly stated or not. For example, for the formula —N(R$_9$)$_2$ each R$_9$ group is independently selected. In another example, when two Y groups are present and both contain an R$_8$ group, each Y group and each R$_8$ group is independently selected. In a further example, when more than one Y group is present (e.g., R$_1$ and R$_3$ each contains a Y group) and each Y group contains one or more R$_7$ groups, then each Y group is independently selected, and each R$_7$ group is independently selected.

The invention is inclusive of the compounds described herein (including intermediates) in any of their pharmaceutically acceptable forms, including isomers (e.g., diastereomers and enantiomers), salts, solvates, polymorphs, prodrugs, and the like. In particular, the invention specifically includes enantiomerically pure compounds, mixtures of enantiomers in any ratio, as well as racemic compounds. Ratios of a compound to its enantiomer include, for example, 50:50 or higher, 90:10 or higher, 95:5 or higher, 99:1 or higher, 99.9:0.1 or higher, or 100:0. It should be understood that the term "compound" includes any or all of such forms, whether explicitly stated or not (although at times, "salts" are explicitly stated).

The term "prodrug" means a compound that can be transformed in vivo to yield an immune response modifying compound, including any of the salt, solvated, polymorphic, or isomeric forms described above. The prodrug, itself, may be an immune response modifying compound, including any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For any of the compounds presented herein, each one of the following variables (e.g., D$_1$, D$_2$, Z, R, R$_1$, R$_3$, R$_4$, R$_A$, R$_B$, R$_{A1}$, R$_{B1}$, Q, m, n, p, q, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments, including embodiments of Formula I or Formula V, R$_A$ and R$_B$ are each independently selected from the group consisting of hydrogen, halogen, alkyl, alkenyl, alkoxy, alkylthio, and —N(R$_9$)$_2$; or when taken together, R$_A$ and R$_B$ form a fused aryl or heteroaryl ring containing one heteroatom selected from the group consisting of N and S, wherein the fused aryl or heteroaryl ring is unsubstituted or substituted by one or more R groups, or substituted by one R$_3$ group, or substituted by one R$_3$ group and one R group; or when taken together, R$_A$ and R$_B$ form a fused 5 to 7 membered saturated ring, optionally containing one heteroatom selected from the group consisting of N and S, and unsubstituted or substituted by one or more R groups. For certain of these embodiments, R$_A$ and R$_B$ are each independently selected from the group consisting of hydrogen, halogen, alkyl, alkenyl, alkoxy, alkylthio, and —N(R$_9$)$_2$. Alternatively, for certain of these embodiments, R$_A$ and R$_B$ form a fused aryl ring or heteroaryl ring containing one heteroatom selected from the group consisting of N and S, wherein the fused aryl or heteroaryl ring is unsubstituted or substituted by one or more R groups, or substituted by one R$_3$ group, or substituted by one R$_3$ group and one R group. For certain of these embodiments, R$_A$ and R$_B$ form a benzo ring which is unsubstituted or substituted by one or more R groups, or substituted by one R$_3$ group, or substituted by one R$_3$ group and one R group. For certain of these embodiments, the benzo ring is substituted by one R group. Alternatively, for certain of these embodiments, the benzo ring is substituted by one R$_3$ group. For certain embodiments, R$_A$ and R$_B$ form a benzo ring which is unsubstituted. Alternatively, for certain of these embodiments, R$_A$ and R$_B$ form a pyrido ring which is unsubstituted or substituted by one or more R groups, or substituted by one R$_3$ group, or substituted by one R$_3$ group and one R group. For certain of these embodiments, the pyrido ring is substituted by one R group. Alternatively, for certain of these embodiments, the pyrido ring is substituted by one R$_3$ group. For certain of these embodiments, R$_A$ and R$_B$ form a pyrido ring which is unsubstituted. For certain of these embodiments, the pyrido ring is

wherein the highlighted bond indicates the position where the ring is fused. Alternatively for certain embodiments, R$_A$ and R$_B$ form a fused 5 to 7 membered saturated ring, optionally containing one heteroatom selected from the group consisting of N and S, and unsubstituted or substituted by one or more R groups. For certain of these embodiments, the fused ring is substituted by one R group. For certain of these embodiments, the fused ring is unsubstituted. For certain of these embodiments, R$_A$ and R$_B$ form a fused cyclohexene ring that is unsubstituted or substituted by one, two, three, or four R groups. For certain of these embodiments, the fused cyclohexene ring is substituted by one R group. For of these certain embodiments, R$_A$ and R$_B$ form a fused cyclohexene ring that is unsubstituted. Alternatively, for certain of embodiments, R$_A$ and R$_B$ form a tetrahydropyrido ring that is unsubstituted or substituted on one or more ring carbon atoms by one, two, or three R groups. For certain of these embodiments, the tetrahydropyrido ring is substituted by one R group. For certain of these embodiments, R$_A$ and R$_B$ form a tetrahydropyrido ring that is unsubstituted. For certain of these embodiments, the tetrahydropyrido ring is

wherein the highlighted bond indicates the position where the ring is fused.

For certain embodiments, including embodiments of Formula IV, R$_{A1}$ and R$_{B1}$ are each independently selected from the group consisting of hydrogen, halogen, alkyl, alkenyl, alkoxy, alkylthio, and —N(R$_9$)$_2$. For certain of these embodiments, R$_{A1}$ is hydrogen or alkyl, and R$_{B1}$ is alkyl, For certain of these embodiments, R$_{A1}$ and R$_{B1}$ are each methyl.

For certain embodiments, including any one of the above embodiments of Formula II, p is 0.

For certain embodiments, including any one of the above embodiments of Formula III, q is 0.

For certain embodiments, including any one of the above embodiments of Formula II or Formula III, m is 0.

For certain embodiments, including any one of the above embodiments of Formulas I, II, III, or V where R is present, R is selected from the group consisting of halogen, hydroxy, alkyl, alkenyl, haloalkyl, alkoxy, alkylthio, and —N($R_9$)$_2$.

For certain embodiments, including any one of the above embodiments of Formulas I, II, III, or V where R is present, R is halogen or hydroxy.

For certain embodiments, including any one of the above embodiments of Formulas I, II, III, or V where $R_3$ is present, $R_3$ is selected from the group consisting of —Z'—$R_4$, —Z'—X"—$R_4$, —Z'—X"—Y—$R_4$, —Z'—X"—Y—X"—Y—$R_4$, and —Z'—X"—$R_5$.

For certain embodiments, including any one of the above embodiments of Formulas I, II, III, or V where $R_3$ is present, $R_3$ is —Z'—$R_4$. For certain of these embodiments, $R_4$ in —Z'—$R_4$ is selected from the group consisting of alkyl, alkenyl, alkynyl, aryl, heteroaryl, and heterocyclyl wherein alkyl and alkenyl are unsubstituted or substituted by one or more substituents independently selected from the group consisting of hydroxy, alkoxy, cyano, and aryl; wherein aryl and heteroaryl are unsubstituted or substituted by one or more substituents independently selected from the group consisting of alkyl, alkoxy, hydroxyalkyl, halogen, cyano, and dialkylamino; and wherein heterocyclyl is unsubstituted or substituted by one or more substituents independently selected from alkyl and oxo.

For certain embodiments, including any one of the above embodiments of Formulas I, II, III, or V where $R_3$ is present, $R_3$ is benzyloxy.

Alternatively, for certain embodiments, including any one of the above embodiments of Formulas I, II, III, or V where $R_3$ is —Z'—$R_4$, Z' is a bond and $R_4$ is heterocyclyl which is selected from the group consisting of pyrrolidinyl, piperidinyl, oxazolidinyl, morpholinyl, and thiomorpholinyl, each of which is unsubstituted or substituted by one or more substituents independently selected from alkyl and oxo. For certain of these embodiments, —Z'—$R_4$ is 2-oxopyrrolidin-1-yl, morpholin-1-yl, or 2-oxo-1,3-oxazolidin-3-yl.

For certain embodiments, including any one of the above embodiments of Formulas I, II, III, or V where $R_3$ is present, $R_3$ is —Z'—X"—$R_4$, except where $R_3$ is —Z—$R_4$. For certain of these embodiments, in —Z—X"—$R_4$, X" is $C_{1-3}$ alkylene or $C_{1-3}$ alkenylene, and $R_4$ is heterocyclyl or heteroaryl wherein heterocyclyl is unsubstituted or substituted by one or more substituents independently selected from alkyl and oxo, and wherein heteroaryl is unsubstituted or substituted by one or more substituents independently selected from the group consisting of alkyl, alkoxy, halogen, cyano, and dialkylamino. For certain of these embodiments, $R_4$ is heterocyclyl which is selected from the group consisting of pyrrolidinyl, piperidinyl, morpholinyl, and thiomorpholinyl, each of which is unsubstituted or substituted by one or more substituents independently selected from alkyl and oxo. Alternatively, for certain of these embodiments, $R_4$ is heteroaryl which is selected from the group consisting of thiazolyl, imidazolyl, isoxazolyl, and pyridinyl each of which is unsubstituted or substituted by one or more substituents independently selected from the group consisting of alkyl, alkoxy, halogen, cyano, and dialkylamino.

For certain embodiments, including any one of the above embodiments of Formulas I, II, III, or V where $R_3$ is present, $R_3$ is —Z'—X"—Y—$R_4$, except where $R_3$ is —Z'—$R_4$ or —Z'—X"—$R_4$. For certain of these embodiments, in —Z'—X"—Y—$R_4$, X" is selected from the group consisting of $C_{1-3}$ alkylene, $C_{1-3}$ alkenylene, piperidin-1,4-diyl, and phenylene, Y is selected from the group consisting of —C($R_6$)—, —C($R_6$)—O—, —C($R_6$)—N($R_8$)—, —N($R_8$)-Q-, and —S(O)$_2$— wherein Q is selected from the group consisting of a bond, —C(O)—, —S(O)$_2$—, and —C($R_6$)—N($R_8$)—, $R_6$ is selected from the group consisting of =O and =S, and $R_8$ is selected from the group consisting of hydrogen, $C_{1-4}$ alkyl, and $C_{1-4}$ alkoxy$C_{1-4}$ alkylenyl; and $R_4$ is selected from the group consisting of hydrogen, alkyl, aryl, heteroaryl, and heterocyclyl; wherein alkyl is unsubstituted or substituted by one or more substituents independently selected from the group consisting of hydroxy, alkoxy, and aryl; wherein aryl is unsubstituted or substituted by one or more substituents independently selected from the group consisting of alkyl, halogen, cyano, dialkylamino, and alkoxy; and wherein heterocyclyl is unsubstituted or substituted by one or more substituents independently selected from the group consisting of alkyl and oxo. For certain of these embodiments, Y is —N($R_8$)-Q- wherein $R_8$ is hydrogen, Q is —S(O)$_2$—, —C(O)—, or —C(O)—NH—, and $R_4$ is $C_{1-3}$ alkyl or pyridyl. Alternatively, for certain of these embodiments, Y is —C(O)— and $R_4$ is heterocyclyl. For certain of these embodiments, heterocyclyl is selected from the group consisting of pyrrolidinyl, piperidinyl, thiazolidinyl, aziridinyl, azepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and piperazinyl, each of which is unsubstituted or substituted by one or more substituents selected from the group consisting of alkyl and oxo.

For certain embodiments, including any one of the above embodiments of Formulas I, II, III, or V where $R_3$ is present, $R_3$ is —Z'—X"—$R_5$, except where $R_3$ is —Z'—$R_4$, —Z'—X"—$R_4$, or —Z'—X"—Y—$R_4$. For certain of these embodiments, X" is selected from the group consisting of $C_{1-3}$ alkylene and phenylene, and $R_5$ is selected from the group consisting of

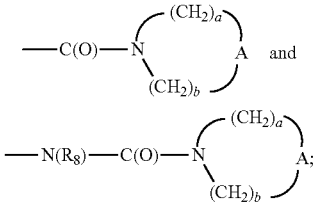

wherein A is —O—, —S—, or —SO$_2$—; $R_8$ is hydrogen or $C_{1-4}$ alkyl; and a and b are each independently an integer of 1 to 3.

For certain embodiments, including any one of the above embodiments of Formulas I, II, III, or V where $R_3$ is present, $R_3$ is at the 7- or 8-position. For certain of these embodiments, $R_3$ is at the 7-position. Alternatively, for certain of these embodiments, $R_3$ is at the 8-position. Herein, the 7- and 8-positions refer to positions of a 1H-imidazo[4,5-c]quinoline or 1H-imidazo[4,5-c]naphthyridine ring system as indicated in the exemplary structures below.

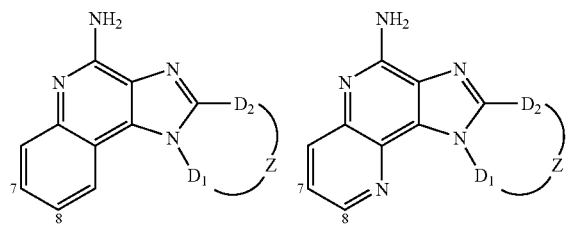

For certain embodiments, including any one of the above embodiments of Formulas I, II, III, IV, or V, $D_1$ is selected from the group consisting of —O—, —N(-$Q_1$-$R_4$)—, and —CH($R_1$)—; $D_2$ is selected from the group consisting of —O—, —N(-$Q_2$-$R_4$)—, and —CH$_2$—; with the proviso that when $D_1$ is —CH($R_1$)— then $D_2$ is —O— or —N(-$Q_2$-$R_4$)—; and Z is selected from the group consisting of —(CH$_2$)$_n$— and —(CH$_2$)$_c$—C($R_{2a}$)($R_2$)—(CH$_2$)$_d$—; or -$D_1$-Z-$D_2$-, together with the imidazo ring atoms to which $D_1$ and $D_2$ are attached, forms a fused ring selected from the group consisting of

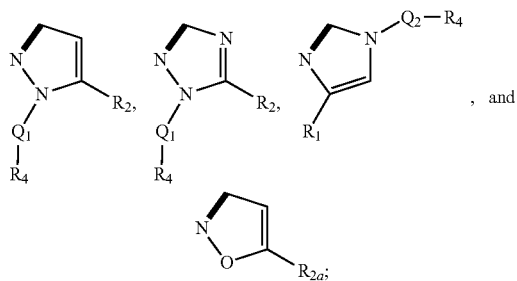

wherein the highlighted bond indicates the position where the ring is fused.

For certain embodiments, including any one of the above embodiments, $D_1$ is selected from the group consisting of —O—, —N(-$Q_1$-$R_4$)—, and —CH($R_1$)—; $D_2$ is selected from the group consisting of —O—, —N(-$Q_2$-$R_4$)—, and —CH$_2$—; with the proviso that when $D_1$ is —CH($R_1$)— then $D_2$ is —O— or —N(-$Q_2$-$R_4$)—; and Z is selected from the group consisting of —(CH$_2$)$_n$— and —(CH$_2$)$_c$—C($R_{2a}$)($R_2$)—(CH$_2$)$_d$—.

For certain embodiments, including any one of the above embodiments of Formulas I, II, III, IV, or V, Z is —(CH$_2$)$_n$— or —(CH$_2$)$_c$—C($R_{2a}$)($R_2$)—(CH$_2$)$_d$—. For certain of these embodiments, Z is —(CH$_2$)$_n$—.

For certain embodiments, including any one of the above embodiments, n is 1, 2, or 3.

For certain embodiments, including any one of the above embodiments, n is 1 or 2.

For certain embodiments, including any one of the above embodiments, n is 1. Alternatively, for certain other embodiments, n is 2.

For certain embodiments, including any one of the above embodiments except embodiments where n is 1 or 2, n is 3.

For certain embodiments, including any one of the above embodiments, Z is —(CH$_2$)$_c$—C($R_{2a}$)($R_2$)—(CH$_2$)$_d$—, except where Z is —(CH$_2$)$_n$—.

For certain of these embodiments, including any one of the above embodiments where $R_{2a}$ is present, $R_{2a}$ is selected from the group consisting of hydrogen and $C_{1-4}$ alkyl optionally substituted by hydroxy or halogen. For certain of these embodiments, $R_{2a}$ is hydrogen. For certain of these embodiments, $R_{2a}$ is methyl.

For certain embodiments, including any one of the above embodiments where $R_2$ is present, $R_2$ is selected from the group consisting of hydrogen, hydroxy, $C_{1-4}$ alkoxy, and $C_{1-4}$ alkyl optionally substituted by hydroxy or halogen. For certain of these embodiments, $R_2$ is selected from the group consisting of hydroxy, methyl, ethyl, propyl, 2-methylpropyl, and 2-fluoro-2-methylpropyl.

For certain embodiments, including any one of the above embodiments, $D_1$ is —CH($R_1$)—, and $D_2$ is —O— or —N(-$Q_2$-$R_4$)—; or $D_1$ is —O— or —N(-$Q_1$-$R_4$)—, and $D_2$ is —CH$_2$—. For certain of these embodiments, $D_1$ is —CH($R_1$)—, and $D_2$ is —O— or —N(-$Q_2$-$R_4$)—. Alternatively, for certain of these embodiments, $D_1$ is —O— or —N(-$Q_1$-$R_4$)—, and $D_2$ is —CH$_2$—. For certain of these embodiments, $D_1$ is —N(-$Q_1$-$R_4$)—. For certain of these embodiments, $Q_1$ is selected from the group consisting of a bond, —C($R_6$)—, —S(O)$_2$—, —C($R_6$)—N($R_8$)—W—, —S(O)$_2$—N($R_8$)—, and —C($R_6$)—O—. For certain of these embodiments, $Q_1$ is a bond, —C(O)—, —S(O)$_2$—, —C(O)—N($R_8$)—, —C(S)—N($R_8$)—, —S(O)$_2$—N($R_8$)—, or —C(O)—O—; each $R_8$ is independently selected from the group consisting of hydrogen, $C_{1-4}$ alkyl, hydroxy$C_{1-4}$ alkyl, and $C_{1-4}$ alkoxy$C_{1-4}$ alkyl; and $R_4$ in -$Q_1$-$R_4$ is hydrogen, alkyl, aryl, arylalkylenyl, heteroaryl, or heterocyclyl wherein alkyl, aryl, arylalkylenyl, heteroaryl, and heterocyclyl are unsubstituted or substituted by one or more substituents independently selected from the group consisting of hydroxy, halogen, alkoxy, alkyl, haloalkyl, and dialkylamino. For certain of these embodiments, $Q_1$ is selected from the group consisting of —C(O)—, —S(O)$_2$—, —C(O)—N($R_8$)—, and —S(O)$_2$—N($R_8$)—. For certain of these embodiments, $Q_1$ is —C(O)— or —S(O)$_2$—. Alternatively, for certain of these embodiments, $Q_1$ is a bond, and $R_4$ in -$Q_1$-$R_4$ is alkyl or heterocyclyl. For certain of these embodiments, $R_4$ is tetrahydro-2H-pyran-4-yl.

For certain embodiments, including any one of the above embodiments where $D_1$ is —O— or —N(-$Q_1$-$R_4$)—, and $D_2$ is —CH$_2$—, $D_1$ is —O—.

For certain embodiments, including any one of the above embodiments where $D_1$ is —CH($R_1$)—, and $D_2$ is —O— or —N(-$Q_2$-$R_4$)—, $D_2$ is —O—. Alternatively, $D_2$ is —N(-$Q_2$-$R_4$)—. For certain of these embodiments, $Q_2$ is selected from the group consisting of —C(O)—, —S(O)$_2$—, and —C(O)—NH—. For certain of these embodiments, $Q_2$ is —S(O)$_2$— and $R_4$ in -$Q_2$-$R_4$ is methyl. Alternatively, for certain of these embodiments, $Q_2$ is a bond, and $R_4$ in -$Q_2$-$R_4$ is hydrogen, $C_{1-3}$ alkyl, or pyridin-3-ylmethyl.

For certain embodiments, including any one of the above embodiments where $R_1$ is present, $R_1$ is selected from the group consisting of —$X_1$—$R_4$, —$X_1$—Y—$R_4$, —$X_1$—Y—X"—Y—$R_4$, and —$X_1$—$R_5$.

For certain embodiments, including any one of the above embodiments where $R_1$ is present, $R_1$ is —$X_1$—$R_4$. For certain of these embodiments, $R_4$ in —$X_1$—$R_4$ is selected from the group consisting of alkyl, aryl, arylalkylenyl, heteroaryl, and heteroarylalkylenyl, each of which is unsubstituted or substituted by one or more substituents selected from the group consisting of halogen, hydroxy, and alkoxy. For certain of these embodiments, $R_4$ is $C_{1-3}$ alkyl optionally substituted by hydroxy or one or more fluorine atoms. Alternatively, $R_4$ is phenyl, benzyl, pyridinyl, or pyridinylmethyl, each of which is unsubstituted or substituted by one or more substituents selected from the group consisting of halogen, hydroxy, and alkoxy. Alternatively, $R_4$ in —$X_1$—$R_4$ is selected from the group consisting of alkyl, alkenyl, alkynyl, aryl, heteroaryl, and heterocyclyl, each of which is unsubstituted or substituted by one or more substituents independently selected from the group consisting of alkyl, alkoxy, hydroxyalkyl, haloalkyl, halogen, hydroxy, aryl, heteroaryl, and heterocyclyl; and wherein when $R_4$ is heteroaryl, then the one or more substituents may also be independently selected from the group consisting of haloarylenyl, alkoxyarylenyl, alkylarylenyl, and arylalkylenyl; and wherein when $R_4$ is heterocyclyl, then the one or more substituents may also be independently selected from the group consisting of arylalkylenyl and aminocarbonyl. For certain of these embodiments, $R_4$ is heterocyclyl which is selected from the group consisting of morpholinyl, thiomorpholinyl, piperidinyl, pyrrolidinyl, thiazolidinyl, dihydroisoquinolin-(1H)-yl, octahydroisoquinolin-(1H)-yl, 1,3-dioxolanyl, oxetanyl, tetrahydrofuranyl, tetrahydropyranyl, each of which is unsubstituted or substituted by one or more substituents independently selected from the group consisting of $C_{1-4}$ alkyl, hydroxy$C_{1-4}$ alkyl, hydroxy, aminocarbonyl, aryl$C_{1-4}$ alkylenyl, and 5 to 7 membered heterocyclyl containing one or two heteroatoms. Alternatively, $R_4$ is heteroaryl which is selected from the group consisting of pyridyl, pyrazolyl, oxazolyl, and triazolyl, each of which is unsubstituted or substituted by one or more substituents independently selected from the group consisting of $C_{1-4}$ alkyl, hydroxy$C_{1-4}$ alkyl, halo$C_{1-4}$ alkyl, aryl, aryl substituted by fluoro, chloro, methyl, or methoxy, aryl$C_{1-4}$ alkylenyl, and heteroaryl. Alternatively, for certain of these embodiments where $R_4$ in —$X_1$—$R_4$ is selected from the group consisting of alkyl, alkenyl, alkynyl, aryl, heteroaryl, and heterocyclyl, $R_4$ is selected from the group consisting of $C_{1-4}$ alkyl, $C_{1-4}$ alkenyl, and $C_{1-4}$ alkynyl, each of which is unsubstituted or substituted by one or more substituents independently selected from the group consisting of hydroxy, halogen, and aryl. For certain of these embodiments, $R_4$ is $C_{1-4}$ alkyl. Alternatively, for certain of these embodiments, $R_4$ is aryl which is unsubstituted or substituted by one or more substituents independently selected from the group consisting of halogen, hydroxy, $C_{1-4}$ alkoxy, $C_{1-4}$ alkyl, and hydroxy$C_{1-4}$ alkyl.

For certain embodiments, including any one of the above embodiments where $R_1$ is —$X_1$—$R_4$, $X_1$ is a bond or alkylene. For certain of these embodiments, $X_1$ is a bond. Alternatively, for certain of these embodiments, $X_1$ is $C_{1-4}$ alkylene. For certain of these embodiments, $X_1$ is —$CH_2$—.

For certain embodiments, including any one of the above embodiments where $R_1$ is —$X_1$—$R_4$, alternatively, $X_1$ is $C_{1-4}$ alkylene substituted by a hydroxy or methoxy group.

For certain embodiments, including any one of the above embodiments where $R_1$ is —$X_1$—$R_4$, alternatively, $X_1$ is selected from the group consisting of alkylene and alkenylene, wherein the alkylene and alkenylene are optionally interrupted by one or more —O— groups.

For certain of these embodiments, $X_1$ is $C_{2-3}$ alkylene interrupted by one —O— group.

For certain embodiments, including any one of the above embodiments where $R_1$ is —$X_1$—$R_4$, alternatively, $X_1$ is $C_{2-3}$ alkenylene or $C_{2-3}$ alkynylene.

For certain embodiments, where $R_1$ is present, $R_1$ is —$X_1$—$Y$—$R_4$, except where $R_1$ is —$X_1$—$R_4$.

For certain embodiments, including any one of the above embodiments where $R_1$ is present, $R_1$ is —$X_1$—$Y$—$X''$—$Y$—$R_4$, except where $R_1$ is —$X_1$—$Y$—$R_4$ or —$X_1$—$R_4$.

For certain embodiments, including any one of the above embodiments where $R_1$ is present, $R_1$ is —$X_1$—$R_5$, except where $R_1$ is —$X_1$—$Y$—$X''$—$Y$—$R_4$, —$X_1$—$Y$—$R_4$ or —$X_1$—$R_4$.

For certain embodiments, including any one of the above embodiments where $R_1$ is —$X_1$—$R_5$, —$X_1$—$Y$—$X''$—$Y$—$R_4$, —$X_1$—$Y$—$R_4$ or —$X_1$—$R_4$, $X_1$ is $C_{1-4}$ alkylene. For certain of these embodiments, Y is —C(O)—, —S(O)$_2$—, —N($R_8$)-Q-, or —C(O)—NH—. For certain of these embodiments, Q is —C(O)—, —S(O)$_2$, —S(O)$_2$—N($R_8$)—, or —C(O)—N($R_8$)—.

For certain embodiments, including any one of the above embodiments where $R_1$ is —$X_1$—$Y$—$X''$—$Y$—$R_4$ or —$X_1$—$Y$—$R_4$, $R_4$ in $Y$—$R_4$ is alkyl, aryl, arylalkylenyl, or heteroaryl, wherein aryl, arylalkylenyl, and heteroaryl are optionally substituted by alkyl. For certain of these embodiments, $X_1$ is $C_{1-4}$ alkylene.

For certain embodiments, including any one of the above embodiments where $R_1$ is —$X_1$—$Y$—$R_4$, Y is —S—, —S(O)$_2$—, or N($R_8$)-Q- wherein Q is a bond, —S(O)$_2$—, —C(O)—, —C(O)—O—, —C(O)—N($R_8$)—, —C(S)—N($R_8$)—, or —S(O)$_2$—N($R_8$)—; each $R_8$ is independently selected from the group consisting of hydrogen, $C_{1-4}$ alkyl, hydroxy$C_{1-4}$ alkyl, and $C_{1-4}$ alkoxy$C_{1-4}$ alkyl; and $R_4$ is hydrogen, alkyl, aryl, arylalkylenyl, heteroaryl, or heterocyclyl wherein alkyl, aryl, arylalkylenyl, heteroaryl, and heterocyclyl are unsubstituted or substituted by one or more substituents independently selected from the group consisting of hydroxy, halogen, alkoxy, alkyl, haloalkyl, and dialkylamino. For certain of these embodiments, Y is —NH—S(O)$_2$—, —NH—C(O)—, —NH—S(O)$_2$—N($R_8$)—, —NH—C(O)—N($R_8$)—, —NH—C(S)—N($R_8$)—, —NH—C(O)—O—, or —N($R_8$)—; and $R_8$ is hydrogen, methyl, ethyl, 2-hydroxyethyl, or 2-methoxyethyl. Alternatively, for certain of these embodiments, Y is —S— or —S(O)$_2$—; and $R_4$ is alkyl or aryl. For certain of these embodiments, $X_1$ is $C_{1-3}$ alkylene optionally substituted by a hydroxy or methoxy group. For certain of these embodiments, $X_1$ is —(CH$_2$)$_{1-3}$—. Alternatively, for certain of these embodiments, $X_1$ is $C_{2-3}$ alkylene substituted by one hydroxy group.

For certain embodiments, including any one of the above embodiments where $R_1$ is —$X_1$—$Y$—$R_4$, except where excluded, Y is

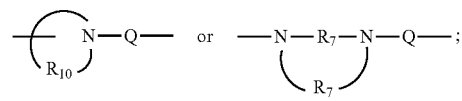

Q is a bond, —C(O)—, —S(O)$_2$—, —S(O)$_2$—N($R_8$)—, —C(O)—N($R_8$)—, —C(S)—N($R_8$)—, or —C(O)—O—; $R_7$ is $C_{2-3}$ alkylene; $R_8$ is hydrogen or $C_{1-4}$ alkyl; $R_{10}$ is $C_{4-6}$ alkylene; and $R_4$ in $Y$—$R_4$ is hydrogen, alkyl, alkenyl, aryl, arylalkylenyl, heteroaryl, or heterocyclyl wherein alkyl, alkenyl, aryl, arylalkylenyl, heteroaryl, and heterocyclyl are unsubstituted or substituted by one or more substituents independently selected from the group consisting of hydroxy, halogen, alkoxy, alkyl, and haloalkyl. For certain of these embodiments, Y is

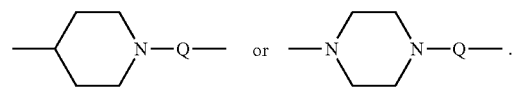

For certain of these embodiments, $X_1$ is a bond or —CH$_2$—, and Y is

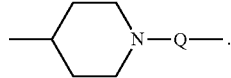

Alternatively, for certain of these embodiments, $X_1$ is a —CH$_2$— or —(CH$_2$)$_2$—, and Y is

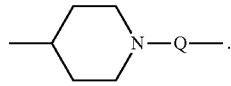

For certain embodiments, including any one of the above embodiments where $R_1$ is —X$_1$—Y—R$_4$, except where excluded, Y is —O—, and $R_4$ is aryl which is unsubstituted or substituted by one or more substituents independently selected from the group consisting of alkyl, alkoxy, halogen, and dialkylamino. For certain of these embodiments, $X_1$ is $C_{1-4}$ alkylene.

For certain embodiments, including any one of the above embodiments where $R_1$ is —X$_1$—Y—R$_4$, except where excluded, Y is —C(O)—; and $R_4$ is alkyl, aryl, arylalkylenyl, heteroaryl, or heterocyclyl wherein alkyl, aryl, arylalkylenyl, heteroaryl, and heterocyclyl are unsubstituted or substituted by one or more substituents independently selected from the group consisting of hydroxy, halogen, alkoxy, alkyl, haloalkyl, and dialkylamino. For certain of these embodiments, $X_1$ is a bond. Alternatively, for certain of these embodiments, $X_1$ is $C_{1-4}$ alkylene.

For certain embodiments, including any one of the above embodiments where $R_1$ is —X$_1$—Y—X″—Y—R$_4$, $R_1$ is —X$_1$—Y$_a$—X″—Y$_b$—R$_4$; Y$_a$ is —O—; X″ is arylene; Y$_b$ is —C(O)—N(R$_8$)—; $R_4$ is hydrogen, alkyl, or aryl which is unsubstituted or substituted by one or more substituents independently selected from the group consisting of alkyl, alkoxy, halogen, and dialkylamino; and $R_8$ is hydrogen or $C_{1-4}$ alkyl. For certain of these embodiments, $X_1$ is $C_{1-4}$ alkylene.

For certain embodiments, including any one of the above embodiments where $R_1$ is —X$_1$—R$_5$, $R_5$ is

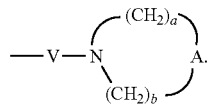

For certain of these embodiments, $X_1$ is $C_{1-4}$ alkylene. For certain of these embodiments, V is —C(O)— and A is —CH$_2$—, —O—, or —N(-Q-R$_4$)—. Alternatively, for certain of these embodiments, V is —N(R$_8$)—C(R$_6$)—; A is —O—; a and b are each 2 or 3; and $R_8$ is hydrogen or $C_{1-4}$ alkyl.

For certain embodiments, including any one of the above embodiments of Formulas I, II, III, IV, or V where the following definition is not excluded, -D$_1$-Z-D$_2$-, together with the imidazo ring atoms to which D$_1$ and D$_2$ are attached, forms a fused ring selected from the group consisting of

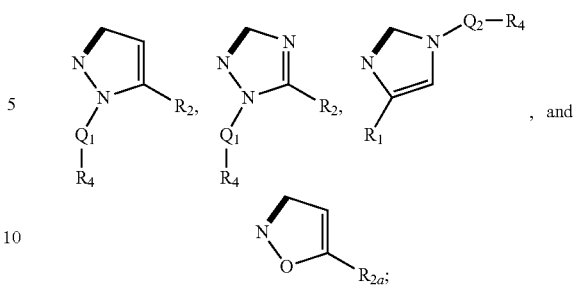

wherein the highlighted bond indicates the position where the ring is fused. For certain of these embodiments where $Q_1$ is present, $Q_1$ is any one of the embodiments of $Q_1$ defined above. For certain of these embodiments, $R_4$ in -Q$_1$-R$_4$ is any one of the embodiments of $R_4$ in -Q$_1$-R$_4$ defined above. For certain of these embodiments where $R_2$ is present, $R_2$ is any one of the embodiments of $R_2$ defined above. For certain of these embodiments where $R_{2a}$ is present, $R_{2a}$ is any one of the embodiments of $R_{2a}$ defined above. For certain of these embodiments where $Q_2$ is present, $Q_2$ is any one of the embodiments of $Q_2$ defined above. For certain of these embodiments, $R_4$ in -Q$_2$-R$_4$ is any one of the embodiments of $R_4$ in -Q$_2$-R$_4$ defined above. For certain of these embodiments, $R_1$ is any one of the embodiments of $R_1$ defined above.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo; with the proviso that when $R_4$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_4$ is heterocyclyl, then the one or more substituents may also be independently selected from the group consisting of arylalkylenyl, and aminocarbonyl.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino;

alkylamino; dialkylamino; (dialkylamino)alkyleneoxy; and, in the case of alkyl, alkenyl, alkynyl, and heterocyclyl, oxo.

For certain embodiments, $R_4$ is selected from the group consisting of alkyl, alkenyl, alkynyl, aryl, heteroaryl, and heterocyclyl wherein alkyl and alkenyl are unsubstituted or substituted by one or more substituents independently selected from the group consisting of hydroxy, alkoxy, cyano, and aryl; wherein aryl and heteroaryl are unsubstituted or substituted by one or more substituents independently selected from the group consisting of alkyl, alkoxy, hydroxyalkyl, halogen, cyano, and dialkylamino; and wherein heterocyclyl is unsubstituted or substituted by one or more substituents independently selected from alkyl and oxo.

For certain embodiments, $R_4$ is heterocyclyl which is selected from the group consisting of pyrrolidinyl, piperidinyl, oxazolidinyl, morpholinyl, and thiomorpholinyl, each of which is unsubstituted or substituted by one or more substituents independently selected from alkyl and oxo.

For certain embodiments, $R_4$ is heterocyclyl or heteroaryl wherein heterocyclyl is unsubstituted or substituted by one or more substituents independently selected from alkyl and oxo, and wherein heteroaryl is unsubstituted or substituted by one or more substituents independently selected from the group consisting of alkyl, alkoxy, halogen, cyano, and dialkylamino.

For certain embodiments, $R_4$ is heterocyclyl which is selected from the group consisting of pyrrolidinyl, piperidinyl, morpholinyl, and thiomorpholinyl, each of which is unsubstituted or substituted by one or more substituents independently selected from alkyl and oxo.

For certain embodiments, $R_4$ is heteroaryl which is selected from the group consisting of thiazolyl, imidazolyl, isoxazolyl, and pyridinyl each of which is unsubstituted or substituted by one or more substituents independently selected from the group consisting of alkyl, alkoxy, halogen, cyano, and dialkylamino.

For certain embodiments, $R_4$ is selected from the group consisting of hydrogen, alkyl, aryl, heteroaryl, and heterocyclyl; wherein alkyl is unsubstituted or substituted by one or more substituents independently selected from the group consisting of hydroxy, alkoxy, and aryl; wherein aryl is unsubstituted or substituted by one or more substituents independently selected from the group consisting of alkyl, halogen, cyano, dialkylamino, and alkoxy; and wherein heterocyclyl is unsubstituted or substituted by one or more substituents independently selected from the group consisting of alkyl and oxo.

For certain embodiments, $R_4$ is $C_{1-3}$ alkyl or pyridyl.

For certain embodiments, $R_4$ is heterocyclyl.

For certain embodiments, $R_4$ is selected from the group consisting of pyrrolidinyl, piperidinyl, thiazolidinyl, aziridinyl, azepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and piperazinyl, each of which is unsubstituted or substituted by one or more substituents selected from the group consisting of alkyl and oxo.

For certain embodiments, $R_4$ is hydrogen, alkyl, aryl, arylalkylenyl, heteroaryl, or heterocyclyl wherein alkyl, aryl, arylalkylenyl, heteroaryl, and heterocyclyl are unsubstituted or substituted by one or more substituents independently selected from the group consisting of hydroxy, halogen, alkoxy, alkyl, haloalkyl, and dialkylamino.

For certain embodiments, $R_4$ is alkyl or heterocyclyl.

For certain embodiments, $R_4$ is tetrahydro-2H-pyran-4-yl.

For certain embodiments, $R_4$ is hydrogen, $C_{1-3}$ alkyl, or pyridin-3-ylmethyl.

For certain embodiments, $R_4$ is selected from the group consisting of alkyl, aryl, arylalkylenyl, heteroaryl, and heteroarylalkylenyl, each of which is unsubstituted or substituted by one or more substituents selected from the group consisting of halogen, hydroxy, and alkoxy.

For certain embodiments, $R_4$ is $C_{1-3}$ alkyl optionally substituted by hydroxy or one or more fluorine atoms.

For certain embodiments, $R_4$ is phenyl, benzyl, pyridinyl, or pyridinylmethyl, each of which is unsubstituted or substituted by one or more substituents selected from the group consisting of halogen, hydroxy, and alkoxy.

For certain embodiments, $R_4$ is selected from the group consisting of alkyl, alkenyl, alkynyl, aryl, heteroaryl, and heterocyclyl, each of which is unsubstituted or substituted by one or more substituents independently selected from the group consisting of alkyl, alkoxy, hydroxyalkyl, haloalkyl, halogen, hydroxy, aryl, heteroaryl, and heterocyclyl; and wherein when $R_4$ is heteroaryl, then the one or more substituents may also be independently selected from the group consisting of haloarylenyl, alkoxyarylenyl, alkylarylenyl, and arylalkylenyl; and wherein when $R_4$ is heterocyclyl, then the one or more substituents may also be independently selected from the group consisting of arylalkylenyl and aminocarbonyl.

For certain embodiments, $R_4$ is heterocyclyl which is selected from the group consisting of morpholinyl, thiomorpholinyl, piperidinyl, pyrrolidinyl, thiazolidinyl, dihydroisoquinolin-(1H)-yl, octahydroisoquinolin-(1H)-yl, 1,3-dioxolanyl, oxetanyl, tetrahydrofuranyl, tetrahydropyranyl, each of which is unsubstituted or substituted by one or more substituents independently selected from the group consisting of $C_{1-4}$ alkyl, hydroxy$C_{1-4}$ alkyl, hydroxy, aminocarbonyl, aryl$C_{1-4}$ alkylenyl, and 5 to 7 membered heterocyclyl containing one or two heteroatoms.

For certain embodiments, $R_4$ is heteroaryl which is selected from the group consisting of pyridyl, pyrazolyl, oxazolyl, and triazolyl, each of which is unsubstituted or substituted by one or more substituents independently selected from the group consisting of $C_{1-4}$ alkyl, hydroxy$C_{1-4}$ alkyl, halo$C_{1-4}$ alkyl, aryl, aryl substituted by fluoro, chloro, methyl, or methoxy, aryl$C_{1-4}$ alkylenyl, and heteroaryl. For certain embodiments, $R_4$ is alkyl, arylalkylenyl, aryl, or heteroaryl wherein arylalkylenyl, aryl, or heteroaryl are optionally substituted by alkyl.

For certain embodiments, $R_4$ is selected from the group consisting of $C_{1-4}$ alkyl, $C_{1-4}$ alkenyl, and $C_{1-4}$ alkynyl, each of which is unsubstituted or substituted by one or more substituents independently selected from the group consisting of hydroxy, halogen, and aryl.

For certain embodiments, $R_4$ is aryl which is unsubstituted or substituted by one or more substituents independently selected from the group consisting of halogen, hydroxy, $C_{1-4}$ alkoxy, $C_{1-4}$ alkyl, and hydroxy$C_{1-4}$ alkyl.

For certain embodiments, $R_4$ is alkyl, aryl, arylalkylenyl, or heteroaryl, wherein aryl, arylalkylenyl, and heteroaryl are optionally substituted by alkyl.

For certain embodiments, $R_4$ is hydrogen, alkyl, aryl, arylalkylenyl, heteroaryl, or heterocyclyl wherein alkyl, aryl, arylalkylenyl, heteroaryl, and heterocyclyl are unsubstituted or substituted by one or more substituents independently selected from the group consisting of hydroxy, halogen, alkoxy, alkyl, haloalkyl, and dialkylamino.

For certain embodiments, $R_4$ is hydrogen, alkyl, alkenyl, aryl, arylalkylenyl, heteroaryl, or heterocyclyl wherein alkyl, alkenyl, aryl, arylalkylenyl, heteroaryl, and heterocyclyl are unsubstituted or substituted by one or more substituents independently selected from the group consisting of hydroxy, halogen, alkoxy, alkyl, and haloalkyl.

For certain embodiments, $R_4$ is alkyl, aryl, arylalkylenyl, heteroaryl, or heterocyclyl wherein alkyl, aryl, arylalkylenyl, heteroaryl, and heterocyclyl are unsubstituted or substituted by one or more substituents independently selected from the group consisting of hydroxy, halogen, alkoxy, alkyl, haloalkyl, and dialkylamino.

For certain embodiments, $R_4$ is aryl which is unsubstituted or substituted by one or more substituents independently selected from the group consisting of alkyl, alkoxy, halogen, and dialkylamino.

For certain embodiments, $R_4$ is hydrogen, alkyl, or aryl which is unsubstituted or substituted by one or more substituents independently selected from the group consisting of alkyl, alkoxy, halogen, and dialkylamino.

For certain embodiments, $R_4$ is alkyl or aryl.

For certain embodiments, $R_4$ is alkyl.

For certain embodiments, $R_4$ is methyl.

For certain embodiments, $R_4$ is hydrogen.

For certain embodiments, $R_5$ is selected from the group consisting of:

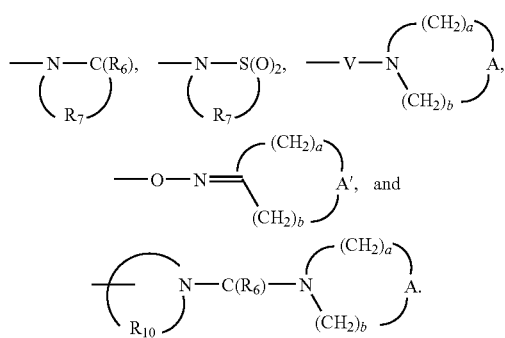

For certain embodiments, $R_5$ is selected from the group consisting of:

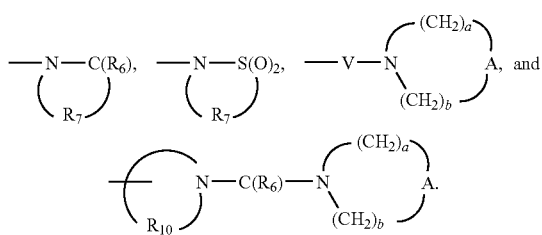

For certain embodiments, $R_5$ is selected from the group consisting of:

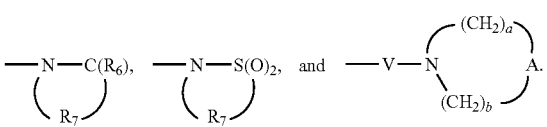

For certain embodiments, $R_5$ is

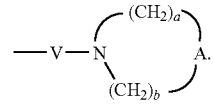

For certain of these embodiments, A is —$CH_2$—, —O—, or —N(-Q-$R_4$)—, and V is —C(O)—. For certain of these embodiments, A is —$CH_2$—, and V is —C(O)—. Alternatively, V is N($R_8$)—C($R_6$)—; A is —O—; a and b are each 2 or 3; and $R_8$ is hydrogen or $C_{1-4}$ alkyl.

For certain embodiments, $R_6$ is selected from the group consisting of =O and =S.

For certain embodiments, $R_6$ is =O.

For certain embodiments, $R_6$ is =S.

For certain embodiments, $R_7$ is $C_{2-7}$ alkylene.

For certain embodiments, $R_7$ is $C_{2-3}$ alkylene.

For certain embodiments, $R_7$ is propylene.

For certain embodiments, $R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl.

For certain embodiments, $R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl.

For certain embodiments, $R_8$ is independently selected from the group consisting of hydrogen, $C_{1-4}$ alkyl, hydroxy$C_{1-4}$ alkyl, and $C_{1-4}$ alkoxy$C_{1-4}$ alkyl.

For certain embodiments, $R_8$ is hydrogen, methyl, ethyl, 2-hydroxyethyl, or 2-methoxyethyl.

For certain embodiments, $R_8$ is hydrogen or $C_{1-4}$ alkyl.

For certain embodiments, $R_8$ is hydrogen or methyl.

For certain embodiments, $R_8$ is hydrogen.

For certain embodiments, $R_9$ is selected from the group consisting of hydrogen and alkyl.

For certain embodiments, $R_9$ is alkyl.

For certain embodiments, $R_9$ is hydrogen.

For certain embodiments, $R_{10}$ is $C_{3-8}$ alkylene.

For certain embodiments, $R_{10}$ is $C_{4-6}$ alkylene.

For certain embodiments, $R_{10}$ is pentylene.

For certain embodiments, A is selected from the group consisting of —$CH_2$—, —O—, —C(O)—, —S(O)$_{0-2}$—, and —N(-Q-$R_4$)—.

For certain embodiments, A is selected from the group consisting of —$CH_2$—, —O—, and —N(-Q-$R_4$)—.

For certain embodiments, A is —O—, —S—, or —SO$_2$—.

For certain embodiments, A is —O—.

For certain embodiments, A is —$CH_2$—.

For certain embodiments, A is —N(-Q-$R_4$)—.

For certain embodiments, A' is selected from the group consisting of —O—, —S(O)$_{0-2}$—, —N(-Q-$R_4$)—, and —$CH_2$—.

For certain embodiments, A' is selected from the group consisting of —O—.

For certain embodiments, Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—.

For certain embodiments, Q is a bond, —S(O)$_2$—, —C(O)—, —C(O)—O—, —C(O)—N($R_8$)—, —C(S)—N($R_8$)—, or —S(O)$_2$—N($R_8$)—.

For certain embodiments, Q is a bond, —C(O)—, —S(O)$_2$—, —S(O)$_2$—N($R_8$)—, —C(O)—N($R_8$)—, C(S)—N($R_8$)—, or —C(O)—O—.

For certain embodiments, Q is —C(O)—, —S(O)$_2$, —S(O)$_2$—N(R$_8$)—, or —C(O)—N(R$_8$)—.

For certain embodiments, Q is —C(R$_6$)—.

For certain embodiments, Q is —S(O)$_2$—.

For certain embodiments, Q is —C(R$_6$)—N(R$_8$)—W—.

For certain embodiments, Q is a bond.

For certain embodiments, Q$_1$ is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—

For certain embodiments, Q$_1$ is selected from the group consisting of a bond, —C(O)—, —S(O)$_2$, and —C(O)—NH—.

For certain embodiments, Q$_1$ is selected from the group consisting of —C(O)—, —S(O)$_2$, and —C(O)—NH—.

For certain embodiments, Q$_1$ is a bond.

For certain embodiments, Q$_2$ is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—; with the proviso that when Q$_2$ is a bond then R$_4$ is hydrogen, C$_{1-3}$ alkyl, or pyridin-3-ylmethyl.

For certain embodiments, Q$_2$ is selected from the group consisting of a bond, —C(O)—, —S(O)$_2$, and —C(O)—NH—.

For certain embodiments, Q$_2$ is selected from the group consisting of —C(O)—, —S(O)$_2$, and —C(O)—NH—.

For certain embodiments, Q$_2$ is a bond.

For certain embodiments, V is selected from the group consisting of —C(R$_6$)—, —O—C(R$_6$)—, —N(R$_8$)—C(R$_6$)—, and —S(O)$_2$—.

For certain embodiments, V is —C(R$_6$)—.

For certain embodiments, V is —C(O)—.

For certain embodiments, V is —N(R$_8$)—C(R$_6$)—.

For certain embodiments, V is —N(R$_8$)—C(O)—.

For certain embodiments, W is selected from the group consisting of a bond, —C(O)—, and —S(O)$_2$—.

For certain embodiments, W is a bond.

For certain embodiments, X$_1$ is selected from the group consisting of alkylene, alkenylene, and alkynylene, wherein the alkylene, alkenylene, and alkynylene are optionally interrupted by one or more —O— groups, and optionally substituted by a hydroxy or methoxy group; with the proviso that X$_1$ can also be a bond when R$_4$ is bonded to X$_1$; or Y is bonded to X$_1$ and Y is —C(R$_6$)—, —C(R$_6$)—O—, —C(R$_6$)—N(R$_8$)—, —C(R$_6$)—N(OR$_9$)—, —C(=N—O—R$_8$)—, —CH(—N(—O—R$_8$)-Q-R$_4$)—,

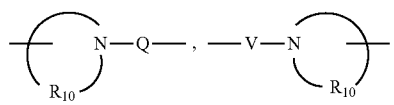

wherein V is —C(R$_6$)—, or

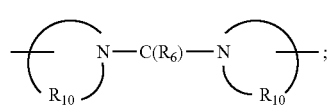

or R$_5$ is bonded to X$_1$ and R$_5$ is

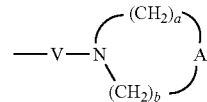

wherein V is —C(R$_6$)— or

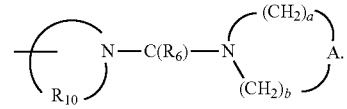

For certain embodiments, X$_1$ is selected from the group consisting of alkylene and alkenylene, wherein the alkylene and alkenylene are optionally interrupted by one or more —O— groups.

For certain embodiments, X$_1$ is alkylene.

For certain embodiments, X$_1$ is C$_{1-4}$ alkylene.

For certain embodiments, X$_1$ is C$_{1-3}$ alkylene optionally substituted by a hydroxy or methoxy group.

For certain embodiments, X$_1$ is —(CH$_2$)$_{1-3}$—.

For certain embodiments, X$_1$ is C$_{2-3}$ alkylene substituted by one hydroxy group.

For certain embodiments, X$_1$ is a bond, and R$_4$ is bonded to X$_1$.

For certain embodiments, X$_1$ is a bond, and the Y bonded to X$_1$ is —C(R$_6$)—, —C(R$_6$)—O—, —C(R$_6$)—N(R$_8$)—, —C(R$_6$)—N(OR$_9$)—, —C(=N—O—R$_8$)—, —CH(—N(—O—R$_8$)-Q-R$_4$)—,

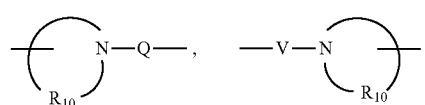

wherein V is —C(R$_6$)—, or

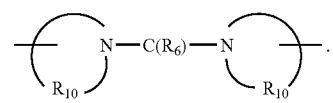

For certain embodiments, X$_1$ is a bond, R$_5$ is bonded to X$_1$, and R$_5$ is

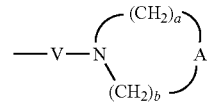

wherein V is —C(R$_6$)— or

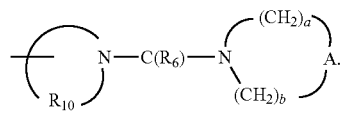

For certain embodiments, X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups.

For certain embodiments, X" is alkylene.

For certain embodiments, X" is $C_{1-3}$ alkylene or $C_{1-3}$ alkenylene.

For certain embodiments, X" is selected from the group consisting of $C_{1-3}$ alkylene, $C_{1-3}$ alkenylene, piperidin-1,4-diyl, and phenylene.

For certain embodiments, X" is selected from the group consisting of $C_{1-3}$ alkylene and phenylene.

For certain embodiments, X" is arylene.

For certain embodiments, Y is selected from the group consisting of —O—, —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—, —O—N(R$_8$)-Q-, —O—N=C(R$_4$)—, —C(=N—O—R$_8$)—, —CH(—N(—O—R$_8$)-Q-R$_4$)—,

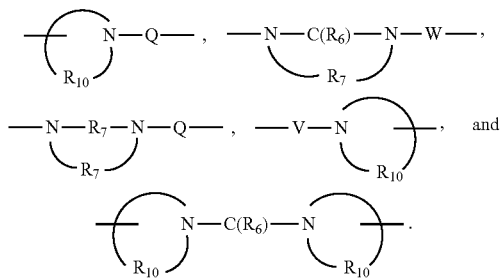

For certain embodiments, Y is —C(O)—, —S(O)$_2$—, —N(R$_8$)-Q-, or —C(O)—NH—.

For certain embodiments, Y is —S—, —S(O)$_2$—, or N(R$_8$)-Q-.

For certain embodiments, Y is —NH—S(O)$_2$—, —NH—C(O)—, —NH—S(O)$_2$—N(R$_8$)—, —NH—C(O)—N(R$_8$)—, —NH—C(S)—N(R$_8$)—, —NH—C(O)—O—, or —N(R$_8$)—.

For certain embodiments, Y is —S— or —S(O)$_2$—.

For certain embodiments, Y is —S(O)$_2$—.

For certain embodiments, Y is —C(O)—.

For certain embodiments, Y is —O—.

For certain embodiments, Y is

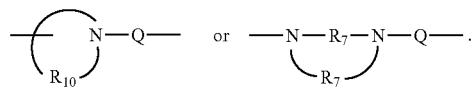

For certain embodiments, Y is

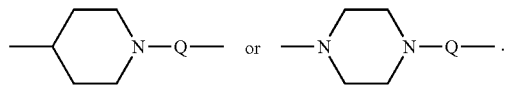

For certain embodiments, Y is

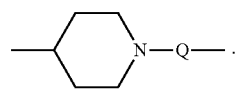

For certain embodiments, Y is

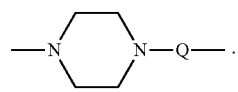

For certain embodiments, Z' is a bond or —O—.

For certain embodiments, Z' is a bond.

For certain embodiments, Z' is —O—.

For certain embodiments, a and b are independently integers from 1 to 6 with the proviso that a+b is $\leq 7$.

For certain embodiments, a and b are each 2 or 3.

For certain embodiments, a and b are each 2.

For certain embodiments, m is 0 or 1.

For certain embodiments, m is 0.

For certain embodiments, m is 1.

For certain embodiments, p is an integer from 0 to 4.

For certain embodiments, p is 0 or 1.

For certain embodiments, p is 0.

For certain embodiments, p is 1.

For certain embodiments, p is 2.

For certain embodiments, p is 3 or 4.

For certain embodiments, q is an integer from 0 to 3.

For certain embodiments, q is 0 or 1.

For certain embodiments, q is 0.

For certain embodiments, q is 1.

For certain embodiments, m is 1 and p is 0.

For certain embodiments, m is 0 and p is 0.

For certain embodiments, m is 1 and q is 0.

For certain embodiments, m is 0 and q is 0.

For certain embodiments of the compounds of Formulas I, II, III, or IV, or any one of the above embodiments of these Formulas, the —NH$_2$ group can be replaced by an —NH-G group, as shown in the compounds of Formula V, to form prodrugs. In such embodiments, G is selected from the group consisting of —C(O)—R', α-aminoacyl, α-aminoacyl-α-aminoacyl, —C(O)—O—R', —C(O)—N(R")R', —C(=NY')—R', —CH(OH)—C(O)—OY', —CH(OC$_{1-4}$ alkyl)Y$_0$, —CH$_2$Y$_1$, and —CH(CH$_3$)Y$_1$. For certain embodiments, G is selected from the group consisting of —C(O)—R', α-aminoacyl, α-aminoacyl-α-aminoacyl, and —C(O)—O—R'. Preferably, R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, halo$C_{1-4}$ alkylenyl, halo$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen. Preferably, α-aminoacyl is an acyl group derived from an α-amino acid selected from the group consisting of racemic, D-, and L-amino acids. Preferably, Y' is selected from the group consisting of hydrogen, $C_{1-6}$ alkyl, and benzyl. Preferably, $Y_0$ is selected from the group consisting of $C_{1-6}$ alkyl, carboxy$C_{1-6}$ alkylenyl, amino$C_{1-4}$ alkylenyl, mono-N—$C_{1-6}$ alkylamino$C_{1-4}$ alkylenyl, and di-N,N—$C_{1-6}$ alkylamino$C_{1-4}$ alkylenyl. Preferably, $Y_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl.

For certain embodiments, including any one of the above embodiments of Formula V, G is selected from the group consisting of —C(O)—R', α-aminoacyl, and —C(O)—O—R'.

For certain embodiments, including any one of the above embodiments of Formula V, G is selected from the group consisting of —C(O)—R', α-amino-$C_{2-11}$ acyl, and —C(O)—O—R'. α-Amino-$C_{2-11}$ acyl includes α-amino acids containing a total of at least 2 carbon atoms and a total of up to 11 carbon atoms, and may also include one or more heteroatoms selected from the group consisting of O, S, and N.

In some embodiments, the present invention provides a pharmaceutical composition comprising a therapeutically effective amount of a compound or salt of any one of Formulas I, II, III, IV, or V, or any one of the above embodiments and a pharmaceutically acceptable carrier.

In some embodiments, the present invention provides a method of inducing cytokine biosynthesis in an animal comprising administering an effective amount of a compound or salt of any one of Formulas I, II, III, IV, or V, or any one of the above embodiments of these Formulas or administering any one of the above pharmaceutical compositions containing a compound or salt of any one of Formulas I, II, III, IV, or V, or any one of the above embodiments of these Formulas to the animal. For certain of these embodiments, the cytokine is selected from the group consisting of IFN-α, TNF-α, IL-6, IL-10, and IL-12. For certain of these embodiments, the cytokine is IFN-α or TNF-α. For certain of these embodiments, the cytokine is IFN-α.

In some embodiments, the present invention provides a method of treating a viral disease in an animal in need thereof comprising administering a therapeutically effective amount of a compound or salt of any one of Formulas I, II, III, IV, or V, or any one of the above embodiments of these Formulas or administering any one of the above pharmaceutical compositions containing a compound or salt of any one of Formulas I, II, III, IV, or V, or any one of the above embodiments of these Formulas to the animal.

In some embodiments, the present invention provides a method of treating a neoplastic disease in an animal in need thereof comprising administering a therapeutically effective amount of a compound or salt of any one of Formulas I, II, III, IV, or V, or any one of the above embodiments of these Formulas or administering any one of the above pharmaceutical compositions containing a compound or salt of any one of Formulas I, II, III, IV, or V, or any one of the above embodiments of these Formulas to the animal.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v. 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

In some embodiments, compounds of the invention can be prepared according to Reaction Scheme I wherein R and Z are as defined above, Bn is benzyl, E is carbon (imidazoquinolines) or nitrogen (imidazonaphthyridines), Hal is chloro or bromo, and t is an integer from 0 to 4 when E is carbon, or when E is nitrogen, then t is an integer from 0 to 3.

In step (1) of Reaction Scheme I, a 4-chloroquinolin-3-amine or 4-chloro[1,5]naphthyridin-3-amine of Formula XX is reacted with an acid halide of Formula Hal-Z—CH$_2$—C(O)—Hal to provide an N-(4-chloroquinolin-3-yl)amide or N-(4-chloro[1,5]naphthyridin-3-yl)amide of Formula XXI. The reaction can be carried out by heating a solution of a compound of Formula XX and the acid halide in a suitable solvent such as 1,2-dichloroethane. Some acid chlorides of Formula Hal-Z—CH$_2$—C(O)—Hal are commercially available; others can be prepared using conventional synthetic methods. Some 4-chloroquinolin-3-amines and 4-chloro[1,5]naphthyridin-3-amines of Formula XX are known. Others can be prepared using conventional synthetic methods; for example, by reduction of known 4-chloro-3-nitroquinolines and 4-chloro-3-nitro[1,5]naphthyridines.

In step (2) of Reaction Scheme I, an N-(4-chloroquinolin-3-yl)amide or N-(4-chloro[1,5]naphthyridin-3-yl)amide of Formula XXI is reacted with O-benzylhydroxylamine hydrochloride to provide a benzyloxy substituted 1H-imidazo[4,5-c]quinoline or 1H-imidazo[4,5-c][1,5]naphthyridine of Formula XXII. The reaction can be carried out by combining a compound of Formula XXI and O-benzylhydroxylamine hydrochloride in an alcoholic solvent, such as isopropanol, and heating the resulting mixture.

In step (3) of Reaction Scheme I, the benzyl group of a 1H-imidazo[4,5-c]quinoline or 1H-imidazo[4,5-c][1,5]naphthyridine of Formula XXII is cleaved under acidic conditions to provide a 1H-imidazo[4,5-c]quinolin-1-ol or 1H-imidazo[4,5-c][1,5]naphthyridin-1-ol of Formula XXIII. The cleavage can be carried out by treating a solution of a compound of Formula XXII in a suitable solvent such as dichloromethane with boron tribromide. The reaction can be carried out at ambient temperature.

Alternatively, the cyclization in step (2) and the subsequent cleavage of the benzyl group can be carried out as a one-pot procedure without isolating the compound of Formula XXII. This can be accomplished, for example, by increasing the reaction time and/or reaction temperature of step (2). Alternatively, step (2) can be carried out for a time sufficient to form the benzyloxy compound of Formula XXII and then an acid, such as, for example, pyridinium p-toluenesulfonate can be added and heating continued for a time sufficient to cleave the benzyl group.

In step (4) of Reaction Scheme I, a 1H-imidazo[4,5-c]quinolin-1-ol or 1H-imidazo[4,5-c][1,5]naphthyridin-1-ol of Formula XXIII is cyclized by an intramolecular displacement of the halogen under basic conditions to provide 1H-imidazo[4,5-c]quinoline or 1H-imidazo[4,5-c][1,5]naphthyridine of Formula XXIV. The reaction can be carried out by adding a base such as potassium tert-butoxide or sodium hydride to a solution of a compound of Formula XXXIII in a suitable solvent such as tetrahydrofuran or N,N-dimethylformamide. The reaction can be carried out at ambient temperature. Alternatively, a solution of a compound of Formula XXXIII in a suitable solvent such as dichloromethane can be treated with an aqueous solution of a base such as potassium carbonate or sodium carbonate. The reaction can be carried out at ambient temperature.

Alternatively, the cleavage of the benzyl group and the subsequent cyclization of step (4) can be carried out as a one-pot procedure without isolating the compound of Formula XXIII by treating a solution of a compound of Formula XXII in dichloromethane with boron tribromide and then adding an aqueous solution of a base such as potassium carbonate or sodium carbonate.

In step (5) of Reaction Scheme I, a 1H-imidazo[4,5-c]quinoline or 1H-imidazo[4,5-c][1,5]naphthyridine of Formula XXIV is oxidized to provide a 1H-imidazo[4,5-c]quinoline-5N-oxide or 1H-imidazo[4,5-c][1,5]naphthyridine-5N-oxide of Formula XXV using a conventional oxidizing agent capable of forming N-oxides. The reaction can be carried out by adding 3-chloroperoxybenzoic acid to a solution of a compound of Formula XXIV in a solvent such as chloroform or dichloromethane. The reaction can be carried out at ambient temperature.

In step (6) of Reaction Scheme I, a 1H-imidazo[4,5-c]quinoline-5N-oxide or 1H-imidazo[4,5-c][1,5]naphthyridine-5N-oxide of Formula XXV is aminated to provide a 1H-imidazo[4,5-c]quinolin-6-amine or 1H-imidazo[4,5-c][1,5]naphthyridin-6-amine of Formula XXVI, a subgenus of Formula I. Step (6) involves the activation of an N-oxide of Formula XXV by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction can be carried out by adding ammonium hydroxide to a solution of the N-oxide of Formula XXV in a suitable solvent such as dichloromethane or chloroform and then adding p-toluenesulfonyl chloride. The reaction can be carried out at ambient temperature.

Alternatively, the oxidation and amination can be carried out as a one-pot procedure without isolating the N-oxide of Formula XXV by adding 3-chloroperoxybenzoic acid to a solution of a compound of Formula XXIV in a solvent such as dichloromethane or chloroform and then adding ammonium hydroxide and p-toluenesulfonyl chloride.

The amination reaction in step (6) of Reaction Scheme I can alternatively be carried out by treating a 5N-oxide of Formula XXV with trichloroacetyl isocyanate followed by hydrolysis of the resulting intermediate to provide a compound of Formula XXVI. The reaction can be carried out in two steps by (i) adding trichloroacetyl isocyanate to a solution of a 5N-oxide of Formula XXV in a solvent such as dichloromethane and stirring at ambient temperature to provide an isolable amide intermediate. In step (ii), a solution of the intermediate in methanol is treated with a base such as sodium methoxide or ammonium hydroxide at ambient temperature.

When Z is —(CH$_2$)$_c$—CH(R$_2$)—(CH$_2$)$_d$—, a racemic mixture may be obtained. A racemic mixture thus prepared can be resolved by methods known to one skilled in the art, for example, by reacting the racemic mixture with an enantiomerically pure sulfonic acid or carboxylic acid and selectively crystallizing a salt of one of the enantiomers from the mixture.

Reaction Scheme I

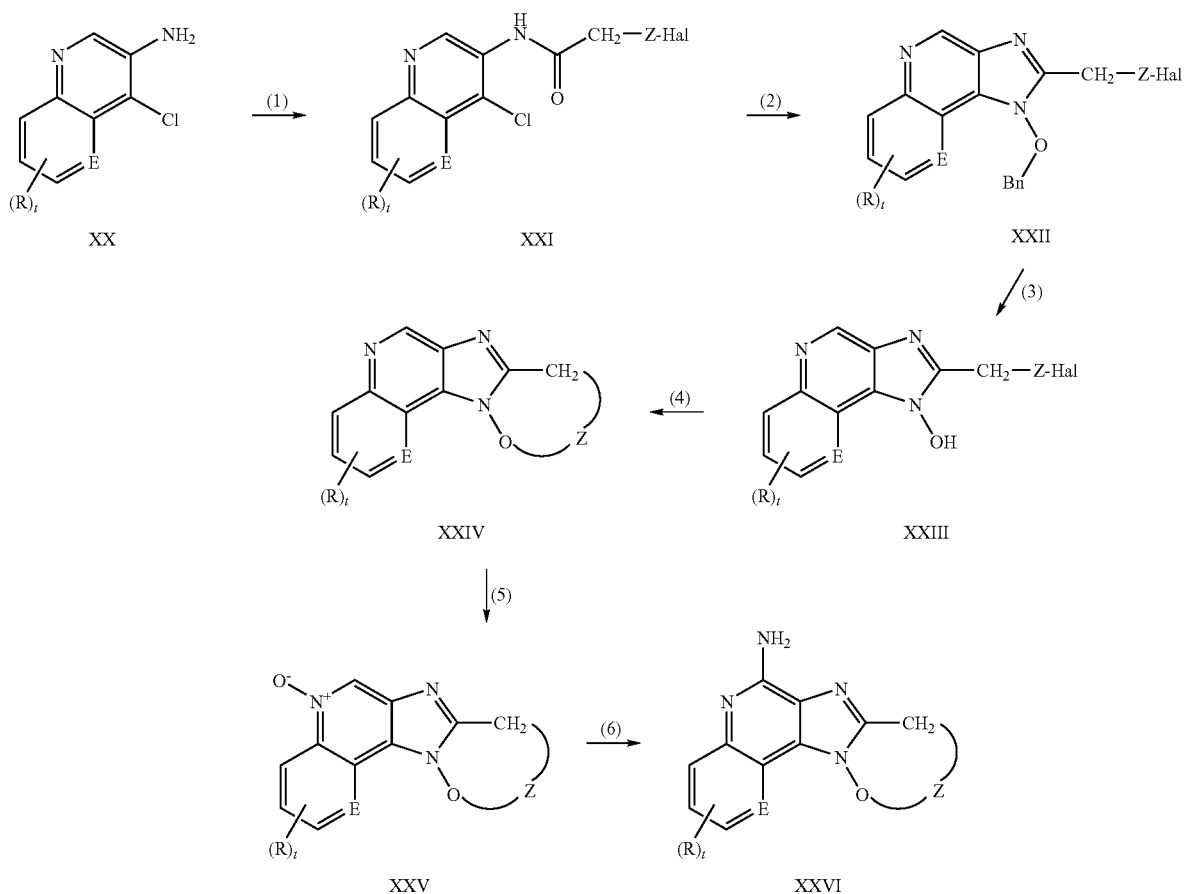

In some embodiments, compounds of the invention can be according to Reaction Scheme II wherein E, R, Z, and t are as defined above, Boc is tert-butoxycarbonyl, and $R_{1a}$ is $-X_1-R_4$ wherein $X_1$ and $R_4$ are as defined above.

In step (1) of Reaction Scheme II, a 4-chloro-3-nitroquinoline or 4-chloro-3-nitro[1,5]naphthyridine of Formula XXVII is treated with a diamine of the Formula $H_2N-CH(R_{1a})-Z-NH_2$ to provide a compound of Formula XXVIII. The reaction can be carried out by adding the diamine to a solution of a 4-chloro-3-nitroquinoline or 4-chloro-3-nitro[1,5]naphthyridine of Formula XXVII in a suitable solvent such as dichloromethane. The reaction can be carried out at ambient temperature or at a sub-ambient temperature such as, for example, 0° C. Many compounds of Formula XXVII are known or can be prepared using known synthetic methods, see for example, U.S. Pat. Nos. 4,689,338; 5,175,296; 5,367,076; 5,389,640; 6,194,425; and U.S. Patent Publication Application No. US 2004/0147543 and the documents cited therein. Some diamines of Formula $H_2N-CH(R_{1a})-Z-NH_2$ are commercially available; others can be prepared using known synthetic methods.

In step (2) of Reaction Scheme II, the amino group on a 4-chloro-3-nitroquinoline or 4-chloro-3-nitro[1,5]naphthyridine of Formula XXVIII is protected with a Boc group using conventional methods. For example, the protection can be carried out by treating a solution or suspension of compound of Formula XXVIII in a suitable solvent such as tetrahydrofuran with di-tert-butyl dicarbonate in the presence of a base such as sodium hydroxide. The reaction can be carried out at ambient temperature.

Alternatively, a diamine of the Formula $H_2N-CH(R_{1a})-Z-NH_2$ can be protected prior to being reacted with a 4-chloro-3-nitroquinoline or 4-chloro-3-nitro[1,5]naphthyridine of Formula XXVII. The protection can be carried out by treating a diamine such as (S)-(−)-1,2-diaminopropane dihydrochloride with one equivalent of di-tert-butyl dicarbonate in the presence of a base such as 1,8-diazabicyclo[5.4.0]undec-7-ene (DBU). The protection reaction can be carried out at a sub-ambient temperature such as 0° C. and allowed to warm to ambient temperature.

In step (3) of Reaction Scheme II, a 3-nitroquinolin-4-amine or 3-nitro[1,5]naphthyridin-4-amine of Formula XXIX is reduced to provide a quinoline-3,4-diamine or [1,5]naphthyridine-3,4-diamine of Formula XXX. The reaction can be carried out by hydrogenation using a heterogeneous hydrogenation catalyst such as platinum on carbon. The hydrogenation is conveniently carried out in a Parr apparatus in a suitable solvent such as toluene, methanol, isopropanol, ethyl acetate, or acetonitrile. The reaction can be carried out at ambient temperature.

In step (4) of Reaction Scheme II, a quinoline-3,4-diamine or [1,5]naphthyridine-3,4-diamine of Formula XXX is cyclized to provide a 1,3-dihydro-1H-imidazo[4,5-c]quinoline-2-thione or 1,3-dihydro-1H-imidazo[4,5-c][1,5]naphthyridine-2-thione of Formula XXXI. The cyclization can be carried out by combining a compound of Formula XXX with 1,1'-thiocarbonyldiimidazole in a suitable solvent such as tetrahydrofuran (THF), tert-butyl methyl ether, dichloromethane, or N,N-dimethylformamide (DMF). Optionally, the reaction can be carried out in the presence of excess base such as pyridine. The reaction may be carried out at ambient temperature or at an elevated temperature such as 90° C. to 120° C. or the reflux temperature of the solvent.

In step (5) of Reaction Scheme II, a 1,3-dihydro-1H-imidazo[4,5-c]quinoline-2-thione or 1,3-dihydro-3H-imidazo[4,5-c][1,5]naphthyridine-2-thione of Formula XXXI is methylated to provide a 2-(methylthio)-1H-imidazo[4,5-c]quinoline or a 2-(methylthio)-1H-imidazo[4,5-c][1,5]naphthyridine of Formula XXXII. The reaction can be carried out by combining a compound of Formula XXXI with iodomethane in a suitable solvent or solvent mixture, such as ethanol/water, in the presence of a base, such as ammonium hydroxide or sodium methoxide. The reaction can be carried out at ambient temperature.

In step (6) of Reaction Scheme II, a 2-(methylthio)-1H-imidazo[4,5-c]quinoline or a 2-(methylthio)-1H-imidazo[4,5-c][1,5]naphthyridine of Formula XXXII is oxidized to a 2-(methylsulfonyl)-1H-imidazo[4,5-c]quinoline or a 2-(methylsulfonyl)-1H-imidazo[4,5-c][1,5]naphthyridine of Formula XXXIII using a conventional oxidizing agent. The oxidation can be carried out, for example, by combining acetic acid and potassium permanganate with a compound of Formula XXXII at ambient temperature. The reaction may be carried out in a suitable solvent such as water.

In step (7) of Reaction Scheme II, a 2-(methylsulfonyl)-1H-imidazo[4,5-c]quinoline or a 2-(methylsulfonyl)-1H-imidazo[4,5-c][1,5]naphthyridine of Formula XXXIII is treated with acid to effect removal of the Boc group and intramolecular displacement of the methylsulfonyl group by the amino group to provide a compound of Formula XXXIV. The reaction can be carried out by dissolving a compound of Formula XXXIII in trifluoroacetic acid and stirring the resulting solution at ambient temperature.

Alternatively, step (7) may be carried out under basic conditions, for example, by using an alkoxide base. The reaction can be conveniently carried out by combining a compound of Formula XXXIII with sodium ethoxide in a suitable solvent such as ethanol and heating, for example, at the reflux temperature of the solvent. Alternatively, a compound of Formula XXXIII may be combined with potassium tert-butoxide in a suitable solvent such as THF; the reaction may be carried out at room temperature or at an elevated temperature, such as the reflux temperature of the solvent. When potassium tert-butoxide is used to effect the cyclization at room temperature, the Boc group may be conserved, and a compound of Formula XXXV, wherein -$Q_2$-$R_4$ is —C(O)—O—C($CH_3$)$_3$, may be isolated.

In step (8) of Reaction Scheme II, the secondary amine of a compound of Formula XXXIV or a salt thereof is converted to an amide, sulfonamide, sulfamide, urea, or tertiary amine of Formula XXXV using conventional methods. For example, a compound of Formula XXXIV or a salt thereof can react with an acid chloride of Formula $R_4$C(O)Cl to provide a compound of Formula XXXV in which $Q_2$ is —C(O)—. In addition, a compound of Formula XXXIV can react with sulfonyl chloride of Formula $R_4$S(O)$_2$Cl or a sulfonic anhydride of Formula ($R_4$S(O)$_2$)$_2$O to provide a compound of Formula XXXV in which $Q_2$ is —S(O)$_2$—. Numerous acid chlorides of Formula $R_4$C(O)Cl, sulfonyl chlorides of Formula $R_4$S(O)$_2$Cl, and sulfonic anhydrides of Formula ($R_4$S(O)$_2$)$_2$O are commercially available; others can be readily prepared using known synthetic methods. The reaction can be carried out by adding the acid chloride of Formula $R_4$C(O)Cl, sulfonyl chloride of Formula $R_4$S(O)$_2$Cl, or sulfonic anhydride of Formula ($R_4$S(O)$_2$)$_2$O to a solution of the compound of Formula XXXIV in a suitable solvent such as chloroform, dichloromethane, N,N-dimethylacetamide (DMA), or N,N-dimethylformamide (DMF). Optionally a base such as triethylamine or N,N-diisopropylethylamine can be added. The reaction can be carried out at ambient temperature or at a sub-ambient temperature such as 0° C.

Ureas of Formula XXXV, where $Q_2$ is —C(O)—NH— can be prepared by reacting a compound of Formula XXXIV or a salt thereof with isocyanates of Formula $R_4$N=C=O. Numerous isocyanates of Formula $R_4$N=C=O are commercially available; others can be readily prepared using known synthetic methods. The reaction can be carried out by adding the isocyanate of Formula $R_4$N=C=O to a solution of the compound of Formula XXXIV in a suitable solvent such as DMA, DMF, or chloroform. Optionally a base such as triethylamine or N,N-diisopropylethylamine can be added. The reaction can be carried out at ambient temperature or a sub-ambient temperature such as 0° C. Alternatively, a compound of Formula XXXIV can be treated with an isocyanate of Formula $R_4$(CO)N=C=O, a thioisocyanate of Formula $R_4$N=C=S, a sulfonyl isocyanate of Formula $R_4$S(O)$_2$N=C=O, or a carbamoyl chloride of Formula $R_4$N—($R_8$)—C(O)Cl to provide a compound of Formula XXXV, where $Q_2$ is —C(O)—N($R_8$)—(CO)—, —C(S)—N($R_8$)—, —C(O)—N($R_8$)—S(O)$_2$—, or —C(O)—N($R_8$)—, respectively. Alternatively, a compound of Formula XXXIV can be treated with a carbamoyl chloride of Formula Cl—C(O)-heterocyclyl, wherein heterocyclyl is attached at a nitrogen atom, to provide a compound of Formula XXXV, wherein $Q_2$ is —C(O)— and $R_4$ is heterocyclyl attached at a nitrogen atom.

Sulfamides of Formula XXXV, where $Q_2$ is —S(O)$_2$—N($R_8$)—, can be prepared by reacting a compound or salt of Formula XXXIV with sulfuryl chloride to generate a sulfamoyl chloride in situ, and then reacting the sulfamoyl chloride with an amine of Formula HN($R_8$)$R_4$. Alternatively, sulfamides of Formula XXXV can be prepared by reacting a compound of Formula XXXIV with a sulfamoyl chloride of Formula $R_4$($R_8$)N—S(O)$_2$Cl. Many sulfonyl chlorides of Formula $R_4$S(O)$_2$Cl and amines of Formula HN($R_8$)$R_4$, and some sulfamoyl chlorides of Formula $R_4$($R_8$)N—S(O)$_2$Cl are commercially available; others can be prepared using known synthetic methods.

Compounds of Formula XXXV where $Q_2$ is a bond can be prepared by reductive alkylation of the secondary amine of compound of Formula XXXIV. The alkylation can be carried out in two parts by (i) adding an aldehyde or ketone to a solution of a compound of Formula XXXIV or a salt thereof in a suitable solvent such as DMF, THF, or methanol in the presence of a base such as N,N-diisopropylethylamine. In part (ii) the reduction is carried out by adding a suitable reducing agent such as the borane-pyridine complex. Both part (i) and part (ii) can be carried out at ambient temperature.

In steps (9) and (10) of Reaction Scheme II, a 1H-imidazo[4,5-c]quinoline or 1H-imidazo[4,5-c][1,5]naphthyridine of Formula XXXV is oxidized and then aminated to provide a 1H-imidazo[4,5-c]quinolin-6-amine or 1H-imidazo[4,5-c][1,5]naphthyridin-6-amine of Formula XXXVII, a subgenus of Formula I. The steps can be carried out using the methods described in steps (5) and (6) of Reaction Scheme I.

Alternatively, step (8) can be carried out after steps (9) and (10). In another alternative, step (8) can provide a compound of Formula XXXV wherein -$Q_2$-$R_4$ is —C(O)—O—C($CH_3$)$_3$ (Boc) using the method of step (2) of Reaction Scheme II. The Boc group can be removed under acidic conditions after the oxidation and amination of steps (9) and (10), and the resulting compound can be treated according to one of the methods described in step (8) of Reaction Scheme II to provide a compound of Formula XXXVII.

Other suitable amine protecting groups (e.g., a benzyloxycarbonyl group) may be used in Reaction Scheme II. When a benzyloxycarbonyl protecting group is used, the reduction in step (3) of Reaction Scheme II may be carried out by alternative methods. For example, the reduction can be carried out using sodium borohydride in the presence of nickel (II) chloride.

When the diamine of the Formula $H_2N$—$CH(R_{1a})$—$Z$—$NH_2$ that is used in step (1) is racemic, the compounds of Formulas XXXIV, XXXV, XXXVI, and XXXVII may be obtained as a racemic mixture. A racemic mixture thus prepared can be resolved by methods known to one skilled in the art, for example, by reacting the racemic mixture with an enantiomerically pure sulfonic acid or carboxylic acid and selectively crystallizing a salt of one of the enantiomers from the mixture. Alternatively, a diamine containing a single enantiomer may be used.

Reaction Scheme II

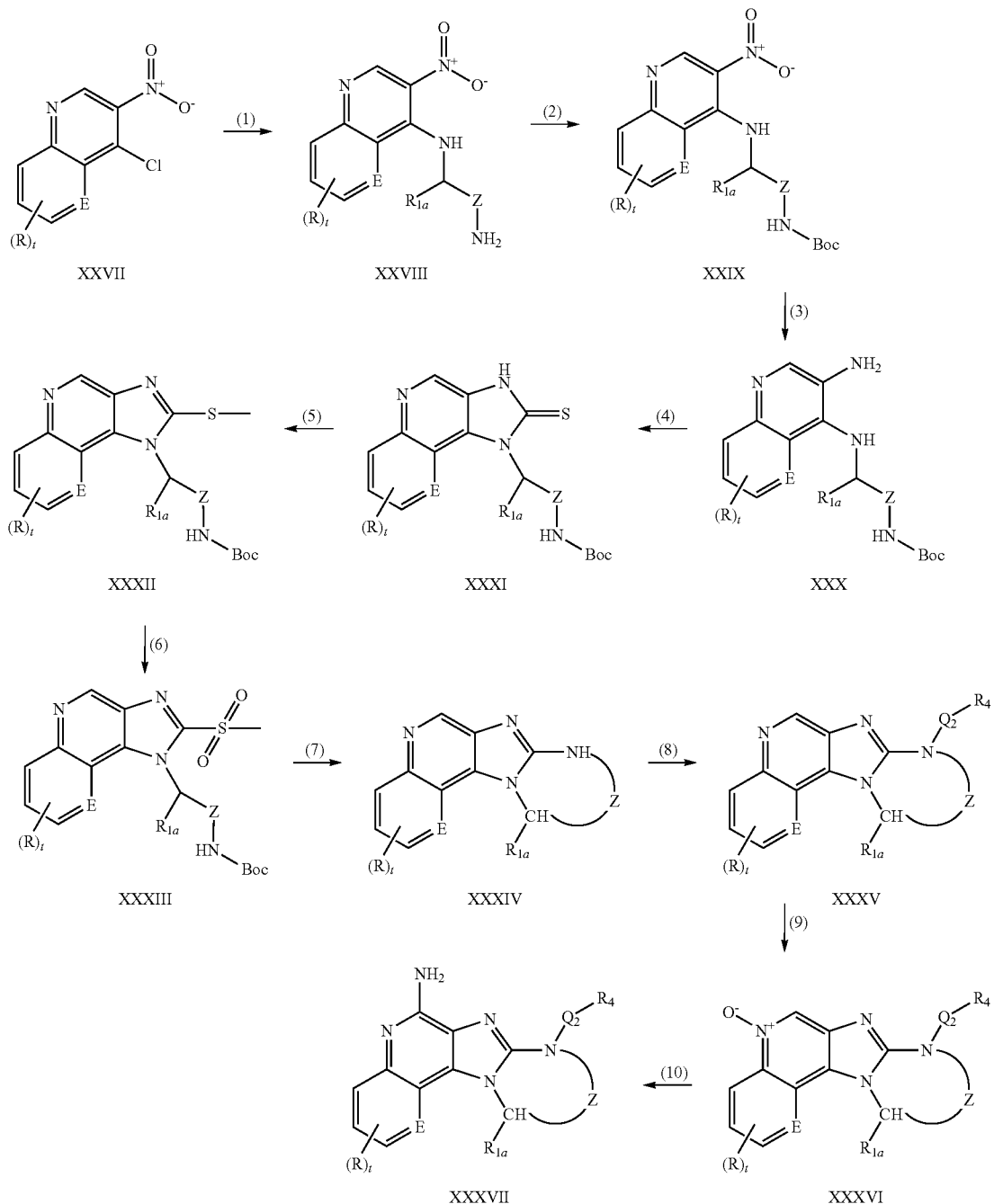

In some embodiments, compounds of the invention can be prepared according to Reaction Scheme III wherein Boc, E, $Q_1$, R, $R_{2a}$, $R_4$, and t are as defined above.

In step (1) of Reaction III, a tert-butyl N'-(3-nitroquinolin-4-yl)hydrazinecarboxylate or a tert-butyl N'-(3-nitro[1,5]naphthyridin-4-yl)hydrazinecarboxylate of Formula XXXVIII is reduced to provide a tert-butyl N'-(3-aminoquinolin-4-yl)hydrazinecarboxylate or a tert-butyl N'-(3-amino[1,5]naphthyridin-4-yl)hydrazinecarboxylate of Formula XXXIX. The reduction can be carried out using the method described in step (3) of Reaction Scheme II. Some compounds of Formula XXXVIII are known; others can be prepared using conventional synthetic methods. See, for example, United States Patent Application Publication US 2004/0176367 (Griesgraber) and International Publication No. WO/2006/026760 (Stoermer et al.) and the references cited therein.

In step (2) of Reaction Scheme III, a tert-butyl N'-(3-aminoquinolin-4-yl)hydrazinecarboxylate or a tert-butyl N'-(3-amino[1,5]naphthyridin-4-yl)hydrazinecarboxylate of Formula XXXIX is reacted with a ketal of Formula XL to provide a compound of Formula XLI. The reaction can be carried out by adding a solution of a ketal of Formula XL in a suitable solvent such as pyridine to a solution or suspension of a compound of Formula XXXIX, 1-[3-(dimethylamino)propyl]-3-ethylcarbodiimide hydrochloride, and 4-methylmorpholine in a suitable solvent such as pyridine in the presence of a base such as 4-dimethylaminopyridine. The reaction can be carried out at a sub-ambient temperature such as, for example, 0° C., and allowed to warm to ambient temperature. Some ketals of Formula XL are known. Others can be prepared using conventional synthetic methods; for example, a keto acid ester of the Formula alkyl-OC(O)—(CH$_2$)$_2$—C(O)—R$_{2a}$ wherein alkyl is a C$_{1-4}$ alkyl group can be converted to the ketal using conventional methods followed by hydrolysis of the ester group to the acid.

In step (3) of Reaction Scheme III, a compound of Formula XLI under goes two acid catalyzed cyclizations to provide a pyridazino[1',6':1,2]imidazo[4,5-c]quinoline or a pyridazino[1',6':1,2]imidazo[4,5-c][1,5]naphthyridine of Formula XLII. The cyclizations can be carried out in a one-pot two step procedure by (i) heating a solution of a compound of Formula XLI in a suitable solvent such as n-butanol in the presence of an acid such as pyridinium para-toluenesulfonate to form the imidazole ring and (ii) adding a stronger acid such as hydrochloric acid to hydrolyze the ketal and Boc groups and form the pyridazino ring. Optionally, the bulk of the n-butanol can be removed prior to the second step.

In step (4) of Reaction Scheme III, the imine bond in a pyridazino[1',6':1,2]imidazo[4,5-c]quinoline or a pyridazino[1',6':1,2]imidazo[4,5-c][1,5]naphthyridine of Formula XLII is reduced to provide a pyridazino[1',6':1,2]imidazo[4,5-c]quinoline or a pyridazino[1',6':1,2]imidazo[4,5-c][1,5]naphthyridine of Formula XLIII. The reduction can be carried out by treating a solution of a compound of Formula XLII in a suitable solvent such as methanol with sodium borohydride. The reaction can be carried out at a sub-ambient temperature such as, for example, 0° C., and allowed to warm to ambient temperature.

In step (5) of Reaction Scheme III, the secondary amine of a compound of Formula LXIII or a salt thereof is converted to an amide, sulfonamide, sulfamide, urea, or tertiary amine of Formula XLIV using conventional methods. The reactions can be carried out using the methods described in step (8) of Reaction Scheme II.

In steps (6) and (7) of Reaction Scheme III, a pyridazino[1',6':1,2]imidazo[4,5-c]quinoline or pyridazino[1',6':1,2]imidazo[4,5-c][1,5]naphthyridine of Formula XLIV is oxidized and then aminated to provide a pyridazino[1',6':1,2]imidazo[4,5-c]quinolin-6-amine or pyridazino[1',6':1,2]imidazo[4,5-c][1,5]naphthyridin-6-amine of Formula XLV, a subgenus of Formula I. The steps can be carried out using the methods described in steps (5) and (6) of Reaction Scheme I.

Alternatively, step (5) can be carried out after steps (6) and (7).

Reaction Scheme III

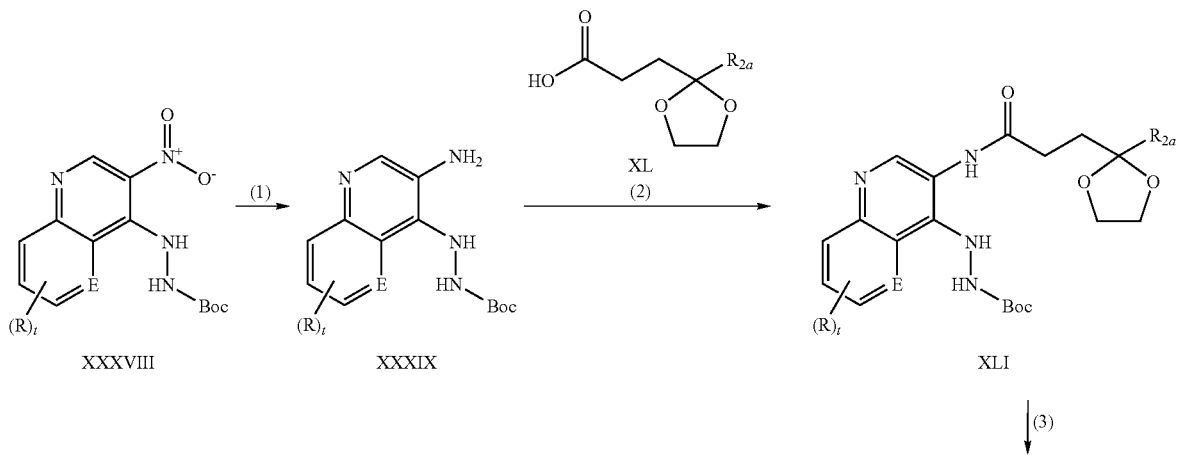

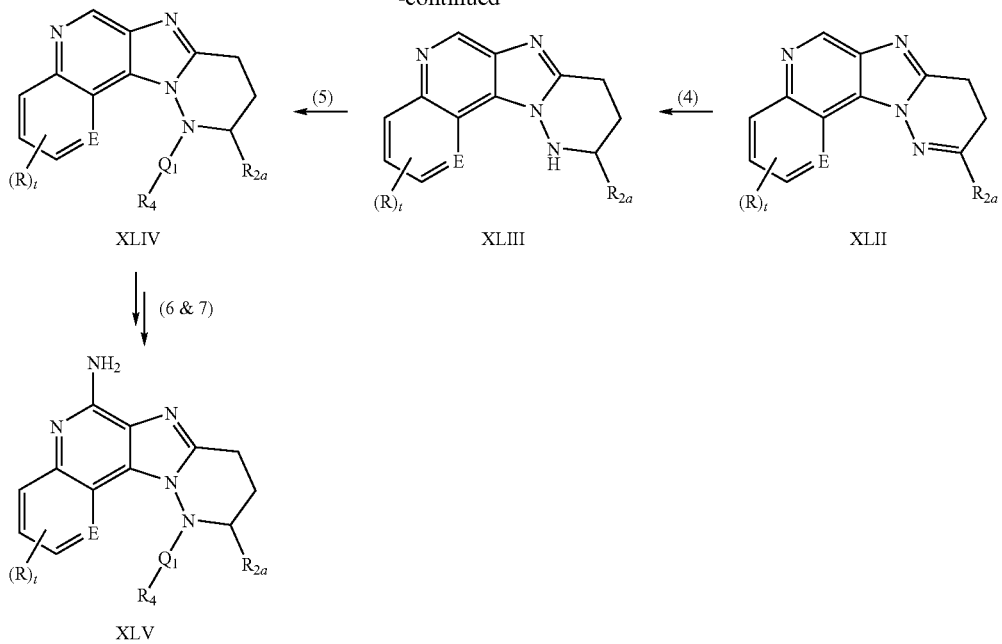

In some embodiments, compounds of the invention can be prepared according to Reaction Scheme IV wherein E, R, $R_{1a}$, Z, and t are as defined above.

In step (1) of Reaction Scheme IV, a 4-chloro-3-nitroquinoline or 4-chloro-3-nitro[1,5]naphthyridine of Formula XXVII is treated with an amino alcohol of the Formula $H_2N$—$CH(R_{1a})$—Z—OH to provide a compound of Formula XLVI. The reaction can be carried out by adding the amino alcohol to a solution of a 4-chloro-3-nitroquinoline or 4-chloro-3-nitro[1,5]naphthyridine of Formula XXVII in a suitable solvent such as DMF in the presence of a base such as triethylamine. The reaction can be carried out at ambient temperature or at a sub-ambient temperature such as, for example, 0° C.

In step (2) of Reaction Scheme IV, the hydroxy group on a 3-nitroquinolin-4-amine or 3-nitro[1,5]naphthyridin-4-amine of Formula XLVI is protected with an acetyl group using conventional methods. For example, the protection can be carried out by treating a solution of a compound of Formula XLVI in a suitable solvent such as dichloromethane with acetyl chloride in the presence of a base such as triethylamine.

In step (3) of Reaction Scheme IV, a 3-nitroquinolin-4-amine or 3-nitro[1,5]naphthyridin-4-amine of Formula XLVII is reduced to provide a quinoline-3,4-diamine or [1,5]naphthyridine-3,4-diamine of Formula XLVIII. The reaction can be carried out using the method described in step (3) of Reaction Scheme II.

In step (4) of Reaction Scheme IV, a quinoline-3,4-diamine or [1,5]naphthyridine-3,4-diamine of Formula XLVIII is cyclized to provide a 1,3-dihydro-1H-imidazo[4,5-c]quinoline-2-thione or 1,3-dihydro-1H-imidazo[4,5-c][1,5]naphthyridine-2-thione of Formula XLIX. The cyclization can be carried out using the method described in step (4) of Reaction Scheme II.

In step (5) of Reaction Scheme IV, a 1,3-dihydro-1H-imidazo[4,5-c]quinoline-2-thione or 1,3-dihydro-1H-imidazo[4,5-c][1,5]naphthyridine-2-thione of Formula XLIX is methylated to provide a 2-(methylthio)-1H-imidazo[4,5-c]quinoline or a 2-(methylthio)-1H-imidazo[4,5-c][1,5]naphthyridine of Formula L. The reaction can be carried out using the method described in step (5) of Reaction Scheme II.

In step (6) of Reaction Scheme IV, a 2-(methylthio)-1H-imidazo[4,5-c]quinoline or a 2-(methylthio)-1H-imidazo[4,5-c][1,5]naphthyridine of Formula L is oxidized to provide a 2-(methylsulfonyl)-1H-imidazo[4,5-c]quinoline or a 2-(methylsulfonyl)-1H-imidazo[4,5-c][1,5]naphthyridine of Formula LI using a conventional oxidizing agent. The oxidation can be carried out using the method described in step (5) of Reaction Scheme II.

In step (7) of Reaction Scheme IV, a 2-(methylsulfonyl)-1H-imidazo[4,5-c]quinoline or a 2-(methylsulfonyl)-1H-imidazo[4,5-c][1,5]naphthyridine of Formula LI is treated with base to effect removal of the acetyl group and intramolecular displacement of the methylsulfonyl group by the hydroxy group to provide a compound of Formula LII. The reaction can be carried out by treating a compound of Formula LI with an aqueous solution of a base such as sodium hydroxide. The reaction can be carried out at ambient temperature.

In steps (8) and (9) of Reaction Scheme IV, a 1H-imidazo[4,5-c]quinoline or 1H-imidazo[4,5-c][1,5]naphthyridine of Formula LII is oxidized and then aminated to provide a 1H-imidazo[4,5-c]quinolin-6-amine or 1H-imidazo[4,5-c][1,5]naphthyridin-6-amine of Formula LIII, a subgenus of Formula I. The steps can be carried out using the methods described in steps (5) and (6) of Reaction Scheme I.

When the amino alcohol of the Formula $H_2N$—$CH(R_{1a})$—Z—OH that is used in step (1) is racemic, the compounds of Formulas LII and LIII may be obtained as a racemic mixture. A racemic mixture thus prepared can be resolved by methods known to one skilled in the art, for example, by reacting the racemic mixture with an enantiomerically pure sulfonic acid or carboxylic acid and selectively crystallizing a salt of one of the enantiomers from the mixture. Alternatively, an amino alcohol containing a single enantiomer may be used.

Reaction Scheme IV

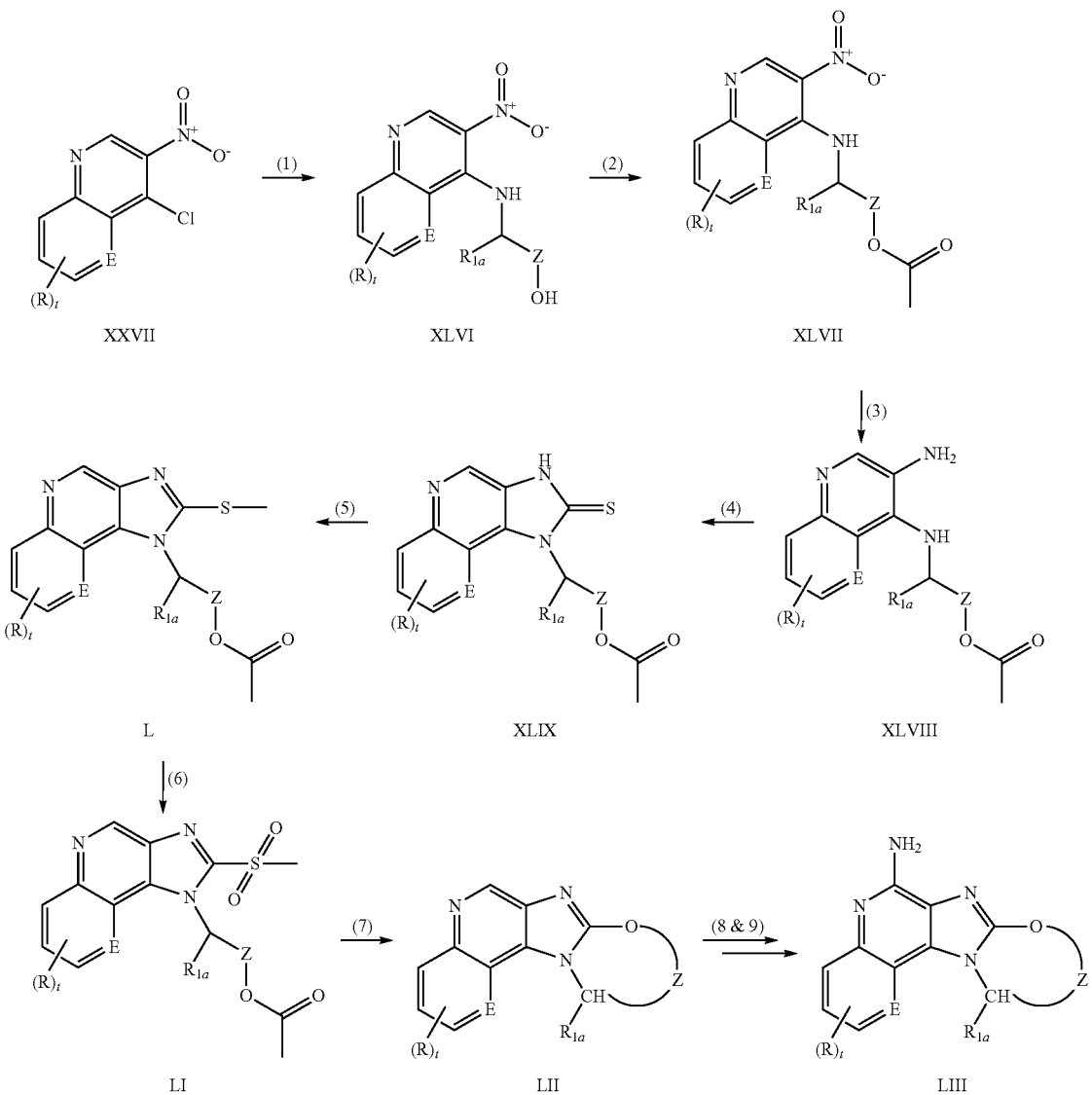

In some embodiments, compounds of the invention can be prepared according to Reaction Scheme V wherein $R_{1a}$, $R_{A1}$, $R_{B1}$, Bn, and Z are as defined above.

In step (1) of Reaction Scheme V, a 2,4-dichloro-3-nitropyridine of Formula LIV is treated with an amino alcohol of the Formula $H_2N—CH(R_{1a})—Z—OH$ to provide a compound of Formula LV. The reaction can be carried using the method described in step (1) of Reaction Scheme IV. Many 2,4-dichloro-3-nitropyridines of Formula LIV are known and can be prepared using conventional synthetic methods. See for example, U.S. Pat. No. 6,525,064 (Dellaria) and the references cited therein.

In step (2) of Reaction Scheme V, the hydroxy group on a 2-chloro-3-nitropyridin-4-amine of Formula LV is protected with an acetyl group using conventional methods. The reaction can be carried out using the method described in step (2) of Reaction Scheme IV.

In step (3) of Reaction Scheme V, a 2-chloro-3-nitropyridin-4-amine of Formula LVI is treated with dibenzylamine to provide an $N^2$-dibenzyl-3-nitropyridine-2,4-diamine of Formula LVII. The reaction can be carried out by combining a compound of Formula LVI with dibenzylamine and a tertiary amine such as triethylamine in a suitable solvent such as toluene. The reaction can be carried out at an elevated temperature.

In steps (4) through (8) of Reaction Scheme V, a $N^2$-dibenzyl-3-nitropyridine-2,4-diamine of Formula LVII is converted to a 1H-imidazo[4,5-c]pyridine of Formula LVIII using the methods described in steps (3) through (7) respectively of Reaction Scheme IV.

In step (9) of Reaction Scheme V, the benzyl groups of a compound of Formula LVIII are cleaved using transfer hydrogenation to provide a compound of Formula LIX, which is a subgenus of Formula I. The reaction can be carried out by adding ammonium formate to a solution of the compound of Formula LVIII in a suitable solvent such as ethanol or methanol in the presence of a catalyst such as palladium on carbon. The reaction can be carried out at an elevated temperature, for example, the reflux temperature of the solvent.

When the amino alcohol of the Formula $H_2N—CH(R_{1a})—Z—OH$ that is used in step (1) is racemic, the compounds of Formulas LVIII and LIX may be obtained as a racemic mixture. A racemic mixture thus prepared can be resolved by methods known to one skilled in the art, for example, by reacting the racemic mixture with an enantiomerically pure sulfonic acid or carboxylic acid and selectively crystallizing a salt of one of the enantiomers from the mixture. Alternatively, an amino alcohol containing a single enantiomer may be used.

from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen; each α-aminoacyl is an α-aminoacyl group derived from an α-amino acid selected from the group consisting of racemic, D-, and L-amino acids; Y' is selected from the group consisting of hydrogen, $C_{1-6}$ alkyl, and benzyl; $Y_0$ is selected

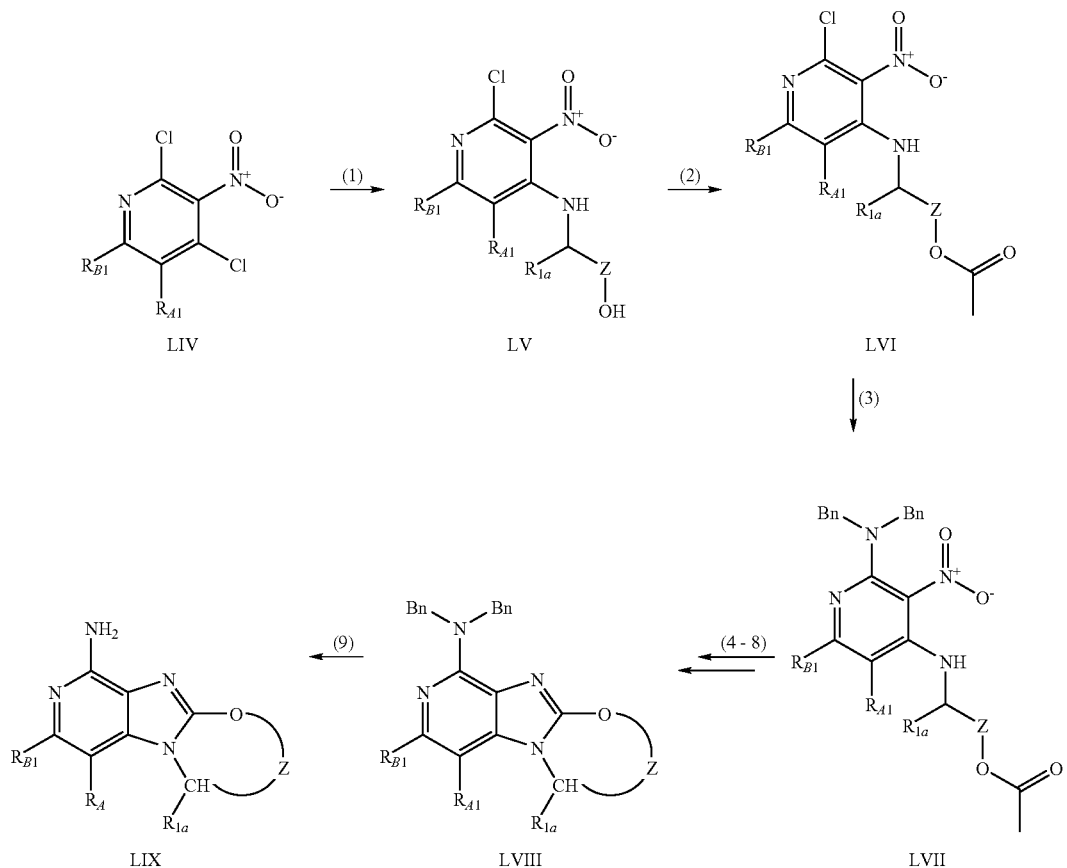

Reaction Scheme V

In some embodiments, compounds of the invention can be prepared according to Reaction Scheme VI wherein $R_A$, $R_B$, $D_1$, $D_2$, Z, and G are as defined above. The amino group of a compound of Formula I can be converted by conventional methods to a functional group such as an amide, carbamate, urea, amidine, or another hydrolyzable group. A compound of this type can be made by the replacement of a hydrogen atom in an amino group with a group such as —C(O)—R', α-aminoacyl, α-aminoacyl-α-aminoacyl, —C(O)—O—R', —C(O)—N(R")R', —C(=NY')—R', —CH(OH)—C(O)—OY', —CH(OC$_{1-4}$ alkyl)$Y_0$, —CH$_2Y_1$, and —CH(CH$_3$)$Y_1$; wherein R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N—$C_{1-6}$ alkylamino-$C_{1-4}$ alkylenyl; and $Y_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$alkylpiperazin-1-yl.

Particularly useful compounds of Formula V are amides derived from carboxylic acids containing one to ten carbon atoms, amides derived from amino acids, and carbamates containing one to ten carbon atoms. The reaction can be carried out, for example, by combining a compound of Formula I with a chloroformate or acid chloride, such as ethyl chloroformate or acetyl chloride, in the presence of a base such as triethylamine in a suitable solvent such as dichloromethane at ambient temperature.

Reaction Scheme VI

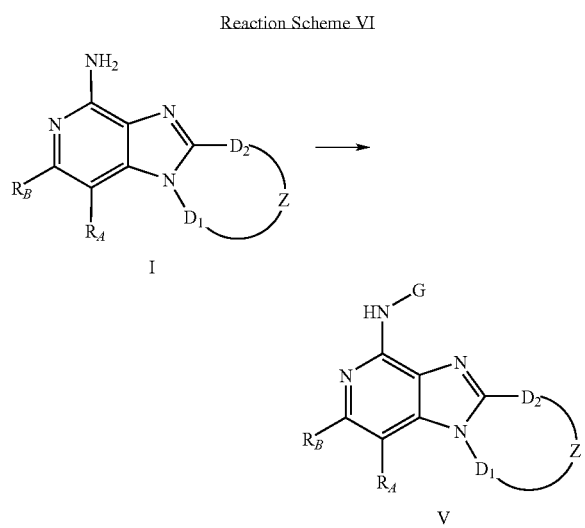

In some embodiments, compounds of the invention can be prepared according to Reaction Scheme VII wherein E, R, $R_{2a}$, $R_4$, $Q_1$, Boc, and t are as defined above and Tosyl is para-toluenesulfonyl.

In step (1) of Reaction Scheme VII, a tert-butyl N'-(3-aminoquinolin-4-yl)hydrazinecarboxylate or a tert-butyl N'-(3-amino[1,5]naphthyridin-4-yl)hydrazinecarboxylate of Formula XXXIX is reacted with a ketal or acetal of Formula $HOC(O)-CH_2-C(R_{2a})(OCH_2CH_3)$ to provide a compound of Formula LX. The reaction can be carried out using the method described in step (2) of Reaction Scheme III. Ketals or acetals of Formula $HOC(O)-CH_2-C(R_{2a})(OCH_2CH_3)$ are commercially available; others can be prepared using conventional methods as described in step (2) of Reaction Scheme III.

In step (2) of Reaction Scheme VII, a compound of Formula LX under goes two acid catalyzed cyclizations to provide a pyrazolo[1',5':1'2]imidazo[4,5-c]quinoline or a pyrazolo[1',5':1'2]imidazo[4,5-c][1,5]naphthyridine of Formula LXI. The cyclizations can be carried out in a one-pot two step procedure by (i) heating a solution of a compound of Formula LX in a suitable solvent such as propanol in the presence of an acid such as pyridinium para-toluenesulfonate to form the imidazole ring and (ii) adding a stronger acid such as hydrochloric acid to hydrolyze the ketal and Boc groups to form the pyrazole ring.

In step (3) of Reaction Scheme VII, the secondary amine in a pyrazolo[1',5':1'2]imidazo[4,5-c]quinoline or a pyrazolo[1',5':1'2]imidazo[4,5-c][1,5]naphthyridine of Formula LXI is protected. The reaction can be carried out by treating a solution of a compound of Formula LXI in a suitable solvent such as tetrahydrofuran with sodium hydride followed by the addition of p-toluenesulfonyl chloride. The reaction can be carried out at a sub-ambient temperature, such as 0° C., and then allowed to warm to ambient temperature.

In steps (4) and (5) of Reaction Scheme VII, a pyrazolo[1',5':1'2]imidazo[4,5-c]quinoline or a pyrazolo[1',5':1'2]imidazo[4,5-c][1,5]naphthyridine of Formula LXII is oxidized and then aminated to provide a pyrazolo[1',5':1'2]imidazo[4,5-c]quinolin-6-amine or a pyrazolo[1',5':1'2]imidazo[4,5-c][1,5]naphthyridin-6-amine of Formula LXIII, a subgenus of Formula I. The steps can be carried out using the methods described in steps (5) and (6) of Reaction Scheme I.

In step (6) of Reaction Scheme VII, the protecting group is removed from a pyrazolo[1',5':1'2]imidazo[4,5-c]quinolin-6-amine or a pyrazolo[1',5':1'2]imidazo[4,5-c][1,5]naphthyridin-6-amine of Formula LXIII to provide pyrazolo[1',5':1'2]imidazo[4,5-c]quinolin-6-amine or a pyrazolo[1',5':1'2]imidazo[4,5-c][1,5]naphthyridin-6-amine of Formula LXIV, a subgenus of Formula I. The deprotection can be effected by heating a solution of a compound of Formula LXIII and an alkoxide, such as sodium ethoxide, in an alcoholic solvent such as ethanol.

In step (7) of Reaction Scheme VII, the secondary amine in a pyrazolo[1',5':1'2]imidazo[4,5-c]quinolin-6-amine or a pyrazolo[1',5':1'2]imidazo[4,5-c][1,5]naphthyridin-6-amine of Formula LXIV is converted to an amide, sulfonamide, sulfamide, urea, or tertiary amine of Formula LXV, a subgenus of Formula I, using conventional methods. The reactions can be carried out using the methods described in step (8) of Reaction Scheme II.

Reaction Scheme VII

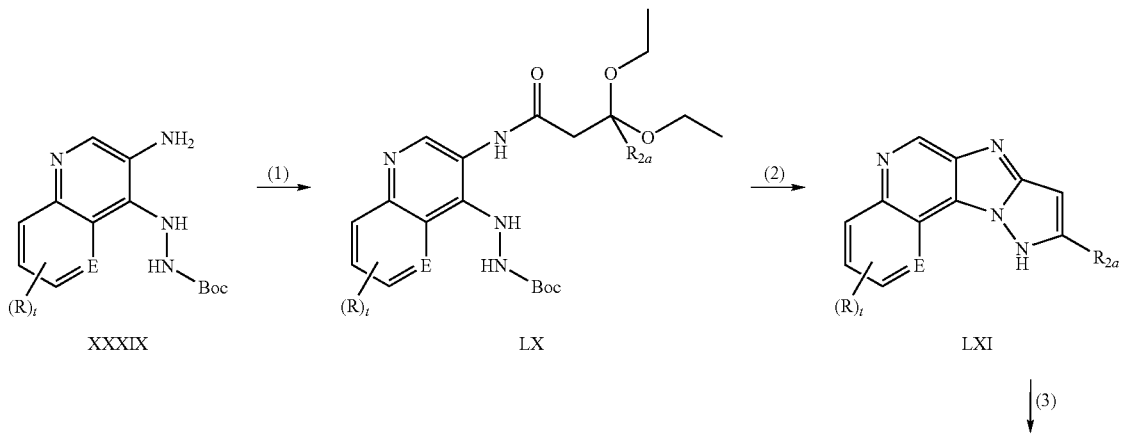

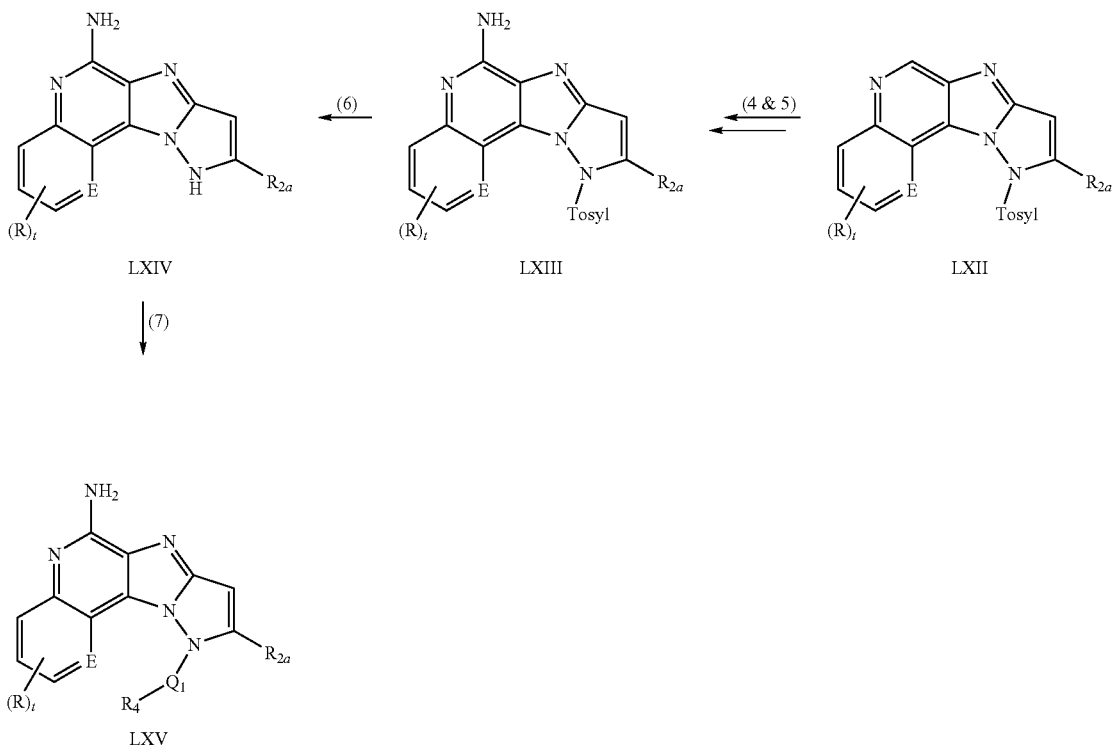

In some embodiments, compounds of the invention can be prepared according to Reaction Scheme VIII wherein E, R, $R_{2a}$, $R_4$, $Q_1$, Boc, Tosyl, and t are as defined above.

In step (1) of Reaction Scheme VIII, a tert-butyl N'-(3-aminoquinolin-4-yl)hydrazinecarboxylate or a tert-butyl N'-(3-amino[1,5]naphthyridin-4-yl)hydrazinecarboxylate of Formula XXXIX is reacted with cyanogen bromide to provide a 1H-imidazo[4,5-c]quinoline-1,2-diamine or 1H-imidazo[4,5-c][1,5]naphthyridine-1,2-diamine of Formula LXVI. The reaction can be carried out by adding cyanogen bromide to a solution of compound of Formula XXXIX in a suitable solvent such as ethanol and heating.

In step (2) of Reaction Scheme VIII, a 1H-imidazo[4,5-c]quinoline-1,2-diamine or 1H-imidazo[4,5-c][1,5]naphthyridine-1,2-diamine of Formula LXVI is treated with an ortho ester of Formula $R_{2a}C(O-alkyl)_3$ to provide a [1,2,4]triazolo[1',5':1,2]imidazo[4,5-c]quinoline or [1,2,4]triazolo[1',5':1,2]imidazo[4,5-c][1,5]naphthyridine of Formula LXVII. The reaction can be carried out by adding the ortho ester to a compound of Formula LXVI in a suitable solvent such as toluene. The reaction is carried out at a temperature high enough to drive off alcohol formed during the reaction; a Dean-Stark trap can be used to collect the volatiles.

In step (3) of Reaction Scheme VIII, the secondary amine of a [1,2,4]triazolo[1',5':1,2]imidazo[4,5-c]quinoline or [1,2,4]triazolo[1',5':1,2]imidazo[4,5-c][1,5]naphthyridine of Formula LXVII is protected. The reaction can be carried out as described in step (3) of Reaction Scheme VII.

In steps (4) and (5) of Reaction Scheme VIII, a compound of Formula LXVIII is oxidized and then aminated to provide of a [1,2,4]triazolo[1',5':1,2]imidazo[4,5-c]quinolin-6-amine or [1,2,4]triazolo[1',5':1,2]imidazo[4,5-c][1,5]naphthyridin-6-amine of Formula LXIX, which is a subgenus of Formula I The steps can be carried out using the methods described in steps (5) and (6) of Reaction Scheme I.

In step (6) of Reaction Scheme VIII, the protecting group is removed from a compound of Formula LXIX to provide a [1,2,4]triazolo[1',5':1,2]imidazo[4,5-c]quinolin-6-amine or [1,2,4]triazolo[1',5':1,2]imidazo[4,5-c][1,5]naphthyridin-6-amine of Formula LXX, which is a subgenus of Formula I. The deprotection can be effected as described in step (6) of Reaction Scheme VII.

In step (7) of Reaction Scheme VIII, the secondary nitrogen in [1,2,4]triazolo[1',5':1,2]imidazo[4,5-c]quinolin-6-amine or [1,2,4]triazolo[1',5':1,2]imidazo[4,5-c][1,5]naphthyridin-6-amine of Formula LXX is converted to an amide, sulfonamide, sulfamide, urea, or tertiary amine of Formula LXXI, a subgenus of Formula I, using conventional methods. The reactions can be carried out using the methods described in step (8) of Reaction Scheme II.

Reaction Scheme VIII

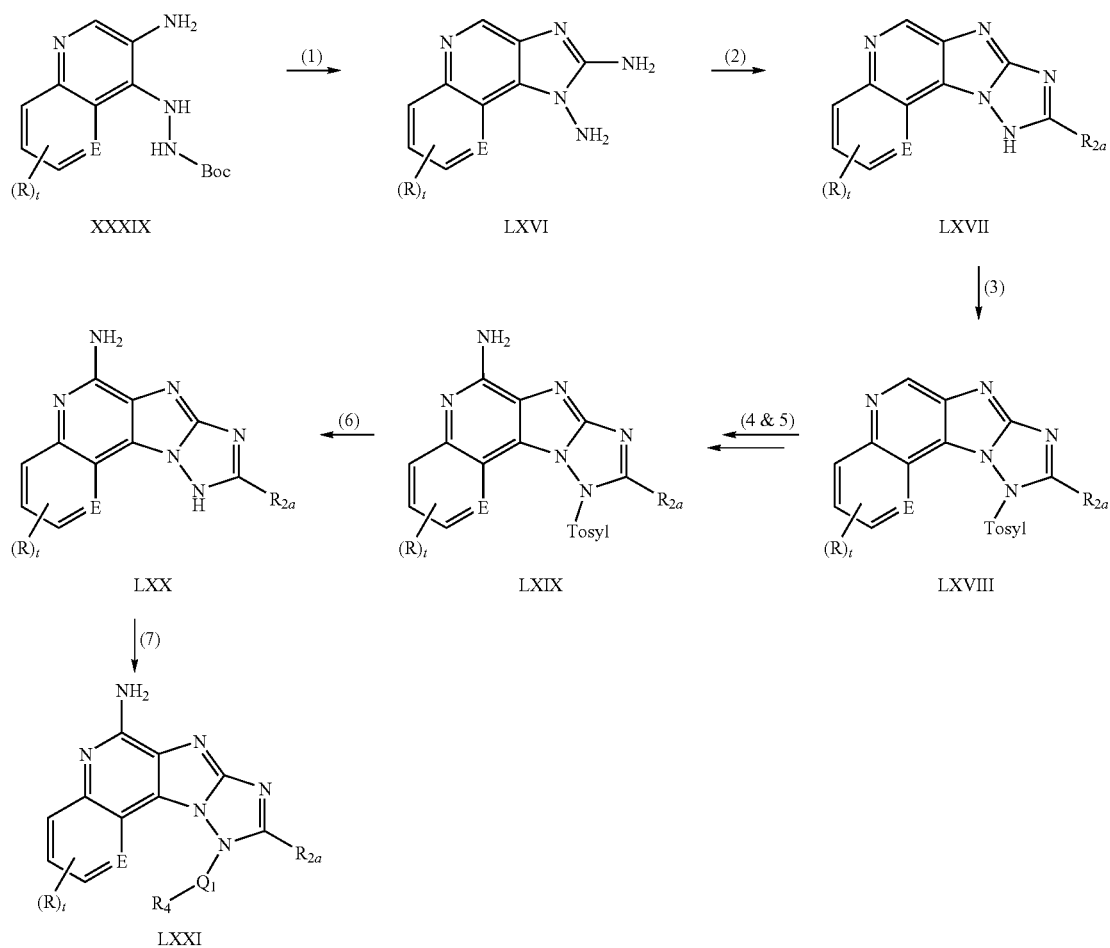

Methods of installing an $R_3$ group to provide a compound of Formula II or III wherein m is 1 are known. See for example, U.S. Patent Application Publication No. 2004/0147543 (Hays); International Publication Nos. WO 2005/020999 (Lindstrom), WO 2005/032484 (Lindstrom), WO 2005/123080 (Merrill), and WO 2006/038923 (Niwas); pending International Application No. PCT/2006/004713 (Rice); and the references cited therein.

In some embodiments, for compounds wherein $D_1$ is —CH($R_1$)—, the $R_1$ group may be installed or further elaborated using the methods disclosed in pending International Application Nos. PCT/US2005/047258 (Griesgraber) and PCT/US2005/047297 (Griesgraber).

Compounds of the invention can also be prepared using variations of the synthetic routes shown in the Reaction Schemes above that would be apparent to one of skill in the art. For example, a 2,4-dichloro-3-nitropyridine of Formula LIV could be used in lieu of a 4-chloro-3-nitroquinoline in Reaction Scheme II and the 4-amine group installed using the method described in Reaction Scheme V. Compounds of the invention can also be prepared using the synthetic methods described in the EXAMPLES below.

Pharmaceutical Compositions and Biological Activity

Pharmaceutical compositions of the invention contain a therapeutically effective amount of a compound or salt described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. The exact amount of compound or salt used in a pharmaceutical composition of the invention will vary according to factors known to those of skill in the art, such as the physical and chemical nature of the compound or salt, the nature of the carrier, and the intended dosing regimen.

In some embodiments, the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (µg/kg) to about 5 mg/kg, of the compound or salt to the subject.

In other embodiments, the compositions of the invention will contain sufficient active ingredient or prodrug to provide a dose of, for example, from about 0.01 mg/m² to about 5.0 mg/m², computed according to the Dubois method, in which the body surface area of a subject (m²) is computed using the subject's body weight: $m^2 = (wt\ kg^{0.425} \times height\ cm^{0.725}) \times 0.007184$, although in some embodiments the methods may be performed by administering a compound or salt or composition in a dose outside this range. In some of these embodiments, the method includes administering sufficient compound to provide a dose of from about 0.1 mg/m² to about 2.0 mg/m² to the subject, for example, a dose of from about 0.4 mg/m² to about 1.2 mg/m².

A variety of dosage forms may be used, such as tablets, lozenges, capsules, parenteral formulations, syrups, creams, ointments, aerosol formulations, transdermal patches, transmucosal patches and the like. These dosage forms can be prepared with conventional pharmaceutically acceptable carriers and additives using conventional methods, which generally include the step of bringing the active ingredient into association with the carrier.

The compounds or salts of the invention can be administered as the single therapeutic agent in the treatment regimen, or the compounds or salts described herein may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the tests set forth below. These results indicate that the compounds or salts are useful for modulating the immune response in a number of different ways, rendering them useful in the treatment of a variety of disorders.

Cytokines whose production may be induced by the administration of compounds or salts of the invention generally include interferon-α (IFN-α) and tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt of the invention to the animal. The animal to which the compound or salt is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts described herein can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt or composition and other component or components may be administered separately; together but independently such as in a solution; or together and associated with one another such as (a) covalently linked or (b) non-covalently associated, e.g., in a colloidal suspension.

Conditions for which compounds or salts or compositions identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such as chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to acute myeloid leukemia, acute lymphocytic leukemia, chronic myeloid leukemia, chronic lymphocytic leukemia, multiple myeloma, Hodgkin's lymphoma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, a compound or salt identified herein may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influ-* enza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts identified herein may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An animal may also be vaccinated by administering an effective amount of a compound or salt described herein, as a vaccine adjuvant. In one embodiment, there is provided a method of vaccinating an animal comprising administering an effective amount of a compound or salt described herein to the animal as a vaccine adjuvant.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 μg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments the induction or inhibition of cytokine biosynthesis may be performed by administering a compound or salt in a dose outside this range. In some of these embodiments, the method includes administering sufficient compound or salt or composition to provide a dose of from about 0.1 mg/m$^2$ to about 2.0 mg/m$^2$ to the subject, for example, a dose of from about 0.4 mg/m$^2$ to about 1.2 mg/m$^2$.

The invention also provides a method of treating a viral infection in an animal and a method of treating a neoplastic disease in an animal comprising administering an effective amount of a compound or salt of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments either of these methods may be performed by administering a compound or salt in a dose outside this range. In some of these embodiments, the method includes administering sufficient compound or salt to provide a dose of from about 0.1 mg/m$^2$ to about 2.0 mg/m$^2$ to the subject, for example, a dose of from about 0.4 mg/m$^2$ to about 1.2 mg/m$^2$.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

In the examples below automated flash chromatography on silica gel was carried out using a COMBIFLASH system (an automated high-performance flash purification product available from Teledyne Isco, Inc., Lincoln, Nebr., USA), a HORIZON HPFC system (an automated high-performance flash purification product available from Biotage, Inc, Charlottesville, Va., USA) or an INTELLIFLASH Flash Chromatography System (an automated flash purification system available from AnaLogix, Inc, Burlington, Wis., USA). The eluent used in each purification is given in the example. In some chromatographic separations, the solvent mixture 80/18/2 v/v/v chloroform/methanol/concentrated ammonium hydroxide (CMA) was used as the polar component of the eluent. In these separations, CMA was mixed with chloroform in the indicated ratio.

Example 1

9,10-Dihydro-8H-[1,2]oxazino[2',3':1,2]imidazo[4,5-c]quinolin-6-amine

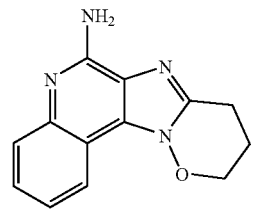

Part A

A solution of 4-chloroquinolin-3-amine (3.70 g, 20.74 mmol) and 4-bromobutyryl chloride (11.54 g, 62.22 mmol) dissolved in 100 mL of 1,2-dichloroethane was heated to reflux. After 17 hours the reaction was cooled to room temperature, diluted with dichloromethane, washed with saturated aqueous K$_2$CO$_3$, H$_2$O and brine, dried over Na$_2$SO$_4$, and concentrated under reduced pressure to give a brown solid. The solid was triturated with a mixture of hexane and ether, filtered and dried to give 4-bromo-N-(4-chloroquinolin-3-yl)butanamide (3.65 g) as a brown solid.

Part B

A mixture of 4-bromo-N-(4-chloroquinolin-3-yl)butanamide (2.090 g, 6.379 mmol) and O-benzylhydroxylamine hydrochloride (1.527 g, 9.569 mmol) in 20 mL of isopropanol was heated to 82° C. under an atmosphere of $N_2$. After 18 hours the solution was cooled, solids were filtered off and rinsed with ether. The brown solid was dried to give 1.87 g of 2-(3-chloropropyl)-1H-imidazo[4,5-c]quinolin-1-ol.

Part C

A stirred solution of 2-(3-chloropropyl)-1H-imidazo[4,5-c]quinolin-1-ol (1.669 g, 6.379 mmol) in 60 mL of anhydrous tetrahydrofuran (THF) was cooled in an ice bath to ~6° C. under an atmosphere of $N_2$. The reaction solution was treated with potassium t-butoxide (0.68 g, 8.29 mmol) and allowed to warm to ambient temperature. After 4 days more potassium t-butoxide was added (0.2 g, 2.4 mmol). After an additional 2 hours the solution was concentrated under reduced pressure. The resulting brown oil was diluted with dichloromethane, washed successively with dilute aqueous $K_2CO_3$, $H_2O$, and brine, dried over $Na_2SO_4$, and concentrated under reduced pressure to give 1.89 g of a brown solid. Chromatography ($SiO_2$, 0-15% CMA/$CHCl_3$) gave 0.3339 g of 9,10-dihydro-8H-[1,2]oxazino[2',3':1,2]imidazo[4,5-c]quinoline as a brown solid.

Part D 9,10-Dihydro-8H-[1,2]oxazino[2',3':1,2]imidazo[4,5-c]quinoline (0.3339 g, 1.482 mmol) was dissolved in 5 mL of dichloromethane and treated with 3-chloroperoxybenzoic acid (0.95 g, 57-86% purity). After stirring for 1 hour, the reaction mixture was diluted with 15 mL of dichloromethane, washed successively with dilute aqueous $K_2CO_3$, $H_2O$, and brine, dried over $Na_2SO_4$, and concentrated under reduced pressure to give 0.364 g of 9,10-dihydro-8H-[1,2]oxazino[2',3':1,2]imidazo[4,5-c]quinoline 5-oxide as a tan solid.

Part E

A solution of 9,10-dihydro-8H-[1,2]oxazino[2',3':1,2]imidazo[4,5-c]quinoline 5-oxide (0.364 g, 1.51 mmol) in 10 mL of dichloromethane was treated with 7 mL of concentrated aqueous $NH_4OH$ solution. The mixture was stirred rapidly and then p-toluenesulfonyl chloride (0.34 g, 1.78 mmol) was carefully added. Rapid stirring was continued for 2 hours. The reaction mixture was then diluted with more dichloromethane, washed successively with dilute aqueous $K_2CO_3$, $H_2O$, and brine, dried over $Na_2SO_4$, and concentrated under reduced pressure. The solid was dissolved in hot $CH_3CN$. The resulting crystals were filtered off and dried to give 0.0578 g of 9,10-dihydro-8H-[1,2]oxazino[2',3':1,2]imidazo[4,5-c]quinolin-6-amine as a tan solid, dec. 229-234° C. MS (APCI) m/z 241 $(M+H)^+$; Anal. calcd for $C_{13}H_{12}N_4O$: C, 64.99; H, 5.03; N, 23.32. Found: C, 64.81; H, 4.74; N, 23.44.

Example 2

8,9,10,11-Tetrahydro[1,2]oxazepino[2',3':1,2]imidazo[4,5-c]quinolin-6-amine

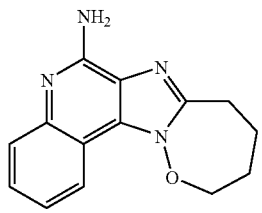

Part A

A solution of 4-chloroquinolin-3-amine (4.00 g, 22.39 mmol) and 5-chlorovaleryl chloride (1.30 mL, 33.6 mmol) dissolved in 150 mL of 1,2-dichloroethane was heated to reflux. After 2.8 days more 5-chlorovaleryl chloride (1.0 mL, 7.7 mmol) was added. After 16 hours more the reaction was cooled to room temperature, diluted with dichloromethane, washed with saturated aqueous $K_2CO_3$, $H_2O$, and brine, dried over $Na_2SO_4$, and concentrated under reduced pressure to give 3.78 g of 5-chloro-N-(4-chloroquinolin-3-yl)pentanamide as a tan solid.

Part B

A mixture of 5-chloro-N-(4-chloroquinolin-3-yl)pentanamide (1.0 g, 3.365 mmol) and O-benzylhydroxylamine hydrochloride (0.59 g, 3.70 mmol) in 10 mL of isopropanol was heated to 82° C. under an atmosphere of $N_2$. After 2 days the mixture was cooled, solids were filtered off and rinsed with hexane and then ether. The brown solid was dried to give 0.4105 g of 2-(4-chlorobutyl)-1H-imidazo[4,5-c]quinolin-1-ol.

Part C

A stirred solution of 2-(4-chlorobutyl)-1H-imidazo[4,5-c]quinolin-1-ol (0.167 g, 0.606 mmol) in 6 mL of anhydrous DMF was treated with 60% NaH in mineral oil (0.032 g, 0.787 mmol). After 45 minutes the mixture was poured into 20 mL of water and washed with ethyl acetate. The organic portions were combined, washed successively with dilute aqueous $K_2CO_3$, $H_2O$, and brine, dried over $Na_2SO_4$, and concentrated under reduced pressure to give 0.154 g of 8,9,10,11-tetrahydro[1,2]oxazepino[2',3':1,2]imidazo[4,5-c]quinoline as a tan solid.

Part D

A solution of 8,9,10,11-tetrahydro[1,2]oxazepino[2',3':1,2]imidazo[4,5-c]quinoline (0.1449 g, 0.605 mmol) in 6 mL of dichloromethane was treated with 3-chloroperoxybenzoic acid (0.30 g, 57-86% purity). After stirring for 40 minutes, the reaction mixture was diluted with dichloromethane, washed successively with dilute aqueous $K_2CO_3$, $H_2O$, and brine, dried over $Na_2SO_4$, and concentrated under reduced pressure to give 0.1384 g of 8,9,10,11-tetrahydro[1,2]oxazepino[2',3':1,2]imidazo[4,5-c]quinoline 5-oxide as a tan solid.

Part E

A solution of 8,9,10,11-tetrahydro[1,2]oxazepino[2',3':1,2]imidazo[4,5-c]quinoline 5-oxide (0.1384 g, 0.5421 mmol) in 6 mL of dichloromethane was treated with 3 mL of concentrated aqueous $NH_4OH$ solution. The mixture was stirred rapidly and then p-toluenesulfonyl chloride (0.12 g, 0.65 mmol) was carefully added. Rapid stirring was continued for 40 minutes. The reaction mixture was then diluted with more dichloromethane, washed successively with dilute aqueous $K_2CO_3$, $H_2O$ and brine, dried over $Na_2SO_4$, and concentrated under reduced pressure. The solid was triturated with ether and filtered. Crystallization from acetonitrile gave 0.0369 g of 8,9,10,11-tetrahydro[1,2]oxazepino[2',3':1,2]imidazo[4,5-c]quinolin-6-amine as a white powder, dec. 247-255° C. MS (APCI) m/z 255 $(M+H)^+$; Anal. calcd for $C_{14}H_{14}N_4O$: C, 66.13; H, 5.55; N, 22.03. Found: C, 65.82; H, 5.27; N, 22.11.

Example 3

8 8,9-Dihydroisoxazolo[2',3':1,2]imidazo[4,5-c]quinolin-6-amine

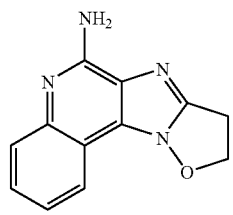

Part A

A solution of 4-chloroquinolin-3-amine (6.00 g, 33.59 mmol) and 3-chloropropionyl chloride (4.8 mL, 50.39 mmol) dissolved in 200 mL of 1,2-dichloroethane was heated to 50° C. in an oil bath. After 20 hrs the temperature of the oil bath was increased to 90° C. After an additional 26 hours the reaction was cooled to room temperature, diluted with dichloromethane, washed with saturated aqueous $K_2CO_3$, $H_2O$, and brine, dried over $Na_2SO_4$, and concentrated under reduced pressure to give 7.12 g of 3-chloro-N-(4-chloroquinolin-3-yl)propanamide as a tan solid.

Part B

A mixture of 3-chloro-N-(4-chloroquinolin-3-yl)propanamide (1.682 g, 6.243 mmol) and O-benzylhydroxylamine hydrochloride (1.10 g, 6.87 mmol) in 60 mL of isopropanol was heated to 40° C. under an atmosphere of $N_2$. After 25 hours the mixture was cooled, solids were filtered off and rinsed with hexane. Chromatography ($SiO_2$, 8-100% EtOAc/dichloromethane) gave 0.6308 g of 1-(benzyloxy)-2-(2-chloroethyl)-1H-imidazo[4,5-c]quinoline as a tan solid.

Part C

A stirred solution of 1-(benzyloxy)-2-(2-chloroethyl)-1H-imidazo[4,5-c]quinoline (0.6058 g, 1.793 mmol) in 10 mL of dichloromethane was treated with a 1 M solution of $BBr_3$ in dichloromethane (5.4 mL, 5.379 mmol). After 2 hours, 10 mL of saturated, aqueous $K_2CO_3$ solution were added and the reaction mixture stirred under ambient conditions for 3 hrs. The organic portion was separated and washed successively with $H_2O$ and brine, dried over $Na_2SO_4$, and concentrated under reduced pressure. Chromatography ($SiO_2$, 0-15% CMA/CHCl$_3$) gave 0.0465 g of 8,9-dihydroisoxazolo[2',3':1,2]imidazo[4,5-c]quinoline as a tan solid.

Part D

A solution of 8,9-dihydroisoxazolo[2',3':1,2]imidazo[4,5-c]quinoline (0.0465 g, 0.220 mmol) in 5 mL of dichloromethane was treated with 3-chloroperoxytbenzoic acid (0.11 g, 57-86% purity). After stirring for 30 minutes, the reaction mixture was diluted with dichloromethane, washed with dilute aqueous $K_2CO_3$ and the organic solution carried on without isolation of 8,9-dihydroisoxazolo[2',3':1,2]imidazo[4,5-c]quinoline 5-oxide.

Part E

A solution of 8,9-dihydroisoxazolo[2',3':1,2]imidazo[4,5-c]quinoline 5-oxide (0.0499 g, 0.220 mmol) in dichloromethane from the previous step was treated with 1.5 mL of concentrated aqueous $NH_4OH$ solution. The mixture was stirred rapidly and then p-toluenesulfonyl chloride (0.046 g, 0.242 mmol) was carefully added. Rapid stirring was continued for 5 minutes. The reaction mixture was then diluted with more dichloromethane, washed successively with dilute aqueous $K_2CO_3$, $H_2O$ and brine, dried over $Na_2SO_4$, and concentrated under reduced pressure. Chromatography ($SiO_2$, 0-15% CMA/CHCl$_3$) gave 0.015 g of 8,9-dihydroisoxazolo[2',3':1,2]imidazo[4,5-c]quinolin-6-amine as a brown solid, mp greater than 300° C.

HRMS (ESI) calcd for $C_{12}H_{10}N_4O$ M+H$^+$: 227.0933. found 227.0936.

Example 4

9,10-Dihydro-8H-[1,2]oxazino[2',3':1,2]imidazo[4,5-c][1,5]naphthyridin-6-amine

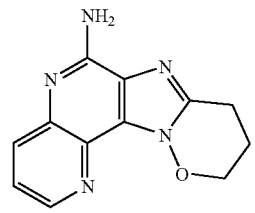

Part A

A mixture of 4-chloro[1,5]naphthyridin-3-amine (2.0 g, 11 mmol) and 4-chlorobutyryl chloride (4.7 g, 33 mmol) in 1,2-dichloroethane (75 mL) was heated at reflux for 20 hours. The reaction mixture was then concentrated under reduced pressure and the residue washed with two 25 mL portions of hexane. The solid was then taken up in methanol (35 mL), 1.0 mL of 10% solution of sodium hydroxide in water was added, and the solution was stirred at room temperature for 4 hours. The reaction mixture was then concentrated under reduced pressure to provide 4-chloro-N-(4-chloro[1,5]naphthyridin-3-yl)butanamide which was used directly in the next step without further purification.

MS (ESI) m/z 284 (M+H)$^+$.

Part B

A mixture of 4-chloro-N-(4-chloro[1,5]naphthyridin-3-yl)butanamide (3.1 g, 11 mmol) and O-benzylhydroxylamine hydrochloride (2.1 g, 13 mmol) in isopropanol (75 mL) was heated at reflux for 24 hours, then pyridinium p-toluenesulfonate (0.25 g, 1.0 mmol) was added and reflux continued for 48 more hours. The reaction mixture was then concentrated under reduced pressure and dichloromethane (50 mL) and saturated aqueous sodium carbonate (25 mL) were added and the mixture was stirred for 72 hours. The dichloromethane layer was then separated, concentrated under reduced pressure, and the residue purified by chromatography (silica gel eluted with 10% methanol in dichloromethane containing 5 mL of ammonium hydroxide solution per liter) to provide 0.13 g of 9,10-dihydro-8H-[1,2]oxazino[2',3':1,2]imidazo[4,5-c][1,5]naphthyridine.

MS (APCI) m/z 227 (M+H)$^+$.

Part C

Solid 3-chloroperoxybenzoic acid (0.26 g of approximately 77% pure material, 1.1 mmol) was added to a solution of 9,10-dihydro-8H-[1,2]oxazino[2',3':1,2]imidazo[4,5-c][1,5]naphthyridine (0.13 g, 0.6 mmol) in dichloromethane (15 mL). The reaction was stirred at room temperature for 1 hour and then washed with saturated aqueous sodium carbonate (10 mL). The aqueous fraction was extracted 5 times with 25 mL portions of dichloromethane. The combined organic fractions were dried over potassium carbonate, filtered, and concentrated under reduced pressure to provide 9,10-dihydro-8H-[1,2]oxazino[2',3':1,2]imidazo[4,5-c][1,5]naphthyridine 5-oxide (0.13 g).

Part D

To a stirred solution of 9,10-dihydro-8H-[1,2]oxazino[2',3':1,2]imidazo[4,5-c][1,5]naphthyridine 5-oxide (0.13 g, 0.54 mmol) in dichloromethane (10 mL) was added trichloroacetyl isocyanate (0.08 mL, 0.67 mmol). After 1.5 hours, the solution was concentrated under reduced pressure and methanol (4 mL) and sodium methoxide (2 drops of a 25% w/w solution in methanol) were added with stirring. After 18 hours the solution was concentrated under reduced pressure. The resulting solid was recrystallized from methanol/ethyl acetate to provide 9,10-dihydro-8H-[1,2]oxazino[2',3':1,2]imidazo[4,5-c]-1,5-naphthyridin-6-amine.

MS (APCI) m/z 242 (M+H$^+$); HRMS (ESI) calcd for $C_{12}H_{11}N_5O$ M+H$^+$: 242.1042. found 242.1040.

Example 5

8,9,10,11-Tetrahydropyrimido[1',2':1,2]imidazo[4,5-c]quinolin-6-amine

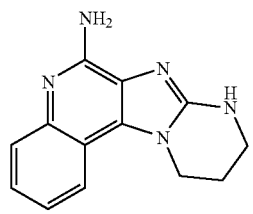

Part A 2,4-Dichloro-3-nitroquinoline (20 g, 81.6 mmol) and N,N-dimethylformamide (DMF, 200 mL) were combined in a 1 L round-bottomed flask and stirred for 5 minutes. Triethylamine (12.5 mL, 89.8 mmol) was added in a single portion. 3-Aminopropan-1-ol (6.9 mL, 89.8 mmol) was added in small portions. The reaction mixture was stirred at ambient temperature for 4 hours. Water (about 700 mL) was added and the reaction mixture was stirred for 30 minutes. A yellow precipitate was isolated by filtration, washed with water (about 1 L), and dried under vacuum overnight to provide 22.5 g of 3-[(2-chloro-3-nitroquinolin-4-yl)amino]propan-1-ol.

Part B

3-[(2-Chloro-3-nitroquinolin-4-yl)amino]propan-1-ol 11.53 g), acetonitrile (110 mL), and 5% platinum on carbon (1.3 g) were added sequentially to a Parr vessel. The vessel was placed under hydrogen pressure, 40 psi (2.8×10$^5$ Pa) for 4 hours. The reaction mixture was filtered through a layer of CELITE filter aid and the filtrate was concentrated under reduced pressure. The residue was dried under vacuum for 2 hours to provide 9.97 g of 3-[(3-amino-2-chloroquinolin-4-yl)amino]propan-1-ol as a brown sticky oil.

Part C

To a round-bottomed flask containing 3-[(3-amino-2-chloroquinolin-4-yl)amino]propan-1-ol (9.97 g, 39.6 mmol) was added ethanol (100 mL) followed by cyanogen bromide (4.5 g, 43.6 mmol). The reaction was stirred at 70° C. overnight.

To the reaction mixture was added cyanogen bromide (820 mg) and the reaction was heated to reflux for 3 hours (h). The reaction mixture was cooled to ambient temperature and the solvent was removed under reduced pressure to afford a greenish gray solid (14.23 g). A portion of this solid (13.2 g) was transferred to an Erlenmeyer flask. 2N NaOH (775 mL) was added and the resulting suspension was stirred for 45 minutes. The suspension was filtered and the residue was dried under reduced pressure to afford 3-(2-amino-4-chloro-1H-imidazo[4,5-c]quinolin-1-yl)propan-1-ol (6.97 g) as a grey solid.

Part D

To a round-bottomed flask containing 3-(2-amino-4-chloro-1H-imidazo[4,5-c]quinolin-1-yl)propan-1-ol (7.17 g, 25.9 mmol) was added 1,2-dichloroethane (210 mL) and the suspension was stirred for 5 minutes. To the stirred suspension was added thionyl chloride (5.6 mL, 77.7 mmol) and the reaction was heated to 50° C. overnight. The reaction was cooled to ambient temperature, filtered, and the residue was washed with 1,2-dichloroethane (100 mL) and diethyl ether (3×100 mL) to afford the product. The product was dried under reduced pressure to afford 4-chloro-1-(3-chloropropyl)-1H-imidazo[4,5-c]quinolin-2-amine (7.92 g) as a light brown solid.

Part E

To a round-bottomed flask containing 4-chloro-1-(3-chloropropyl)-1H-imidazo[4,5-c]quinolin-2-amine (7.92 g, 26.8 mmol) was added N,N-dimethylacetamide (200 mL) and the mixture was stirred for 5 minutes. To the stirred solution was added sodium hydride (60% dispersion in mineral oil, 3.9 g, 80.54 mmol) and the reaction was stirred at 50° C. After 1.5 h the reaction was cooled to ambient and quenched by the careful addition of water (1 L). The reaction was transferred to a separatory funnel and ethyl acetate (1 L) was added. The organic layer was separated and the aqueous layer was extracted with ethyl acetate (1 L). The organic layers were combined, washed with water (2×1 L), dried (MgSO$_4$), filtered, and the solvent was evaporated. The resultant product was dried under reduced pressure to afford 6-chloro-8,9,10,11-tetrahydropyrimido[1',2':1,2]imidazo[4,5-c]quinoline (6.54 g).

Part F

To a steel vessel was added 6-chloro-8,9,10,11-tetrahydropyrimido[1',2':1,2]imidazo[4,5-c]quinoline (3.31 g, 12.8 mmol) and 7 N ammonia in methanol (200 mL). The vessel was sealed and heated in an oven at 150° C. for 8 days. The reaction was cooled to ambient temperature and the solvent was removed under reduced pressure to afford a light brown solid (2.33 g). The product was purified by automated flash chromatography (ISCO Combiflash Separation System, Biotage Si 40+M column, eluted with a gradient of 0-11% methanol in dichloromethane with 1% ammonium hydroxide) and the cleanest fractions were retained and the solvent evaporated to provide 8,9,10,11-tetrahydropyrimido[1',2':1,2]imidazo[4,5-c]quinolin-6-amine (124 mg) as a light brown solid, mp>250° C.; MS (ESI) m/z 340 (M+H)$^+$; Anal. Calcd for $C_{13}H_{13}N_5.0.25H_2O$: C, 64.05; H, 5.58; N, 28.73. Found C, 63.71; H, 5.80; N, 28.46.

Example 6

10-Methyl-9,10-dihydro-8H-imidazo[1',2':1,2]imidazo[4,5-c]quinolin-6-amine

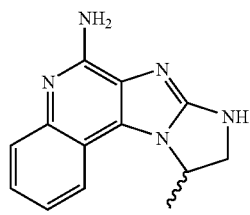

10-Methyl-9,10-dihydro-8H-imidazo[1',2':1,2]imidazo[4,5-c]quinolin-6-amine was prepared according to the general methods of Example 5 using DL-alaninol in lieu of 3-aminopropan-1-ol. The compound decomposed at 189° C. MS (ESI) m/z 240 (M+H)$^+$. Anal. Calcd for $C_{13}H_{13}N_5 \cdot 0.25$ $CH_4O$: C, 64.36; H, 5.71; N, 28.32. Found C, 64.11; H, 5.61; N, 28.95.

Example 7

3-Bromo-10,11-dihydro-9H-[1,3]oxazino[3',2':1,2]imidazo[4,5-c]quinolin-6-amine

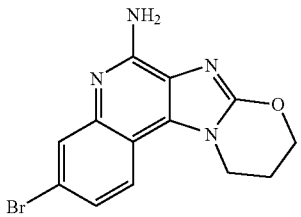

Part A

To a round-bottomed flask containing 7-bromo-4-chloro-3-nitroquinoline (60 g, 209.1 mmol) was added DMF (390 mL) and triethylamine (44 mL, 313.6 mmol) and the solution was stirred at 0° C. in an ice-bath. To this cooled solution was added 3-aminopropan-1-ol (17.6 mL, 230.0 mmol) and the reaction was stirred at ambient temperature overnight. The solvent was removed under reduced pressure and the resultant orange solid was recrystallized from ethyl acetate (800 mL). The product was separated by filtration and the solids were washed with diethyl ether and dried under reduced pressure to afford crude 3-[(7-bromo-3-nitroquinolin-4-yl)amino]propan-1-ol (88.15 g) as a brown solid.

Part B

To a round-bottomed flask containing 3-[(7-bromo-3-nitroquinolin-4-yl)amino]propan-1-ol (88.15 g) was added dichloromethane (DCM, 600 mL) followed by triethylamine (38 mL, 270.8 mmol) and the solution was stirred for 5 minutes. In a separate flask a solution of acetyl chloride (14.4 mL, 202.5 mmol) in dichloromethane (300 mL) was prepared. The acetyl chloride solution was added to the reaction mixture in a dropwise fashion. The reaction was stirred at ambient temperature for 4 h. Additional acetyl chloride (2.8 mL in DCM (50 mL)) was added and the reaction mixture was stirred at ambient temperature overnight. At this time additional acetyl chloride (1.4 mL in dichloromethane (25 mL)) was added and the reaction was stirred at ambient temperature for 1 h. Additional dichloromethane (200 mL) was then added and the reaction was transferred to a separatory funnel. The organic layer was washed with water (2×800 mL) and brine (1×800 mL). The organic layer was separated, dried (MgSO$_4$), filtered, and the solvent evaporated to afford 3-[(7-bromo-3-nitroquinolin-4-yl)amino]propyl acetate (60.8 g) as a bright yellow solid.

Part C

To a hydrogenation flask was added a solution of 3-[(7-bromo-3-nitroquinolin-4-yl)amino]propyl acetate (60.8 g, 165.1 mmol) in acetonitrile (600 mL) followed by 5% platinum on carbon (6.7 g) and the reaction was hydrogenated at 40 psi (2.8×10$^5$ Pa) overnight. The reaction was filtered through CELITE filter aid and the filtrate was collected. The solvent was removed under reduced pressure to afford 3-[(3-amino-7-bromoquinolin-4-yl)amino]propyl acetate (54.6 g) as an oil.

Part D

To a round-bottomed flask containing 3-[(3-amino-7-bromoquinolin-4-yl)amino]propyl acetate (54.5 g, 161.1 mmol) was added anhydrous tetrahydrofuran (THF, 1.4 L), followed by 1,1'-thiocarbonyldiimidazole (31.6 g, 177.3 mmol) and the reaction mixture was stirred at 71° C. for 1.5 h. The reaction was cooled to ambient temperature and the solvent was removed under reduced pressure to afford an oil. The oil was dissolved in dichloromethane (1.3 L) and the solution was washed with water (3×600 mL). During each wash a significant amount of precipitate was observed which was isolated to afford 3-(7-bromo-2-thioxo-2,3-dihydro-1H-imidazo[4,5-c]quinolin-1-yl)propyl acetate (28.9 g) as a light brown solid.

Part E

To a round-bottomed flask containing 3-(7-bromo-2-thioxo-2,3-dihydro-1H-imidazo[4,5-c]quinolin-1-yl)propyl acetate (28.9 g, 76.0 mmol) was added water (180 mL), ethanol (180 mL), and ammonium hydroxide (38 mL). The resulting suspension was stirred at ambient temperature. To this suspension was added iodomethane (9.5 mL, 152 mmol), and the reaction was stirred for 2 h. The suspension was filtered through a sintered glass funnel and the residue was washed with diethyl ether and dried under reduced pressure to afford 3-[7-bromo-2-(methylthio)-1H-imidazo[4,5-c]quinolin-1-yl]propyl acetate (22.2 g) as tan solid.

Part F

To a round-bottomed flask containing 3-[7-bromo-2-(methylthio)-1H-imidazo[4,5-c]quinolin-1-yl]propyl acetate (22.2 g, 56.3 mmol) was added glacial acetic acid (325 mL) followed by a solution of potassium permanganate (18.0 g, 113.9 mmol, in water (825 mL)). The reaction was stirred at ambient temperature for 4 h after which NaHSO$_3$ (32 g) was added followed by water (1 L). The reaction was transferred to separatory funnel and the aqueous layer was extracted with dichloromethane (2×1 L). The dichloromethane layers were combined and washed with water (2×800 mL) and saturated aqueous sodium bicarbonate (2×800 mL). The organic layer was dried (MgSO$_4$), filtered, and the solvent evaporated to afford crude product with some residual starting material (21.8 g) as a beige solid. The above oxidation procedure was repeated using a small amount of potassium permanganate (2.0 g, 12.7 mmol). The workup procedure described above afforded 3-[7-bromo-2-(methylsulfonyl)-1H-imidazo[4,5-c]quinolin-1-yl]propyl acetate (18.8 g) as a light tan solid.

Part G

To a round-bottomed flask containing 3-[7-bromo-2-(methylsulfonyl)-1H-imidazo[4,5-c]quinolin-1-yl]propyl acetate (15.7 g, 36.8 mmol) was added 2 N NaOH (300 mL) and the reaction was stirred at ambient temperature for 72 h. To the stirred reaction mixture was added additional 2 N NaOH (80 mL) and after 2 h more 2 N NaOH (100 mL) was added. After 1 h the reaction was diluted with water (1.1 L) and transferred to a separatory funnel. The aqueous layer was extracted with dichloromethane (3×800 mL). The aqueous layer was then extracted with ethyl acetate (3×800 mL) and the ethyl acetate extracts were combined, dried (MgSO$_4$), filtered, and the solvent evaporated to afford a solid. The solid was washed with diethyl ether to afford 3-bromo-10,11-dihydro-9H-[1,3]oxazino[3',2':1,2]imidazo[4,5-c]quinoline (3.41 g) as a white solid. The dichloromethane extracts were combined and concentrated under reduced pressure. The residue was treated with 2 N NaOH to afford additional product.

Part H

To a round-bottomed flask containing 3-bromo-10,11-dihydro-9H-[1,3]oxazino[3',2':1,2]imidazo[4,5-c]quinoline (7.0 g, 23.0 mmol) was added chloroform (250 mL) followed by 3-chloroperoxybenzoic acid (77%, 12.9 g). The reaction was stirred at ambient temperature. After 1 h the solvent was reduced by about 20% under reduced pressure and to the reaction was added ammonium hydroxide (105 mL) followed by p-toluenesulfonyl chloride (7.9 g, 41.4 mmol). The reaction was stirred at ambient temperature for 30 minutes. The reaction was diluted with additional chloroform (700 mL) and transferred to a separatory funnel. The organic layer was washed with water (6×700 mL). During the washes solids were observed and they were isolated by filtration to afford a light pink material (1.23 g). This material was purified by automated flash chromatography (ISCO Combiflash Separation System, Biotage column, eluted with a gradient of 0-6% methanol in dichloromethane with 1% ammonium hydroxide). The cleanest fractions were combined and the solvent evaporated to afford 3-bromo-10,11-dihydro-9H-[1,3]oxazino[3',2':1,2]imidazo[4,5-c]quinolin-6-amine (120 mg) as a light tan solid, m.p. 273-276° C.; MS (ESI) m/z 320 (M+H)$^+$. Anal. Calcd for C$_{13}$H$_{11}$BrN$_4$O.0.50 H$_2$O: C, 47.58; H, 3.69; N, 17.07. Found: C, 47.97; H, 3.73; N, 16.60. Additional product was isolated from the organic layer.

Examples 8-12

A solution of 10-methyl-9,10-dihydro-8H-imidazo[1',2':1,2]imidazo[4,5-c]quinolin-6-amine (24 mg, 0.10 mmol, 1 eq) and N,N-diisopropylethylamine (2 eq) in N,N-dimethylacetamide (1 mL) was added to a test tube containing a reagent (1.1 eq) from the table below. The reaction mixture was vortexed overnight, quenched with water (2 drops), and then the solvent was removed by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the reagent used for each example, the structure of the resulting compound, and the observed accurate mass for the isolated trifluoroacetate salt.

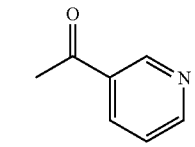

| Example | Reagent | R | Measured Mass (M + H) |
|---|---|---|---|
| 8 | Nicotinoyl chloride hydrochloride | 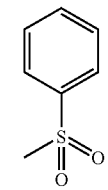 | 345.1460 |
| 9 | Benzenesulfonyl chloride | 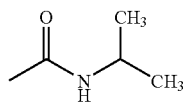 | 380.1200 |
| 10 | Isopropyl isocyanate | 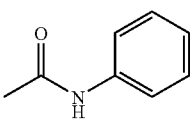 | 325.1797 |
| 11 | Phenyl isocyanate | 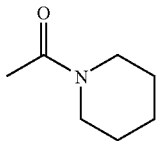 | 359.1614 |
| 12 | 1-Piperidinecarbonyl chloride | | 351.1957 |

Examples 13-21

A solution of 10-methyl-9,10-dihydro-8H-imidazo[1',2':1,2]imidazo[4,5-c]quinolin-6-amine (25 mg, 0.10 mmol, 1 eq) in methanol (1 mL) was added to a test tube containing an aldehyde (1.25 eq) from the table below. The reaction mixture was vortexed for 15 minutes. Borane-pyridine complex (1.3 eq) was added and the reaction mixture was vortexed overnight. More aldehyde (1.25 eq) was added and the reaction mixture was vortexed for 15 minutes. More borane-pyridine complex (1.3 eq) was added and the reaction mixture was vortexed overnight. The reaction mixture was quenched with water (2 drops) and the solvent removed by vacuum centrifugation. The compounds were purified using the method described for Examples 8-12. The table below shows the aldehyde used for each example, the structure of the resulting compound, and the observed accurate mass for the isolated trifluoroacetate salt.

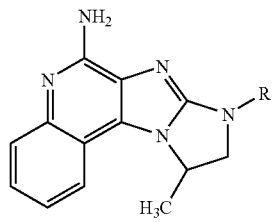

| Example | Reagent | R | Measured Mass (M + H) |
|---|---|---|---|
| 13 | Cyclopropanecarboxaldehyde | —CH₂-cyclopropyl | 294.1705 |
| 14 | Isobutyraldehyde | —CH₂CH(CH₃)₂ | 296.1845 |
| 15 | Butyraldehyde | —CH₂CH₂CH₂CH₃ | 296.1846 |
| 16 | Benzaldehyde | —CH₂-phenyl | 330.1752 |
| 17 | Isonicotinaldehyde | —CH₂-(4-pyridyl) | 331.1645 |
| 18 | Nicotinaldehyde | —CH₂-(3-pyridyl) | 331.1650 |
| 19 | 1-Methyl-2-imidazolecarboxaldehyde | —CH₂-(1-methyl-2-imidazolyl) | 334.1749 |
| 20 | 3-Methoxybenzaldehyde | —CH₂-(3-methoxyphenyl) | 360.1839 |
| 21 | 3-Chlorobenzaldehyde | —CH₂-(3-chlorophenyl) | 364.1328 |

Example 22

10,10-Dimethyl-8,9,10,11-tetrahydropyrimido[1',2': 1,2]imidazo[4,5-c]quinolin-6-amine

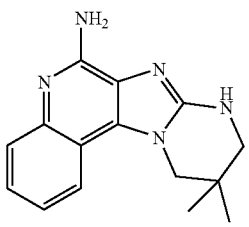

Part A 2,2-Dimethyl-1,3-propanediamine (143.75 mL, 1.197 mol) was dissolved in 600 mL of $CH_2Cl_2$ and cooled to 0° C. under an atmosphere of $N_2$. The clear solution was treated with 3-chloro-4-nitroquinoline (50.0 g, 0.239 mol) suspended in 400 mL of $CH_2Cl_2$. The second solution was slowly added into the first via cannula over the next hour. The remaining solid was then resuspended in 300 mL of $CH_2Cl_2$ and slowly added to the reaction until all of the solids were added. The reaction was then allowed to warm to ambient temperature over the next 4 hours. It was then treated with saturated sodium bicarbonate solution (2×750 mL), followed by brine (750 mL). The organic layer was dried over $Na_2SO_4$, filtered, and concentrated under reduced pressure to give 2,2-dimethyl-$N^1$-(3-nitroquinolin-4-yl)propane-1,3-diamine (64.12 g) as a fluffy yellow solid.

Part B 2,2-Dimethyl-$N^1$-(3-nitroquinolin-4-yl)propane-1,3-diamine (20.0 g, 72.9 mmol) was suspended in 250 mL of THF, and treated with an aqueous solution of NaOH (3.40 g, 85.0 mmol in 100 mL $H_2O$), under an atmosphere of $N_2$. A solution of di-tert-butyl dicarbonate (17.50 g, 80.2 mmol) in 150 mL THF was added into the reaction via cannula over 45 minutes. The reaction continued to stir for an additional hour before the solvent was removed under reduced pressure. The residue was partitioned between 400 mL of $CH_2Cl_2$ and 300 mL of $H_2O$. The organic layer was washed again with 300 mL of water, then with 300 mL of brine. It was then dried over $Na_2SO_4$, filtered, and concentrated under reduced pressure to give a yellow solid. Purification was accomplished by taking the material up in a minimum amount of $CH_2Cl_2$ and adding ~1000 mL of hexanes until a yellow precipitate formed. The solid was filtered off, washed with hexanes, and dried under vacuum to give tert-butyl 2,2-dimethyl-3-[(3-nitroquinolin-4-yl)amino]propylcarbamate as a bright yellow powder (24.73 g).

Part C

A pressure bottle was charged with platinum on carbon (5%, 0.70 g) followed by tert-butyl 2,2-dimethyl-3-[(3-nitroquinolin-4-yl)amino]propylcarbamate dissolved in 250 mL of toluene. The reaction mixture was shaken under $H_2$ at 48 PSI (3.3×10$^5$ Pa). The next day, the reaction mixture was carefully charged with 25 mL of MeOH and filtered through a pad of CELITE filter agent. The pad was rinsed with 1:1 $CH_2Cl_2$/methanol. The solvent was removed under reduced pressure to give tert-butyl 3-[(3-aminoquinolin-4-yl)amino]-2,2-dimethylpropylcarbamate as a light yellow solid.

Part D tert-Butyl 3-[(3-aminoquinolin-4-yl)amino]-2,2-dimethylpropylcarbamate (7.16 g, 20.8 mmol) was suspended in 200 mL of $CH_2Cl_2$ and treated with 1,1'-thiocarbonyldiimidazole (4.07 g, 22.9 mmol) under an atmosphere of $N_2$. After about 2 hours a precipitate had formed. It was isolated by filtration and dried under vacuum to afford tert-butyl 2,2-dimethyl-3-(2-thioxo-2,3-dihydro-1H-imidazo[4,5-c]quinolin-1-yl)propylcarbamate (7.78 g) as a white solid.

Part E

A suspension of tert-butyl 2,2-dimethyl-3-(2-thioxo-2,3-dihydro-1H-imidazo[4,5-c]quinolin-1-yl)propylcarbamate (7.78 g, 20.1 mmol) and 100 mL of 1:1 water/ethanol was treated with 20 mL of concentrated ammonium hydroxide and iodomethane (1.50 mL, 24.2 mmol). Two hours later an additional 50 mL of $H_2O$ was added, and the precipitate was filtered and rinsed with ether. When the ether was added, the funnel became clogged, so the precipitate was transferred into a flask with the aid of methanol and $CH_2Cl_2$. The solvents were removed under reduced pressure to give a light yellow solid. The filtrate was then concentrated under reduced pressure to ~150 mL of mostly water. Organic material was extracted from this solution using $CH_2Cl_2$ (3×). The combined organic layers were washed with brine, dried over $Na_2SO_4$, filtered, combined with the precipitated material, and concentrated under reduced pressure to give tert-butyl 2,2-dimethyl-3-[2-(methylthio)-1H-imidazo[4,5-c]quinolin-1-yl]propylcarbamate (7.81 g) as a light yellow solid.

Part F tert-Butyl 2,2-dimethyl-3-[2-(methylthio)-1H-imidazo[4,5-c]quinolin-1-yl]propylcarbamate (7.81 g, 19.5 mmol) was dissolved in 100 mL of acetic acid and slowly treated with an aqueous solution of potassium permanganate (5.23 g, 33.1 mmol). The next day, sodium bisulfite (5.0 g, 48.8 mmol) was added to the reaction turning it from brown to pale yellow within two minutes. The reaction was concentrated to 50 mL, and then diluted with 50 mL of water. Organic material was extracted with $CH_2Cl_2$ and a small amount of methanol (2×). The pH of the aqueous layer was slowly adjusted to 6 using sodium bicarbonate, and extracted with $CH_2Cl_2$ (3×). The combined organic layers were washed with brine, dried over $Na_2SO_4$, filtered, and concentrated under reduced pressure to give a light yellow foam (7.81 g). Chromatography ($SiO_2$, 0-15% CMA/CHCl$_3$) gave tert-butyl 2,2-dimethyl-3-[2-(methylsulfonyl)-1H-imidazo[4,5-c]quinolin-1-yl]propylcarbamate (5.36 g) as an off white foam.

Part G

A solution of 50 mL of trifluoroacetic acid and tert-butyl 2,2-dimethyl-3-[2-(methylsulfonyl)-1H-imidazo[4,5-c]quinolin-1-yl]propylcarbamate (4.86 g, 11.2 mmol) was allowed to stir at ambient temperatures over the weekend. The solvent was removed under reduced pressure, and the resulting orange residue was taken up in ~100 mL aqueous ammonium hydroxide (pH ~11). After one hour, the solution was extracted with $CH_2Cl_2$. A significant amount of solid stayed in the aqueous layer, was filtered, and dried under vacuum to give 2.01 g of the desired material. The aqueous layer was then extracted again with $CH_2Cl_2$ (2×). The combined organic layers were washed with brine, dried over $Na_2SO_4$, filtered, and concentrated under reduced pressure to give an off white solid (0.45 g). The combined solids were recrystallized from isopropanol to yield 10,10-dimethyl-8,9,10,11-tetrahydropyrimido[1',2':1,2]imidazo[4,5-c]quinoline (1.45 g) as a white solid, m.p. 326-330° C.

$^1$H NMR (300 MHz, DMSO-d$_6$) δ 8.82 (s, 1H), 8.28 (m, 1H), 8.01 (m, 1H), 7.57-7.51 (m, 3H), 4.32 (s, 2H), 3.11 (m, 2H), 1.12 (s, 6H); $^{13}$C NMR (75 MHz, DMSO-d$_6$) δ 152.2, 142.9, 141.3, 136.7, 132.0, 130.3, 125.7, 125.1, 120.4, 117.2, 55.0, 49.8, 28.9, 24.2; MS (APCI) m/z 253 (M+H)+. Anal. calcd for $C_{15}H_{16}N_4$: C, 71.40; H, 6.39; N, 22.20. Found: C, 71.54; H, 6.33; N, 22.15.

Part H

A solution of 10,10-dimethyl-8,9,10,11-tetrahydropyrimido[1',2':1,2]imidazo[4,5-c]quinoline (100 mg, 0.40 mmol) in 10 mL $CHCl_3$ was treated with 3-chloroperoxybenzoic acid (MCPBA) (110 mg, 77% max). The next day, the reaction was treated with 2 mL of concentrated ammonium hydroxide and stirred vigorously. Then p-toluenesulfonyl chloride (76 mg, 0.40 mmol) was carefully added. The following day, the reaction was treated with 5 mL of water and the layers were separated. The organic layer was treated with saturated sodium bicarbonate solution (2×) then washed with brine, dried over $Na_2SO_4$, filtered, and concentrated under reduced pressure to give a brown solid. Chromatography ($SiO_2$, 15-30% $CMA/CHCl_3$) gave recovered starting material (30 mg) and 10,10-dimethyl-8,9,10,11-tetrahydropyrimido[1',2':1,2]imidazo[4,5-c]quinolin-6-amine (30 mg) as a tan solid, decomposed above 230° C.

$^1$H NMR (300 MHz, DMSO-$d_6$) δ 7.98 (d, J=7.1 Hz, 1H), 7.55 (m, 1H), 7.29-7.15 (m, 3H), 6.05 (s, 2H), 4.22 (s, 2H), 3.07 (d, J=2.4 Hz, 2H), 1.11 (s, 6H); MS (ESI) m/z 268 (M+H)+. Anal. calcd for $C_{15}H_{17}N_5 \cdot 0.33H_2O$: C, 65.93; H, 6.51; N, 25.63. Found: C, 65.91; H, 6.25; N, 25.42.

Example 23

(10S)-10-Methyl-9,10-dihydro-8H-imidazo[1',2':1,2] imidazo[4,5-c]quinoline

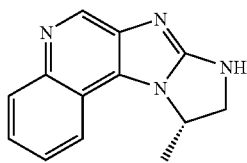

Part A (S)-(-)-1,2-Diaminopropane dihydrochloride (6.94 g, 47.2 mmol) was suspended in 300 mL of dry $CH_2Cl_2$, treated with 1,8-diaxabicyclo[5,4,0]undec-7-ene (15.5 mL, 103.8 mmol), and cooled to 0° C. under an atmosphere of $N_2$. Di-tert-butyl dicarbonate (10.29 g, 47.2 mmol) was dissolved in 100 mL of dry $CH_2Cl_2$ and was slowly added into the reaction via cannula. The reaction was kept cool for another hour before allowing it to warm to ambient temperature overnight. The reaction was then treated with 200 mL of acetic acid (10%), and the layers were separated. The organic layer was dried over $Na_2SO_4$, filtered, and concentrated under reduced pressure to give a white solid (5.51 g). This material was suspended in 50 mL of HCl/ethanol (3.0 M) and heated to 60° C. for 30 minutes. The solution was allowed to cool to ambient temperature, and the white precipitate was filtered off to cleanly give back (S)-(-)-1,2-diaminopropane dihydrochloride (2.00 g, 13.6 mmol). This material was resubmitted to the reaction conditions, and the aqueous phases from both reactions were combined and made basic with concentrated ammonium hydroxide, until the pH ~11. The aqueous layer was extracted with $CH_2Cl_2$ (6×150 mL). The combined organic layers were washed with brine and dried over $Na_2SO_4$, filtered, and concentrated under reduced pressure to give a light yellow oil (2.40 g). Chromatography ($SiO_2$, 40-60% $CMA/CHCl_3$) afforded tert-butyl (2S)-2-aminopropylcarbamate (2.14 g) as a light yellow oil.

Part B

A solution of tert-butyl (2S)-2-aminopropylcarbamate (2.14 g, 12.28 mmol) in 120 mL of dry $CH_2Cl_2$ was cooled to 0° C. and treated with 3-chloro-4-nitroquinoline (2.56 g, 12.28 mmol) and triethylamine (3.4 mL, 25 mmol) under an atmosphere of $N_2$. The reaction was allowed to slowly warm to ambient temperature overnight. It was then treated with 100 mL of $H_2O$ (2×) followed by brine. The organic layer was dried over $Na_2SO_4$, filtered, and concentrated under reduced pressure to give tert-butyl (2S)-2-[(3-nitroquinolin-4-yl) amino]propylcarbamate (4.10 g) as a bright yellow solid.

Part C

The title compound was prepared from tert-butyl (2S)-2-[(3-nitroquinolin-4-yl)amino]propylcarbamate according to the methods of Parts C through G of Example 22 with the following modifications. Part C was carried out in acetonitrile as the solvent. Part D required chromatography ($SiO_2$, 0-6% methanol/$CH_2Cl_2$). Following chromatographic purification ($SiO_2$, 20-40% $CMA/CHCl_3$) in Part G, the title compound, (10S)-10-methyl-9,10-dihydro-8H-imidazo[1',2':1,2]imidazo[4,5-c]quinoline (2.14 g), was obtained as an off white foam.

$^1$H NMR (300 MHz, $CDCl_3$) δ 9.01 (s, 1H), 8.16 (d, J=8.5 Hz, 1H), 7.71 (m, 1H), 7.58-7.44 (m, 2H), 7.28 (br s, 1H), 4.89 (m, 1H), 4.44 (m, 1H), 3.85 (dd, J=9.2, 2.2 Hz, 1H), 1.59 (d, J=6.4 Hz, 3H); MS (APCI) m/z 225 (M+H)+.

Example 24

10-Methyl-8,9,10,11-tetrahydropyridazino[1',6':1,2] imidazo[4,5-c]quinolin-6-amine

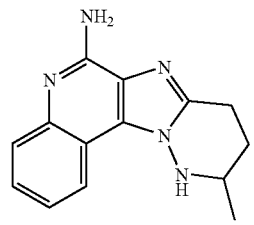

Part A

A mixture of ethyl levulinate (58.4 g, 400 mmol), ethylene glycol (75.4 g, 1.21 mol), pyridinium p-toluenesulfonate (0.10 g, 0.41 mmol) and toluene (200 mL) was heated to reflux while collecting the condensed vapors with a Dean-Stark trap. The trap was emptied every 15 min, collecting 200 mL of liquid total. After 2 h, the reaction mixture was cooled to ambient temperature and concentrated under reduced pressure to give an oil. The oil was dissolved in ethyl acetate (200 mL), washed with water (3×50 mL), saturated $NaHCO_3$ aqueous solution (50 mL), and brine (50 mL), dried over $Na_2SO_4$, and concentrated under reduced pressure to yield 68.9 g of ethyl 3-(2-methyl-1,3-dioxolan-2-yl)propanonate as a yellow oil.

Part B

A solution of ethyl 3-(2-methyl-1,3-dioxolan-2-yl)propanonate (68.9 g, 366 mmol) in methanol (73 mL) was chilled in an ice-water bath. A solution of NaOH (14.64 g, 366 mmol) in water (73 mL) was added drop-wise over 3 min. The reaction was allowed to warm to ambient temperature. After stirring for 17 h, the reaction mixture was concentrated under reduced pressure to remove the methanol. The aqueous solution was diluted with water (400 mL) and washed with ethyl acetate (150 mL). The aqueous solution was chilled in an ice-water bath and then treated drop-wise with $H_2SO_4$ (180 mL of a 1 M aqueous solution) until the pH of the liquid was 2. The aqueous solution was extracted with ethyl acetate (2×150 mL). The organic extracts were washed with brine (50 mL), dried over $Na_2SO_4$, filtered, and concentrated under reduced pressure to yield 38.6 g of 3-(2-methyl-1,3-dioxolan-2-yl)propanoic acid as a yellow oil.

Part C

A mixture of tert-butyl N'-(3-nitroquinolin-4-yl)hydrazinecarboxylate (5.00 g, 16.4 mmol) and 5% platinum on carbon (0.50 g) in acetonitrile (90 mL) and methanol (30 mL) was shaken under hydrogen pressure on a Parr apparatus. When the reaction was complete, the mixture was filtered through a layer of CELITE filter agent. The filter cake was rinsed with 3:1 acetonitrile:methanol. The filtrate was concentrated under reduced pressure to yield 4.50 g of crude tert-butyl N'-(3-aminoquinolin-4-yl)hydrazinecarboxylate as a yellow solid.

Part D

A mixture of tert-butyl N'-(3-aminoquinolin-4-yl)hydrazinecarboxylate (4.50 g, 16.4 mmol), 1-[3-(dimethylamino)propyl]-3-ethylcarbodiimide hydrochloride (3.93 g, 20.5 mmol), 4-methylmorpholine (2.29 mL, 20.5 mmol), and 4-dimethylaminopyridine (0.100 g, 0.82 mmol) in pyridine (120 mL) was chilled to 0° C. under an atmosphere of nitrogen. The mixture was treated drop-wise with a solution of 3-(2-methyl-[1,3]dioxolan-2-yl)-propionic acid (3.28 g, 20.5 mmol) in pyridine (30 mL). The reaction mixture was allowed to slowly come to ambient temperature. After 18 h, the reaction mixture was concentrated under reduced pressure to give a dark red oil. The oil was dissolved in chloroform (150 mL) and washed with 5% $Na_2CO_3$ aqueous solution (2×50 mL) and brine (50 mL), dried over $Na_2SO_4$, filtered, and concentrated under reduced pressure to yield 6.83 g of crude tert-butyl 2-(3-{[3-(2-methyl-1,3-dioxolan-2-yl)propanoyl]amino}quinolin-4-yl)hydrazinecarboxylate as a dark red oil.

Part E

A solution of tert-butyl 2-(3-{[3-(2-methyl-1,3-dioxolan-2-yl)propanoyl]amino}quinolin-4-yl)hydrazinecarboxylate (6.83 g, 16.4 mmol) and pyridinium p-toluenesulfonate (0.10 g, 0.41 mmol) in 1-butanol (125 mL) was heated to 140° C. under an atmosphere of nitrogen. After 3 h, the reaction mixture was cooled to ambient temperature, treated with HCl (38 mL, 4.3 M in ethanol) and heated (115° C.). After 1 h, the reaction mixture was concentrated under reduced pressure to give a brown solid. The solid was dissolved in water (50 mL) and treated with 50% NaOH aqueous solution until the pH of the liquid was 13. A tan solid was collected by vacuum filtration. The solid was dissolved in dichloromethane (150 mL) and washed with water (2×30 mL) and brine (30 mL), dried over $Na_2SO_4$, filtered, and concentrated under reduced pressure to yield 1.96 g of 10-methyl-8,9-dihydropyridazino[1',6':1,2]imidazo[4,5-c]quinoline as a light brown solid.

Part F

A solution of 10-methyl-8,9-dihydropyridazino[1',6':1,2]imidazo[4,5-c]quinoline (1.96 g, 8.30 mmol) in methanol (50 mL) was cooled to 0° C. The solution was treated with $NaBH_4$ (1.26 g, 33.2 mmol) over 3 min. The reaction was allowed to come to ambient temperature over 3 h. The reaction was quenched with slow addition of saturated $NH_4Cl$ aqueous solution (20 mL) and then concentrated under reduced pressure to remove the methanol. The residual material was partitioned between chloroform (75 mL) and 10% $Na_2CO_3$ aqueous solution (25 mL) and then separated. The organic portion was washed with water (25 mL) and brine (25 mL), dried over $Na_2SO_4$, filtered, and concentrated under reduced pressure to give a tan solid. Purification by column chromatography (100 g silica gel eluted with 95:5 chloroform:methanol) yielded 1.56 g of 10-methyl-8,9,10,11-tetrahydropyridazino[1',6':1,2]imidazo[4,5-c]quinoline as a tan solid.

Part G

A solution of 10-methyl-8,9,10,11-tetrahydropyridazino[1',6':1,2]imidazo[4,5-c]quinoline (1.56 g, 6.55 mmol) in chloroform (50 mL) was chilled in a cold water bath and treated with 3-chloroperoxybenzoic acid (2.35 g, 8.18 mmol, 70%). After 30 min, the reaction mixture was treated with concentrated $NH_4OH$ (25 mL), stirred rapidly to homogenize, and then treated with p-toluenesulfonyl chloride (1.31 g, 6.88 mmol). After 20 min, the mixture was diluted with chloroform (25 mL) and water (25 mL) transferred to a separatory funnel and separated. The organic portion was washed with 10% $Na_2CO_3$ aqueous solution (25 mL), water (25 mL) and brine (25 mL), dried over $Na_2SO_4$, filtered, and concentrated under reduced pressure to yield a tan solid. The solid was purified by column chromatography (50 g silica gel eluted with 95:5 chloroform:methanol) to give an off white solid. The solid then was dissolved in 85:15 chloroform:methanol, stirred with activated carbon (0.100 g, Darco G-60), filtered through layer of CELITE filter agent, and concentrated under reduced pressure to yield 0.079 g of 10-methyl-8,9,10,11-tetrahydropyridazino[1',6':1,2]imidazo[4,5-c]quinolin-6-amine as an off white solid, mp 241-243° C.; $^1H$ NMR (300 MHz, DMSO-$d_6$) δ 8.52 (dd, J=8.1, 1.3 Hz, 1H), 7.53 (dd, J=8.3, 1.5 Hz, 1H), 7.39-7.34 (m, 1H), 7.21-7.15 (m, 1H), 6.68 (d, J=10.5 Hz, 1H), 6.46 (s, 2H), 3.44-3.31 (m, 1H), 3.14-3.08 (m, 2H), 2.14-2.07 (m, 1H), 1.79-1.66 (m, 1 H), 1.27 (d, J=6.6 Hz, 3H); $^{13}C$ NMR (75 MHz, DMSO-$d_6$) δ 151.4, 144.3, 143.9, 129.9, 126.1, 125.2, 123.3, 121.1, 120.2, 114.8, 50.4, 27.3, 22.2, 18.2; MS (APCI) m/z 254 $(M+H)^+$.

Example 25

10-[(4-Methylphenyl)sulfonyl]-10H-pyrazolo[1',5':1,2]imidazo[4,5-c]quinolin-6-amine

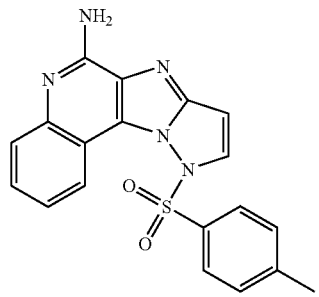

Part A

Small pellets of solid NaOH (5.00 g, 125 mmol) were slowly added to a mixture of ethyl 3,3-diethoxypropionate (19.02 g, 100 mmol) and water (35 mL). As the NaOH dissolved the mixture became a homogeneous solution. The solution was heated to 110° C. for 30 min. The reaction was allowed to cool to ambient temperature and then chilled with an ice-water bath. The solution was acidified with drop-wise addition of concentrated aqueous HCl (9.37 mL, 113 mmol). The solution was allowed to warm to ambient temperature and then extracted with dichloromethane (4×15 mL). The combined organic extracts were washed with brine (15 mL), dried over MgSO$_4$, filtered, and concentrated under reduced pressure to yield 15.11 g of 3,3-diethoxypropionic acid as a yellow oil.

Part B

A mixture of tert-butyl N'-(3-aminoquinolin-4-yl)hydrazinecarboxylate (9.01 g, 32.9 mmol), 1-[3-(dimethylamino)propyl]-3-ethylcarbodiimide hydrochloride (7.56 g, 39.4 mmol), 4-methylmorpholine (4.34 mL, 39.4 mmol), and 4-dimethylaminopyridine (0.200 g, 1.64 mmol) in pyridine (200 mL) was chilled in an ice-water under a nitrogen atmosphere. The mixture was treated drop-wise with a solution of 3,3-diethoxypropionic acid (6.40 g, 39.4 mmol) in pyridine (50 mL). The reaction was allowed to slowly come to ambient temperature and stirred overnight. After 15 h, the reaction mixture was concentrated under reduced pressure to yield a dark red solid. The solid was dissolved in chloroform (150 mL) and transferred to a separatory funnel. The organic solution was washed with 10% Na$_2$CO$_3$ aqueous solution (35 mL), water (2×35 mL), and brine (35 mL), dried over Na$_2$SO$_4$, filtered, and concentrated under reduced pressure to yield 13.75 g of crude tert-butyl N'-[3-(3,3-diethoxypropionylamino)quinolin-4-yl]hydrazinecarboxylate as a dark red solid.

Part C

A solution of tert-butyl N'-[3-(3,3-diethoxypropionylamino)quinolin-4-yl]-hydrazinecarboxylate (13.75 g, 32.9 mmol) and pyridinium p-toluenesulfonate (0.206 g, 0.082 mmol) in 1-propanol (250 mL) was placed under a nitrogen atmosphere and heated to 125° C. After 4 h, the reaction was cooled to ambient temperature and concentrated under reduced pressure to yield a dark red oily solid. This material was suspended in HCl (55 mL, 3 M in ethanol) and heated to 100° C. After 1.5 h, the reaction mix was cooled to ambient temperature and concentrated under reduced pressure to give a brown solid. The solid was suspended in water (50 mL), stirred vigorously, and neutralized with drop-wise addition of 10% NaOH aqueous solution until the pH of the liquid was 8. The aqueous mixture was transferred to a separatory funnel and extracted with chloroform (4×25 mL). The combined organic extracts were concentrated under reduced pressure to give a dark red solid. This solid was purified by prep. HPLC (350 g silica gel eluted with 1-20% CMA in chloroform) to give a dark red solid. This material was triturated with ether (75 mL) and filtered to yield 2.31 g of 10H-pyrazolo[1',5':1,2]imidazo[4,5-c]quinoline as a red solid.

Part D

A solution of 10H-pyrazolo[1',5':1,2]imidazo[4,5-c]quinoline (1.00 g, 4.80 mmol) in tetrahydrofuran (24 mL), under a nitrogen atmosphere, was chilled in an ice-water bath. The solution was treated with NaH (0.29 g, 7.20 mmol, 60%) in small portions over 2 min. After 10 min, the mixture was treated with p-toluenesulfonyl chloride (1.01 g, 5.28 mmol), and allowed to come to ambient temperature. After 1.5 h the reaction was quenched with slow addition of water (5 mL). The reaction mixture was concentrated under reduced pressure to yield a brown solid. The solid was purified by prep. HPLC (100 g silica gel eluted with 1-10% CMA in chloroform) to give a tan foam. The foam was dissolved in methyl tert-butyl ether (25 mL) and filtered through filter paper. The filtrate was concentrated under reduced pressure to yield 0.49 g of 10-[(4-methylphenyl)sulfonyl]-10H-pyrazolo[1',5':1,2]imidazo[4,5-c]quinoline as a tan solid.

Part E

A solution of 10-[(4-methylphenyl)sulfonyl]-10H-pyrazolo[1',5':1,2]imidazo[4,5-c]quinoline (0.55 g, 1.5 mmol) in 1,2-dichloroethane (15 mL) was placed in a 48 mL heavy wall glass pressure flask and treated with 3-chloroperoxybenzoic acid (0.56 g, 2.3 mmol). After 1.5 h the reaction was treated with concentrated NH$_4$OH (5 mL, 30%); the flask was sealed and heated to 70° C. Once at temperature, p-toluenesulfonyl chloride (0.31 g, 1.7 mmol) was quickly added, the flask was resealed and heated to 75° C. After 1 h additional NH$_4$OH (1 mL) and p-toluenesulfonyl chloride (50 mg) were added and the flask heated for another hour. After 2 h total, the flask was cooled to ambient temperature, and the reaction mixture was diluted with chloroform (15 mL) and water (10 mL). The phases were separated and the organic portion was washed with 10% Na$_2$CO$_3$ aqueous solution (10 mL) and water (10 mL). The combined aqueous washes were back-extracted with chloroform (20 mL). The combined organic extracts were washed with brine (10 mL), dried over Na$_2$SO$_4$, filtered, and concentrated under reduced pressure to yield an orange solid. The solid was recrystallized twice from acetonitrile to yield 0.14 g of 10-[(4-methylphenyl)sulfonyl]-10H-pyrazolo [1',5':1,2]imidazo[4,5-c]quinolin-6-amine as tan crystals, mp 204-206° C.; $^1$H NMR (500 MHz, DMSO-d$_6$) δ 8.55-8.53 (m, 1H), 8.13 (d, J=2.3 Hz, 1H), 7.68-7.67 (m, 2H), 7.66-7.64 (m, 2H), 7.41-7.389 (m, 1H), 7.35 (d, J=8.2 Hz, 2H), 7.24 (s, 2H), 6.64 (d, J=2.0 Hz, 1H), 3.29 (s, 3H); $^{13}$C NMR (125 MHz, DMSO-d$_6$) δ 148.1, 147.6, 147.4, 142.8, 131.7, 131.3, 131.0, 130.9, 128.4, 127.2, 125.9, 125.5, 123.4, 122.7, 111.3, 90.8, 21.5; MS (APCI) m/z 378.06 (M+H)$^+$; Anal. Calcd for C$_{19}$H$_{15}$N$_5$O$_2$S: C, 60.47; H, 4.01; N, 18.56. Found: C, 60.21; H, 3.84; N, 18.52.

Example 26

10H-Pyrazolo[1',5':1,2]imidazo[4,5-c]quinolin-6-amine

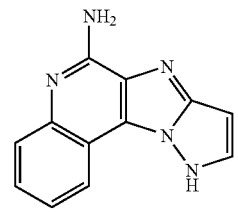

A solution of 10-[(4-methylphenyl)sulfonyl]-10H-pyrazolo[1',5':1,2]imidazo[4,5-c]quinolin-6-amine (0.13 g, 0.34 mmol) and sodium ethoxide (0.032 g, 0.38 mmol) in ethanol (3.5 mL) was heated to 85° C. After 1.5 h, the reaction was cooled to ambient temperature, quenched with silica gel (1.3 g) and concentrated under reduce pressure. The material was loaded onto a 40 g silica gel cartridge and purified by prep. HPLC (eluted with 10-30% CMA in chloroform) to give a red/orange solid. The solid was treated with methyl tert-butyl ether (10 mL) and heated to boiling. The hot mixture was filtered through fine filter paper and the filtrate concentrated to yield 20 mg of 10H-pyrazolo[1',5':1,2]imidazo[4,5-c]quinolin-6-amine as a mauve solid, mp, dec>200° C.; $^1$H NMR (500 MHz, DMSO-d$_6$) δ 11.58 (s, 1H), 8.53 (dd, J=7.9, 1.1 Hz, 1H), 7.93 (d, J=2.1 Hz, 1H), 7.68 (d, J=8.1 Hz, 1H), 7.53-7.50 (m, 1H), 7.41-7.38 (m, 1H), 6.73 (s, 2H), 6.04 (d, J=2.1 Hz, 1H); $^{13}$C NMR (125 MHz, DMSO-d$_6$) δ 147.5, 145.9, 143.5, 143.3, 127.2, 125.8, 123.9, 122.4, 121.2, 117.7, 113.4, 80.4; MS (ESI) m/z 224.22 (M+H)$^+$.

Example 27

(10S)-10-Methyl-9,10-dihydro-8H-imidazo[1',2':1,2]imidazo[4,5-c]quinolin-6-amine

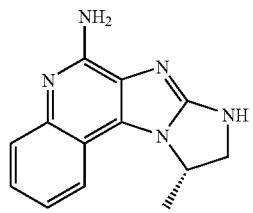

Part A

A suspension of 60 mL of THF and (10S)-10-methyl-9,10-dihydro-8H-imidazo[1',2':1,2]imidazo[4,5-c]quinoline (1.42 g, 6.33 mmol, Example 23) was treated with aqueous NaOH (0.28 g, 6.96 mmol, 5 mL $H_2O$). After five minutes, di-tert-butyl dicarbonate (1.52 g, 6.96 mmol) was added in one portion. The reaction stirred at ambient temperatures for the next 3 days. The solvent was then removed under reduced pressure, and the residue was partitioned between $CH_2Cl_2$ and $H_2O$. The layers were separated, and the organic one was washed again with $H_2O$, then brine; dried over $Na_2SO_4$, filtered and concentrated to give an off-white foam. Chromatography ($SiO_2$, 0-20% CMA/$CHCl_3$) afforded tert-butyl (10S)-10-methyl-9,10-dihydro-8H-imidazo[1',2':1,2]imidazo[4,5-c]quinoline-8-carboxylate (1.16 g) as a white foam.

Part B tert-Butyl (10S)-10-methyl-9,10-dihydro-8H-imidazo[1',2':1,2]imidazo[4,5-c]quinoline-8-carboxylate (1.16 g, 3.58 mmol) was dissolved in 50 mL of $CHCl_3$ and treated with MCPBA (1.05 g, 77% max). After 18 hours, the reaction was treated with 20 mL of 1% $Na_2CO_3$ solution and the layers were separated. The aqueous layer was extracted with $CHCl_3$ (6×20 mL). The combined organic layer was washed with brine, dried over $Na_2SO_4$, filtered and concentrated to give tert-butyl (10S)-10-methyl-9,10-dihydro-8H-imidazo[1',2':1,2]imidazo[4,5-c]quinoline-8-carboxylate 5-oxide (1.22 g) as a brown foam.

Part C

A solution of tert-butyl (10S)-10-methyl-9,10-dihydro-8H-imidazo[1',2':1,2]imidazo[4,5-c]quinoline-8-carboxylate 5-oxide (1.22 g, 3.58 mmol) in 50 mL of $CH_2Cl_2$ was treated with 5 mL of concentrated aqueous ammonium hydroxide and stirred vigorously. p-Toluenesulfonyl chloride (0.68 g, 3.58 mmol) was added in one portion and the reaction became slightly exothermic. The following day the reaction was treated with 5 mL of $H_2O$, and the layers were separated. The organic layer was washed with saturated $NaHCO_3$ solution (2×), then brine. It was dried over $Na_2SO_4$, filtered and concentrated to give a crude solid. Chromatography ($SiO_2$, 0-20% CMA/$CHCl_3$) afforded an off white solid, which was recrystallized from ethyl acetate to give tert-butyl (10S)-6-amino-10-methyl-9,10-dihydro-8H-imidazo[1',2':1,2]imidazo[4,5-c]quinoline-8-carboxylate (0.26 g) as a white solid.

Part D tert-Butyl (10S)-6-amino-10-methyl-9,10-dihydro-8H-imidazo[1',2':1,2]imidazo[4,5-c]quinoline-8-carboxylate (130 mg, 0.383 mmol) was treated with 10 mL of 3.0 M HCl/EtOH and heated up to reflux for about 20 minutes. The volatiles were then removed under reduced pressure, and the resulting residue was partitioned between $CH_2Cl_2$ and $H_2O$. The layers were separated, and the aqueous one was extracted again with $CH_2Cl_2$, and the combined organic layers were discarded. The aqueous layer was then treated with concentrated ammonium hydroxide solution until the pH ~11. The layer was extracted with $CH_2Cl_2$ (3×). The combined organic layer was washed with brine, dried over $Na_2SO_4$, filtered and concentrated to give a white solid. Chromatography ($SiO_2$, 20-40% CMA/$CHCl_3$) afforded (10S)-10-methyl-9,10-dihydro-8H-imidazo[1',2':1,2]imidazo[4,5-c]quinolin-6-amine (55 mg) as an off white solid, m.p. 265-273° C.

$^1$H NMR (500 MHz, DMSO-$d_6$) δ 7.74 (d, J=7.9 Hz, 1H), 7.55 (d, J=8.2 Hz, 1H), 7.33 (m, 1H), 7.20 (m, 2H), 6.92 (s, 1H), 6.14 (s, 2H), 5.09 (m, 1H), 4.21 (m, 1H), 3.66 (d, J=9.5 Hz, 1H), 1.42 (d, J=6.3 Hz, 3H); $^{13}$C NMR (125 MHz, DMSO-$d_6$) δ 160.5, 151.1, 143.3, 130.4, 129.3, 126.1, 125.7, 121.3, 120.2, 114.2, 55.3, 51.7, 20.3; MS (ESI) m/z 240 (M+H)$^+$; Anal. calcd for $C_{13}H_{13}N_5 \cdot 0.30H_2O$: C, 63.81; H, 5.60; N, 28.62. Found: C, 63.58; H, 5.22; N, 28.14.

Example 28

(10R)-10-Methyl-9,10-dihydro-8H-imidazo[1',2':1,2]imidazo[4,5-c]quinolin-6-amine

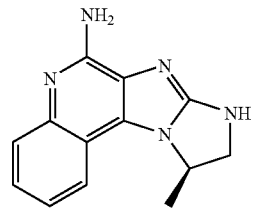

The methods described in Parts A through C of Example 23 were used to prepare (10R)-10-methyl-9,10-dihydro-8H-imidazo[1',2':1,2]imidazo[4,5-c]quinoline with (R)-(−)-1,2-diaminopropane dihydrochloride used in lieu of (S)-(−)-1,2-diaminopropane dihydrochloride in Part A. The methods described in Parts A through D of Example 27 were used to convert (10R)-10-methyl-9,10-dihydro-8H-imidazo[1',2':1,2]imidazo[4,5-c]quinoline to the title compound, which was obtained as a white solid, m.p. 272-274° C.

$^1$H NMR (500 MHz, DMSO-$d_6$) δ 7.74 (d, J=7.9 Hz, 1H), 7.55 (d, J=8.5 Hz, 1H), 7.33 (m, 1H), 7.19 (m, 2H), 6.90 (s, 1H), 6.12 (s, 2H), 5.09 (m, 1H), 4.20 (m, 1H), 3.66 (d, J=9.5 Hz, 1H), 1.42 (d, J=6.3 Hz, 3H); $^{13}$C NMR (125 MHz, DMSO-$d_6$) δ 160.4, 151.2, 143.4, 130.5, 129.2, 126.2, 125.7, 121.2, 120.2, 114.2, 55.3, 51.7, 20.3; MS (ESI) m/z 240 (M+H)$^+$; Anal. calcd for $C_{13}H_{13}N_5$: C, 65.26; H, 5.48; N, 29.27. Found: C, 64.92; H, 5.36; N, 29.17.

Example 29

(11S)-11-Methyl-8,9,10,11-tetrahydropyrimido[1',2': 1,2]imidazo[4,5-c]quinoline

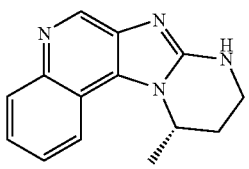

Part A tert-Butyl (1S)-3-amino-1-methylpropylcarbamate (3.01 g, 16.0 mmol), which was prepared using the method of Lebreton et. al., *J. Med. Chem.*, 42, pp. 4749-4763 (1999), was dissolved in a 1:1 solution THF/water and cooled 0° C. The mixture was treated with $Na_2CO_3$ (3.39 g, 32.0 mmol) and followed by benzyl chloroformate (2.50 g, 17.6 mmol), which was added slowly over 5 minutes. The reaction was allowed to slowly warm to room temperature overnight. The layers were separated, and the aqueous phase was extracted with $CH_2Cl_2$ (2×). The combined organic layer was washed with water, saturated $NaHCO_3$ solution and brine. It was then dried over $Na_2SO_4$, filtered and concentrated to give 5.16 g of an off-white solid.

Part B

A solution of 20 mL of $CH_2Cl_2$ and the material from Part A (5.16 g, 16.0 mmol) was treated with 10 mL of trifluoroacetic acid at 0° C. After 30 minutes, the reaction was allowed to warm to room temperature. The solvent was removed under reduced pressure a couple of hours later and the resulting residue dissolved in dilute $NH_4OH$. The aqueous solution was extracted with $CH_2Cl_2$ (3×). The combined organic layers were washed with saturated $NaHCO_3$ solution, and brine; dried over $Na_2SO_4$, filtered and concentrated to give benzyl (3S)-3-aminobutylcarbamate (3.06 g) as a viscous orange oil which crystallized slowly over time.

Part C

Benzyl (3S)-3-aminobutylcarbamate and 3-chloro-4-nitroquinoline were reacted according to the method of Part A of Example 22 to provide benzyl (3R)-3-[(3-nitroquinolin-4-yl)amino]butylcarbamate.

Part D

Sodium borohydride (110 mg, 2.8 mmol) was added to a solution of nickel (II) chloride hexahydrate (330 mg, 1.4 mmol) in 10 mL of methanol. A solution of benzyl (3R)-3-[(3-nitroquinolin-4-yl)amino]butylcarbamate (1.11 g, 2.81 mmol) in 20 mL of 1:1 methanol/dichloromethane was added, and the resulting dark mixture was stirred for 5 minutes at room temperature. Additional sodium borohydride was added in small portions until the reaction solution become colorless. The mixture was filtered through a layer of CELITE filter agent, and the filtrate was concentrated under reduced pressure. The resulting brown solid was triturated with dichloromethane, and the resulting mixture was filtered through a layer of CELITE filter agent. The filtrate was concentrated under reduced pressure to provide 0.96 g of benzyl (3R)-3-[(3-aminoquinolin-4-yl)amino]butylcarbamate as a brown foam.

Part E

The general methods described in Parts D, E, and F of Example 22 were used to convert benzyl (3R)-3-[(3-aminoquinolin-4-yl)amino]butylcarbamate to benzyl (3R)-3-[2-(methylsulfonyl)-1H-imidazo[4,5-c]quinolin-1-yl]butylcarbamate with the modification that product obtained from the method of Part D of Example 22 was purified by column chromatography ($SiO_2$, 10-30% $CMA/CHCl_3$).

Part F

Potassium tert-butoxide (86 mg) was added to a solution of benzyl (3R)-3-[2-(methylsulfonyl)-1H-imidazo[4,5-c]quinolin-1-yl]butylcarbamate (380 mg, 0.84 mmol) in 10 mL of THF. The reaction was stirred for about two hours at room temperature, and an analysis by thin layer chromatography (TLC) indicated the presence of starting material. Additional potassium tert-butoxide (120 mg) was added, and the reaction was stirred over three days at room temperature. $CH_2Cl_2$ (20 mL) and $H_2O$ (20 mL) were added. The layers were separated, and the organic fraction was washed sequentially with saturated $NaHCO_3$ solution and brine, dried over $Na_2SO_4$, filtered, and concentrated under reduced pressure. Chromatography ($SiO_2$, 10-30% $CMA/CHCl_3$) afforded (11S)-11-methyl-8,9,10,11-tetrahydropyrimido[1',2':1,2]imidazo[4,5-c]quinoline (170 mg) as an off white solid.

$^1$H NMR (300 MHz, $CDCl_3$) δ 9.01 (s, 1H), 8.21 (m, 1H), 8.03 (m, 1H), 5.17 (m, 1H), 3.74-3.65 (m, 2H), 2.41 (m, 1H), 2.08 (m, 1H), 1.66 (d, J=6.9 Hz, 3H); MS (ESI) m/z 239 $(M+H)^+$.

Examples 30-54

A solution of 3-bromo-10,11-dihydro-9H-[1,3]oxazino[3', 2':1,2]imidazo[4,5-c]quinolin-6-amine (31.9 mg, 0.10 mmol, Example 7) in 7:3 volume:volume (v:v) dichloromethane: methanol (2 mL) was added to a test tube, and the solvent was removed by vacuum centrifugation. The boronic acid (0.11 mmol) indicated in the table below and n-propanol (1.6 mL) were sequentially added, and the test tube was purged with nitrogen. The reaction mixture was sonicated until it had the consistency of milk. Palladium (II) acetate (0.150 mL of a 0.018 M solution in toluene, 0.0026 mmol), 2M aqueous sodium carbonate solution (600 µL), deionized water (113 µL), and a solution of 0.15 mol % triphenylphosphine in n-propanol (53 µL, 0.0078 mmol) were sequentially added. The test tube was purged with nitrogen, capped, and then heated to 80° C. overnight in a sand bath. For Example 54, glacial acetic acid (0.5 mL), tetrahydrofuran (1 mL), and deionized water (1 mL) were added to the test tube. The reaction was heated for four hours at 60° C. 5-(tert-Butyldimethylsilanyloxymethyl)pyridine-3-boronic acid can be prepared according to the method described in International Publication Number WO/2004/058759 Example 115 Part A.

The contents of each test tube were passed through a Waters Oasis Sample Extractions Cartridge MCX (6 cc) according to the following procedure. Hydrochloric acid (3 mL of 1 N in methanol) was added to adjust each example to pH 5, and the resulting solution was passed through the cartridge optionally using light nitrogen pressure. The cartridge was washed with methanol (5 mL) optionally using light nitrogen pressure and transferred to a clean test tube. A solution of 1 N ammonia in methanol (2×5 mL) was then passed through the cartridge optionally using light nitrogen pressure, and the basic solution was collected and concentrated.

The compounds were purified by reversed phase prep HPLC according to the method described in Examples 8 through 12. The table below shows the reagent used for each example, the structure of the resulting compound, and the observed accurate mass for the isolated trifluoroacetate salt.

Examples 30-54

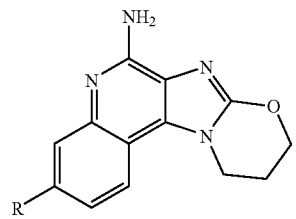

| Example | Reagent | R | Measured Mass (M + H) |
|---|---|---|---|
| 7 | None | Br— | 319.0186 |
| 30 | Phenylboronic acid | phenyl | 317.1374 |
| 31 | Pyridine-3-boronic acid | 3-pyridyl | 318.1331 |
| 32 | 2-Hydroxyphenylboronic acid | 2-hydroxyphenyl | 333.1326 |
| 33 | 3-Hydroxyphenylboronic acid | 3-hydroxyphenyl | 333.1334 |
| 34 | 2-Fluorophenylboronic acid | 2-fluorophenyl | 335.1277 |
| 35 | 3-Fluorophenylboronic acid | 3-fluorophenyl | 335.1284 |
| 36 | 4-Fluorophenylboronic acid | 4-fluorophenyl | 335.1282 |
| 37 | 3-Cyanophenylboronic acid | 3-cyanophenyl | 342.1332 |
| 38 | 2-Methoxyphenylboronic acid | 2-methoxyphenyl | 347.1477 |

-continued

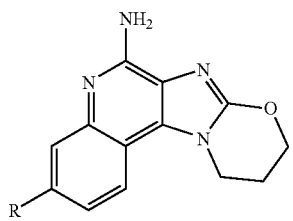

| Example | Reagent | R | Measured Mass (M + H) |
|---|---|---|---|
| 39 | 4-Methoxyphenylboronic acid | 4-methoxyphenyl | 347.1476 |
| 40 | 3-Chlorophenylboronic acid | 3-chlorophenyl | 351.0991 |
| 41 | 2-Chlorophenylboronic acid | 2-chlorophenyl | 351.0979 |
| 42 | 4-Chlorophenylboronic acid | 4-chlorophenyl | 351.0978 |
| 43 | (3-Aminocarbonylphenyl)boronic acid | 3-aminocarbonylphenyl | 360.1454 |
| 44 | [3-(3-Hydroxypropyl)phenyl]boronic acid | 3-(3-hydroxypropyl)phenyl | 375.1822 |
| 45 | 2,4-Dimethoxyphenylboronic acid | 2,4-dimethoxyphenyl | 377.1583 |
| 46 | 2,6-Dimethoxyphenylboronic acid | 2,6-dimethoxyphenyl | 377.1578 |

-continued

| Example | Reagent | R | Measured Mass (M + H) |
|---|---|---|---|
| 47 | 3,4-Dimethoxyphenylboronic acid | 2,3-dimethoxyphenyl | 377.1612 |
| 48 | 4-Borono-DL-phenylalanine | 4-(2-amino-2-carboxyethyl)phenyl | 404.1689 |
| 49 | 4-(Methylsulfonylamino)phenylboronic acid | 4-(methylsulfonylamino)phenyl | 410.1281 |
| 50 | 3-(Pyrrolidine-1-carbonyl)phenylboronic acid | 3-(pyrrolidine-1-carbonyl)phenyl | 414.1924 |
| 51 | 4-(Pyrrolidine-1-carbonyl)phenylboronic acid | 4-(pyrrolidine-1-carbonyl)phenyl | 414.1894 |
| 52 | 3-(Butylaminocarbonyl)phenylboronic acid | 3-(butylaminocarbonyl)phenyl | 416.2059 |
| 53 | 4-(Isobutylaminocarbonyl)phenylboronic acid | 3-(isobutylaminocarbonyl)phenyl | 416.2075 |
| 54 | 5-(tert-Butyldimethylsilanyloxymethyl)pyridine-3-boronic acid | 5-(hydroxymethyl)pyridin-3-yl | 348.1454 |

Example 55

3-Bromo-8,9,10,11-tetrahydropyrimido[1',2':1,2]imidazo[4,5-c]quinolin-6-amine trifluoroacetate

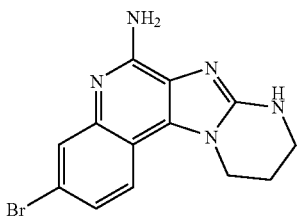

Part A 1,3-Propanediamine (36 mL, 435 mmol) was dissolved in DMF (350 mL) and cooled to approximately 0° C. under an atmosphere of $N_2$. A suspension of 7-bromo-3-chloro-4-nitroquinoline (25 g, 87 mmol) in DMF (150 mL) was then added dropwise over a period of about five hours while the reaction temperature was maintained below 5° C. The reaction was then allowed to warm to room temperature and stirred overnight. The reaction was poured into ice water, and the mixture was stirred vigorously for 15 minutes. A solid was present and was isolated by filtration, air-dried, triturated with diethyl ether, isolated by filtration, and dried overnight under vacuum to provide 24 g of N-(7-bromo-3-nitroquinolin-4-yl)propane-1,3-diamine as a yellow solid.

Part B

A solution of di-tert-butyl dicarbonate (18 g, 81 mmol) in DMF (50 mL) was added dropwise to a solution of N-(7-bromo-3-nitroquinolin-4-yl)propane-1,3-diamine (24 g, 74 mmol) in DMF (150 mL) and triethylamine (21 mL), and the reaction was stirred for about two hours at room temperature and then poured into water. A solid was present and was collected by filtration and purified by column chromatography on silica gel in two portions (first portion elution with a gradient of ethyl acetate in hexanes, second portion elution with a gradient of 2% ammonium hydroxide/methanol in dichloromethane) to provide 17.3 g of tert-butyl 3-[(7-bromo-3-nitroquinolin-4-yl)amino]propylcarbamate.

Part C

A hydrogenation flask was charged with platinum on carbon (5%, 2 g) followed by a solution of tert-butyl 3-[(7-bromo-3-nitroquinolin-4-yl)amino]propylcarbamate in ethyl acetate (200 mL) and dichloromethane (75 mL). The reaction mixture was shaken under $H_2$ at 46 PSI ($3.2 \times 10^5$ Pa) overnight and then filtered through a layer of CELITE filter agent. The filtrate was concentrated under reduced pressure to give 9.3 g of tert-butyl 3-[(3-amino-7-bromoquinolin-4-yl)amino]propylcarbamate.

Part D

A solution of tert-butyl 3-[(3-amino-7-bromoquinolin-4-yl)amino]propylcarbamate (9.3 g, 23.5 mmol) and 1,1'-thiocarbonyldiimidazole (4.6 g, 26 mmol) in THF (250 mL), and the reaction mixture was heated at reflux for two hours. An analysis by liquid chromatography/mass spectrometry (LC/MS) indicated the reaction was incomplete, and additional 1,1'-thiocarbonyldiimidazole (1 g) was added. The reaction was heated at reflux for an additional hour, allowed to cool to room temperature, and concentrated under reduced pressure. The residue was dissolved in water, and the resulting solution was extracted with tert-butyl methyl ether. The combined organic fractions were washed with water, dried over magnesium sulfate, filtered, and concentrated under reduced pressure. The crude product was purified by column chromatography on silica gel (eluting with a gradient of 2% ammonium hydroxide/methanol in dichloromethane) to provide 4 g of tert-butyl 3-(7-bromo-2-thioxo-2,3-dihydro-1H-imidazo[4,5-c]quinolin-1-yl)propylcarbamate.

Part E

Iodomethane (0.89 mL, 14 mmol) was added to a suspension of tert-butyl 3-(7-bromo-2-thioxo-2,3-dihydro-1H-imidazo[4,5-c]quinolin-1-yl)propylcarbamate (4 g, 9 mmol) in deionized water (25 mL), ethanol (25 mL), and ammonium hydroxide (5 mL), and the reaction was stirred for two hours at room temperature and then diluted with chloroform and water. The aqueous layer was separated and extracted four times with chloroform. The combined organic fractions were dried over magnesium sulfate, filtered, and concentrated under reduced pressure. The crude product was dried under high vacuum to provide 2.7 g of tert-butyl 3-(7-bromo-2-(methylthio)-1H-imidazo[4,5-c]quinolin-1-yl)propylcarbamate.

Part F

A solution of potassium permanganate (1.9 g, 12 mmol) in deionized water (90 mL) was added to a solution of tert-butyl 3-(7-bromo-2-(methylthio)-1H-imidazo[4,5-c]quinolin-1-yl)propylcarbamate (2.7 g, 6 mmol) in glacial acetic acid (35 mL), and the reaction was stirred at room temperature overnight. The reaction was diluted with water and treated with sodium bisulfite. The aqueous layer was separated and extracted three times with chloroform. The combined organic fractions were dried over magnesium sulfate, filtered, and concentrated under reduced pressure to provide 2.3 g of tert-butyl 3-(7-bromo-2-(methylsulfonyl)-1H-imidazo[4,5-c]quinolin-1-yl)propylcarbamate.

Part G

Under a nitrogen atmosphere, potassium tert-butoxide (6 mL of a 1 M solution in THF) was added to a solution of tert-butyl 3-(7-bromo-2-(methylsulfonyl)-1H-imidazo[4,5-c]quinolin-1-yl)propylcarbamate (2.3 g, 4.8 mmol) in THF (50 mL). The reaction was stirred overnight at room temperature, and an analysis by LC/MS indicated the presence of starting material. Additional potassium tert-butoxide solution (4 mL) was added, and the reaction was stirred for an additional 30 minutes at room temperature. The reaction was poured into water. A solid was present and was washed with water and dried for three days in a vacuum oven to provide 0.95 g of tert-butyl 3-bromo-10,11-dihydropyrimido[1',2':1,2]imidazo[4,5-c]quinoline-8(9H)-carboxylate.

Part H

MCPBA (800 mg of approximately 60% pure material) was added to a solution of tert-butyl 3-bromo-10,11-dihydropyrimido[1',2':1,2]imidazo[4,5-c]quinoline-8(9H)-carboxylate (940 mg, 2.3 mmol) in chloroform (50 mL). The reaction was stirred for one hour at room temperature, and an analysis by LC/MS indicated the presence of starting material. Additional MCPBA (540 mg) was added, and the reaction was stirred for an additional 30 minutes and then diluted with water and chloroform. The aqueous layer was separated and extracted twice with chloroform. The combined organic fractions were dried over magnesium sulfate, filtered, and concentrated under reduced pressure to provide 0.97 g of tert-butyl 3-bromo-5-oxido-10,11-dihydropyrimido[1',2':1,2]imidazo[4,5-c]quinoline-8(9H)-carboxylate.

Part I p-Toluenesulfonyl chloride (441 mg, 2.3 mmol) was added to a mixture of tert-butyl 3-bromo-5-oxido-10,11-dihydropyrimido[1',2':1,2]imidazo[4,5-c]quinoline-8(9H)-carboxylate (0.97 g, 2.3 mmol), dichloromethane (30 mL), and concentrated ammonium hydroxide (3 mL), and the reaction was stirred overnight at room temperature. Water and dichloromethane were added. The aqueous layer was separated and extracted four times with dichloromethane. The combined organic fractions were dried over magnesium sulfate, filtered, and concentrated under reduced pressure. The crude product was purified by column chromatography on silica gel (eluting with a gradient of 2% ammonium hydroxide/methanol in dichloromethane), and the resulting product was recrystallized from 1,2-dichloroethane and hexanes to provide 0.16 g of tert-butyl 6-amino-3-bromo-10,11-dihydropyrimido[1',2':1,2]imidazo[4,5-c]quinoline-8(9H)-carboxylate.

Part J

Trifluoroacetic acid (4 mL) was added to a solution of tert-butyl 6-amino-3-bromo-10,11-dihydropyrimido[1',2':1,2]imidazo[4,5-c]quinoline-8(9H)-carboxylate (0.16 g) in dichloromethane (0.400 mL), and the resulting solution was stirred for two hours at room temperature. An analysis by LC/MS indicated the presence of starting material, and additional trifluoroacetic acid was added. The reaction was stirred for an additional four hours, concentrated under reduced pressure, and purified according to the method of Examples 8 through 12 to provide 3-bromo-8,9,10,11-tetrahydropyrimido[1',2':1,2]imidazo[4,5-c]quinolin-6-amine trifluoroacetate, observed accurate mass 318.0367 (M+H).

Example 56

9,10-Dihydro-8H-imidazo[1',2':1,2]imidazo[4,5-c][1,5]naphthyridin-6-amine

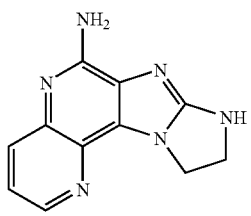

Part A 1,1'-Thiocarbonyldiimidazole (30.6 g, 172 mmol) was added slowly to a mixture of tert-butyl 2-[(3-amino[1,5]naphthyridin-4-yl)amino]ethyl carbamate (U.S. Pat. No. 6,194,425, Example 87, 35 g, 114 mmol) and THF (300 mL). The reaction was stirred for 15 minutes at room temperature, and additional THF was added to facilitate stirring. The reaction was stirred for three hours at room temperature, and then most of the THF was removed under reduced pressure. Water (500 mL) was added, and the resulting solid was isolated by filtration, washed with water and diethyl ether, and dried under high vacuum for one hour to provide 36 g tert-butyl 2-(2-thioxo-2,3-dihydro-1H-imidazo[4,5-c][1,5]naphthyridin-1-yl)ethylcarbamate of as a white solid.

Part B tert-Butyl 2-(2-thioxo-2,3-dihydro-1H-imidazo[4,5-c][1,5]naphthyridin-1-yl)ethylcarbamate (31 g, 89.8 mmol) in water (150 mL) and ethanol (150 mL) was treated with ammonium hydroxide (30 mL) and iodomethane (25.5 g, 180 mmol) according to the general method of Part E of Example 22. After three hours, most of the ethanol was removed under reduced pressure, and water (500 mL) was added to the resulting suspension. The mixture was allowed to stand for 30 minutes. A solid was present and was isolated by filtration, washed with water and diethyl ether, and dried under vacuum for three hours to provide tert-butyl 2-[2-(methylthio)-1H-imidazo[4,5-c][1,5]naphthyridin-1-yl]ethylcarbamate as a white solid.

Part C

The general method of Part F of Example 22 was used to convert tert-butyl 2-[2-(methylthio)-1H-imidazo[4,5-c][1,5]naphthyridin-1-yl]ethylcarbamate (25 g, 70 mmol) to tert-butyl 2-[2-(methylsulfonyl)-1H-imidazo[4,5-c][1,5]naphthyridin-1-yl]ethylcarbamate, which was used in the next step without chromatographic purification.

Part D

Sodium ethoxide (4.2 g, 61 mmol) was added in one portion to a solution of tert-butyl 2-[2-(methylsulfonyl)-1H-imidazo[4,5-c][1,5]naphthyridin-1-yl]ethylcarbamate (20 g, 50 mmol) in ethanol (200 mL), and the resulting mixture was heated at reflux for four hours. Analysis by LC/MS indicated that no reaction had taken place, and additional sodium ethoxide (4.2 g, 61 mmol) was added. The mixture was heated at reflux overnight. Analysis by LC/MS indicated the presence of starting material, and a solution of sodium ethoxide (21% in ethanol, 150 mL) was added to the mixture. The reaction was heated at reflux for two hours and then concentrated under reduced pressure. Water was added, and the mixture was extracted with dichloromethane. A precipitate formed in the aqueous layer; the precipitate was isolated by filtration and washed with water to provide 7.3 g of 9,10-dihydro-8H-imidazo[1',2':1,2]imidazo[4,5-c][1,5]naphthyridine as a white solid.

Part E

Di-tert-butyl dicarbonate (1.3 g, 6.2 mmol) was added to a solution of 9,10-dihydro-8H-imidazo[1',2':1,2]imidazo[4,5-c][1,5]naphthyridine (1.3 g, 6.2 mmol) in dichloromethane (50 mL) and N,N-dimethylacetamide (15 mL), and the reaction was stirred for four hours. An analysis by LC/MS indicated that no reaction had taken place. Additional di-tert-butyl dicarbonate (1.3 g, 6.2 mmol) was added, and the reaction was stirred for four days. Water was added, and the mixture was extracted with dichloromethane. The combined organic fractions were concentrated under reduced pressure to provide 1.4 g of tert-butyl 9,10-dihydro-8H-imidazo[1',2':1,2]imidazo[4,5-c][1,5]naphthyridine-8-carboxylate containing some residual solvent.

Part F

A solution of tert-butyl 9,10-dihydro-8H-imidazo[1',2':1,2]imidazo[4,5-c][1,5]naphthyridine-8-carboxylate (1 g, 3 mmol) in dichloromethane (100 mL) was treated with MCPBA (1 g, 77% purity), and the reaction was stirred for two hours. Analysis by LC/MS indicated the presence of starting material, and additional MCPBA (1 g) was added. The next day, the reaction cooled in an ice bath and was treated with 100 mL of concentrated ammonium hydroxide. The reaction was stirred for several minutes, and then p-toluenesulfonyl chloride (730 mg, 3.8 mmol) was added. The reaction was stirred for several minutes, removed from the ice bath, and stirred for three hours at room temperature. Water was added, and the mixture was extracted with dichloromethane. The combined organic fractions were purified by automated flash chromatography on silica gel (eluting with a gradient of 2% ammonium hydroxide methanol as the polar component in dichloromethane). The resulting oil was triturated in diethyl ether to provide a yellow solid, which was isolated by filtration to provide 0.64 g of tert-butyl 6-amino-9,10-dihydro-8H-imidazo[1',2':1,2]imidazo[4,5-c][1,5]naphthyridine-8-carboxylate.

Part G

Hydrogen chloride (3.37 mL of a 4 N solution in 1,4-dioxane) was added to a mixture of tert-butyl 6-amino-9,10- dihydro-8H-imidazo[1',2':1,2]imidazo[4,5-c][1,5]naphthyridine-8-carboxylate (0.22 g, 0.67 mmol) in methanol (5 mL), and the resulting solution was stirred for three hours. Analysis by HPLC indicated the presence of starting material, and additional hydrogen chloride solution (3 mL) was added. The reaction was stirred at room temperature overnight and concentrated under reduced pressure. The resulting orange solid was triturated with hot acetonitrile and methanol, isolated by filtration, and washed with diethyl ether to provide 173 mg of 9,10-dihydro-8H-imidazo[1',2':1,2]imidazo[4,5-c][1,5]naphthyridin-6-amine as a pale orange solid.

Example 57

6-Amino-10,11-dihydro-9H-[1,3]oxazino[3',2':1,2]imidazo[4,5-c]quinolin-3-ol

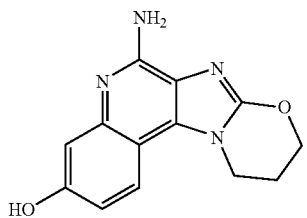

Part A

The general methods described in Parts A through G of Example 7 were followed beginning with 7-benzyloxy-4-chloro-3-nitroquinoline (International Publication Number WO 2005/020999, Example 1 Parts A through D) in lieu of 7-bromo-4-chloro-3-nitroquinoline to provide 3-(benzyloxy)-10,11-dihydro-9H-[1,3]oxazino[3',2':1,2]imidazo[4,5-c]quinoline. The following modifications were used. In Part A the reaction mixture was poured into water, and the product was isolated by filtration. In Part B, the reaction was complete after two hours, and a second addition of acetyl chloride was not carried out. In Part E, an aqueous work-up was carried out with dichloromethane and deionized water. In Part G, dichloromethane was added to the reaction mixture; the crude product was purified by automated flash chromatography on silica gel (ISCO Combiflash Separation System, Biotage column).

Part B

To a round-bottomed flask containing 3-(benzyloxy)-10,11-dihydro-9H-[1,3]oxazino[3',2':1,2]imidazo[4,5-c]quinoline (15.6 g, 47.1 mmol) was added chloroform (500 mL) followed by MCPBA (77% pure material, 26.4 g). The reaction was stirred at room temperature for 1.5 hours and then cooled in an ice bath. Concentrated ammonium hydroxide (230 mL) followed by p-toluenesulfonyl chloride (17.9 g, 93.9 mmol). The reaction was stirred in the ice bath for 20 minutes and then stirred overnight at room temperature. The reaction was diluted with additional chloroform (800 mL). A solid was present and was isolated by filtration to provide 7.0 g of a pink solid. The organic layer was washed with water (5×600 mL), dried over magnesium sulfate, filtered, and concentrated under reduced pressure to provide 12.39 g of 3-(benzyloxy)-10,11-dihydro-9H-[1,3]oxazino[3',2':1,2]imidazo[4,5-c]quinolin-6-amine as a brown solid.

Part C

Palladium on carbon (10%, 1.4 g) was added to a solution of 3-(benzyloxy)-10,11-dihydro-9H-[1,3]oxazino[3',2':1,2]imidazo[4,5-c]quinolin-6-amine (12.39 g, 35.8 mmol) in acetonitrile (125 mL) in a Parr bottle. The reaction was placed under hydrogen pressure overnight and then filtered through a layer of CELITE filter agent. The filter cake was washed with acetonitrile and methanol, and the filtrated was concentrated to provide 2.0 g of material. The filter cake was washed again with DMF and THF, and the filtrate was concentrated under reduced pressure to provide 2.6 g of material, which was added to a Parr bottle with methanol (60 mL) and 10% palladium on carbon (520 mg). The reaction was placed under hydrogen pressure for two days. An analysis by LC/MS indicated the reaction was incomplete, and additional 10% palladium on carbon was added. The reaction was placed under hydrogen pressure overnight and filtered through a layer of CELITE filter agent. The filter cake was washed with methanol and ethyl acetate to provide 190 mg of 6-amino-10,11-dihydro-9H-[1,3]oxazino[3',2':1,2]imidazo[4,5-c]quinolin-3-ol as a brown solid containing some impurities.

The methods described in Examples 30 through 54 can be used to couple 3-bromo-8,9,10,11-tetrahydropyrimido[1',2':1,2]imidazo[4,5-c]quinolin-6-amine trifluoroacetate with boronic acids to provide the compounds shown in Examples 58-82 below.

Examples 58-82

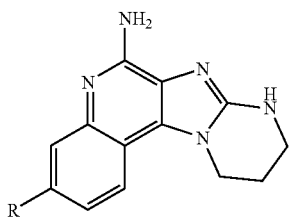

| Example | Reagent | R |
|---------|---------|---|
| 58 | Phenylboronic acid | ![phenyl] |

-continued

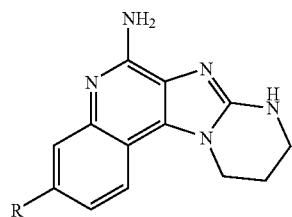

| Example | Reagent | R |
|---|---|---|
| 59 | Pyridine-3-boronic acid | 3-pyridyl |
| 60 | 2-Hydroxyphenylboronic acid | 2-hydroxyphenyl |
| 61 | 3-Hydroxyphenylboronic acid | 3-hydroxyphenyl |
| 62 | 2-Fluorophenylboronic acid | 2-fluorophenyl |
| 63 | 3-Fluorophenylboronic acid | 3-fluorophenyl |
| 64 | 4-Fluorophenylboronic acid | 4-fluorophenyl |
| 65 | 3-Cyanophenylboronic acid | 3-cyanophenyl |
| 66 | 2-Methoxyphenylboronic acid | 2-methoxyphenyl |
| 67 | 4-Methoxyphenylboronic acid | 4-methoxyphenyl |
| 68 | 3-Chlorophenylboronic acid | 3-chlorophenyl |

-continued

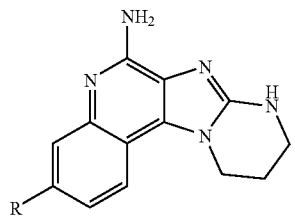

| Example | Reagent | R |
|---|---|---|
| 69 | 2-Chlorophenylboronic acid | 2-chlorophenyl |
| 70 | 4-Chlorophenylboronic acid | 4-chlorophenyl |
| 71 | (3-Aminocarbonylphenyl)boronic acid | 3-aminocarbonylphenyl |
| 72 | [3-(3-Hydroxypropyl)phenyl]boronic acid | 3-(3-hydroxypropyl)phenyl |
| 73 | 2,4-Dimethoxyphenylboronic acid | 2,4-dimethoxyphenyl |
| 74 | 2,6-Dimethoxyphenylboronic acid | 2,6-dimethoxyphenyl |
| 75 | 3,4-Dimethoxyphenylboronic acid | 3,4-dimethoxyphenyl |
| 76 | 4-Borono-DL-phenylalanine | 4-(2-amino-2-carboxyethyl)phenyl |

-continued
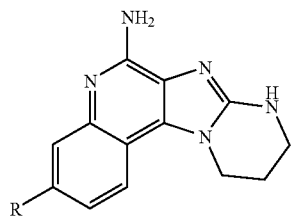
| Example | Reagent | R |
|---|---|---|
| 77 | 4-(Methylsulfonylamino)phenylboronic acid | 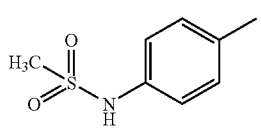 |
| 78 | 3-(Pyrrolidine-1-carbonyl)phenylboronic acid | 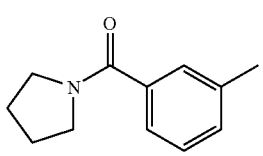 |
| 79 | 4-(Pyrrolidine-1-carbonyl)phenylboronic acid | 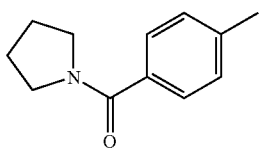 |
| 80 | 3-(Butylaminocarbonyl)phenylboronic acid | 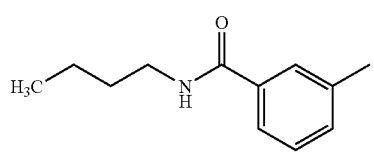 |
| 81 | 4-(Isobutylaminocarbonyl)phenylboronic acid | 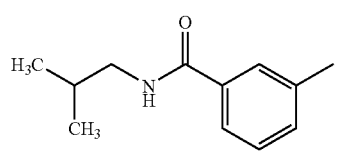 |
| 82 | 5-(tert-Butyldimethylsilanyloxymethyl)pyridine-3-boronic acid | 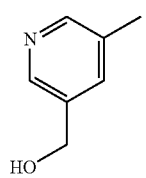 |

9,10-Dihydro-8H-imidazo[1',2':1,2]imidazo[4,5-c][1,5]naphthyridin-6-amine can be treated according to the method described in Examples 8 through 12 to provide the compounds shown in Examples 83 through 87 below.

Examples 83-87

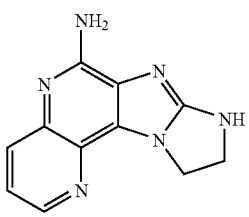

| Example | Reagent | R |
|---|---|---|
| 83 | Nicotinoyl chloride hydrochloride | |
| 84 | Benzenesulfonyl chloride | |
| 85 | Isopropyl isocyanate | |
| 86 | Phenyl isocyanate | |
| 87 | 1-Piperidinecarbonyl chloride | |

9,10-Dihydro-8H-imidazo[1',2':1,2]imidazo[4,5-c][1,5]naphthyridin-6-amine can be treated according to the method described in Examples 13 through 21 to provide the compounds shown in Examples 88 through 96 below.

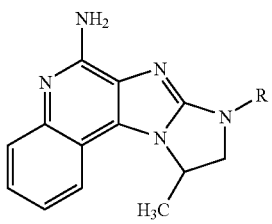

| Example | Reagent | R |
|---|---|---|
| 88 | Cyclopropanecarboxaldehyde | |
| 89 | Isobutyraldehyde | |
| 90 | Butyraldehyde | |
| 91 | Benzaldehyde | |
| 92 | Isonicotinaldehyde | |
| 93 | Nicotinaldehyde | |
| 94 | 1-Methyl-2-imidazolecarboxaldehyde | |
| 95 | 3-Methoxybenzaldehyde | |
| 96 | 3-Chlorobenzaldehyde | |

Compounds of the invention have been found to modulate cytokine biosynthesis by inducing the production of interferon α and/or tumor necrosis factor α in human cells when tested using the methods described below.

Cytokine Induction in Human Cells

An in vitro human blood cell system is used to assess cytokine induction. Activity is based on the measurement of interferon (α) and tumor necrosis factor (α) (IFN-α and TNF-α, respectively) secreted into culture media as described by Testerman et al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 µM. Controls include cell samples with media only, cell samples with DMSO only (no compound), and cell samples with reference compound.

Incubation

The solution of test compound is added at 60 µM to the first well containing RPMI complete and serial 3 fold dilutions are made in the wells. The PBMC suspension is then added to the wells in an equal volume, bringing the test compound concentrations to the desired range (usually 30-0.014 µM). The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype calorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (µmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Cytokine Induction in Human Cells

High Throughput Screen

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 µM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 µM) than the final tested concentration range.

Incubation

Compound solution is then added to the wells containing the PBMC suspension bringing the test compound concentrations to the desired range (usually 30-0.014 µM) and the DMSO concentration to 0.4%. The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30 to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α a capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemoluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the Formula I:

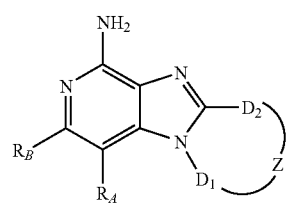

wherein:

D$_1$ is selected from the group consisting of —O—, —N(-Q$_1$-R$_4$)—, and —CH(R$_1$)—;

D$_2$ is selected from the group consisting of —O—, —N(-Q$_2$-R$_4$)—, and —CH$_2$—;

with the proviso that when D$_1$ is —CH(R$_1$)— then D$_2$ is —O— or —N(-Q$_2$-R$_4$)—;

Z is selected from the group consisting of —(CH$_2$)$_n$— and —(CH$_2$)$_c$—C(R$_{2a}$)(R$_2$)—(CH$_2$)$_d$—;

or -D$_1$-Z-D$_2$-, together with the imidazo ring atoms to which D$_1$ and D$_2$ are attached, forms a fused ring selected from the group consisting of

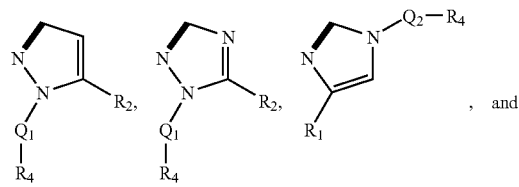

, and

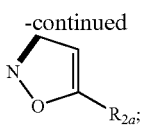

wherein the highlighted bond indicates the position where the ring is fused;

$R_1$ is selected from the group consisting of:
—$X_1$—$R_4$,
—$X_1$—Y—$R_4$,
—$X_1$—Y—X"—Y—$R_4$, and
—$X_1$—$R_5$;

$R_{2a}$ is selected from the group consisting of hydrogen and $C_{1-4}$ alkyl optionally substituted by hydroxy or halogen;

$R_2$ is selected from the group consisting of hydrogen, hydroxy, $C_{1-4}$ alkoxy, and $C_{1-4}$ alkyl optionally substituted by hydroxy or halogen;

c and d are independently 0, 1, or 2 with the proviso that c+d is ≦2;

with the proviso that when c and/or d is 0 then $R_2$ is other than hydroxy or $C_{1-4}$alkoxy;

n is 1, 2, or 3;

$R_A$ and $R_B$ are each independently selected from the group consisting of:
hydrogen,
halogen,
alkyl,
alkenyl,
alkoxy,
alkylthio, and
—$N(R_9)_2$;

or when taken together, $R_A$ and $R_B$ form a fused aryl or heteroaryl ring containing one heteroatom selected from the group consisting of N and S, wherein the fused aryl or heteroaryl ring is unsubstituted or substituted by one or more R groups, or substituted by one $R_3$ group, or substituted by one $R_3$ group and one R group;

or when taken together, $R_A$ and $R_B$ form a fused 5 to 7 membered saturated ring, optionally containing one heteroatom selected from the group consisting of N and S, and unsubstituted or substituted by one or more R groups;

R is selected from the group consisting of:
halogen,
hydroxy,
alkyl,
alkenyl,
haloalkyl,
alkoxy,
alkylthio, and
—$N(R_9)_2$;

$R_3$ is selected from the group consisting of:
—Z'—$R_4$,
—Z'—X"—$R_4$,
—Z'—X"—Y—$R_4$,
—Z'—X"—Y—X"—Y—$R_4$, and
—Z'—X"—$R_5$;

$X_1$ is selected from the group consisting of alkylene, alkenylene, and alkynylene, wherein the alkylene, alkenylene, and alkynylene are optionally interrupted by one or more —O— groups, and optionally substituted by a hydroxy or methoxy group;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
—O—,
—$S(O)_{0-2}$—,
—$S(O)_2$—$N(R_8)$—,
—$C(R_6)$—,
—$C(R_6)$—O—,
—O—$C(R_6)$—,
—O—C(O)—O—,
—$N(R_8)$-Q-,
—$C(R_6)$—$N(R_8)$—,
—O—$C(R_6)$—$N(R_8)$—,
—$C(R_6)$—$N(OR_9)$—,
—O—$N(R_8)$-Q-,
—O—N=$C(R_4)$—,
—C(=N—O—$R_8$)—,
—CH(—N(—O—$R_8$)-Q-$R_4$)—,

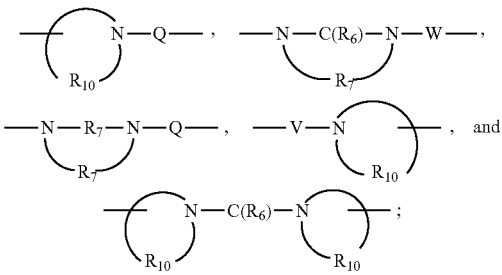

Z' is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo; with the proviso that when $R_4$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_4$ is heterocyclyl, then the one or more substituents may also be independently selected from the group consisting of arylalkylenyl, and aminocarbonyl;

$R_5$ is selected from the group consisting of:

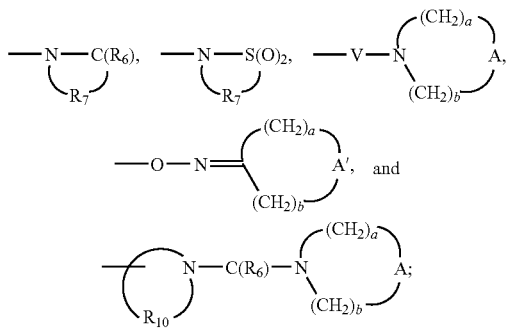

$R_6$ is selected from the group consisting of =O and =S;
$R_7$ is $C_{2-7}$ alkylene;
$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;
$R_9$ is selected from the group consisting of hydrogen and alkyl;
$R_{10}$ is $C_{3-8}$ alkylene;
A is selected from the group consisting of —CH$_2$—, —O—, —C(O)—, —S(O)$_{0-2}$—, and —N(-Q-R$_4$)—;
A' is selected from the group consisting of —O—, —S(O)$_{0-2}$—, —N(-Q-R$_4$)—, and —CH$_2$—;
Q, $Q_1$, and $Q_2$ are each independently selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—; with the proviso that when $Q_2$ is a bond then $R_4$ is hydrogen, $C_{1-3}$ alkyl, or pyridin-3-ylmethyl;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
with the proviso that $X_1$ can also be a bond when:
$R_4$ is bonded to $X_1$; or
Y is bonded to $X_1$ and Y is —C(R$_6$)—, —C(R$_6$)—O—, —C(R$_6$)—N(R$_8$)—, —C(R$_6$)—N(OR$_9$)—, —C(=N—O—R$_8$)—, —CH(—N(—O—R$_8$)-Q-R$_4$)—,

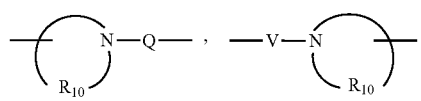

wherein V is —C(R$_6$)—, or

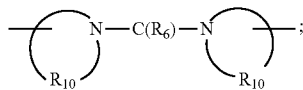

or
$R_5$ is bonded to $X_1$ and $R_5$ is

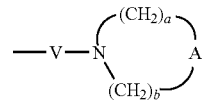

wherein V is —C(R$_6$)— or

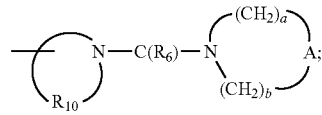

or a pharmaceutically acceptable salt thereof.

2. The compound or salt of claim 1 wherein $R_A$ is hydrogen, or alkyl, and $R_B$ is alkyl.

3. The compound or salt of claim 1 wherein R is halogen or hydroxy.

4. The compound or salt of claim 1 wherein $R_3$ is benzyloxy or —Z'—R$^4$.

5. The compound or salt of claim 1 wherein $R_3$ is —Z'—R$_4$ and wherein $R_4$ in —Z'—R$_4$ is selected from the group consisting of alkyl, alkenyl, alkynyl, aryl, heteroaryl, and heterocyclyl wherein alkyl and alkenyl are unsubstituted or substituted by one or more substituents independently selected from the group consisting of hydroxy, alkoxy, cyano, and aryl; wherein aryl and heteroaryl are unsubstituted or substituted by one or more substituents independently selected from the group consisting of alkyl, alkoxy, hydroxyalkyl, halogen, cyano, and dialkylamino; and wherein heterocyclyl is unsubstituted or substituted by one or more substituents independently selected from alkyl and oxo.

6. The compound or salt of claim 5 wherein Z' is a bond and $R_4$ is heterocyclyl which is selected from the group consisting of pyrrolidinyl, piperidinyl, oxazolidinyl, morpholinyl, and thiomorpholinyl, each of which is unsubstituted or substituted by one or more substituents independently selected from alkyl and oxo.

7. The compound or salt of claim 1 wherein $R_3$ is —Z'—X"—R$_4$ and wherein X" is $C_{1-3}$ alkylene or
$C_{1-3}$ alkenylene, and $R_4$ is heterocyclyl or heteroaryl wherein heterocyclyl is unsubstituted or substituted by one or more substituents independently selected from alkyl and oxo, and wherein heteroaryl is unsubstituted or substituted by one or more substituents independently selected from the group consisting of alkyl, alkoxy, halogen, cyano, and dialkylamino.

8. The compound or salt of claim 1 wherein $R_3$ is —Z'—X"—Y—R$_4$ and wherein X" is selected from the group consisting of $C_{1-3}$ alkylene, $C_{1-3}$ alkenylene, piperidin-1,4-diyl, and phenylene, Y is selected from the group of —C(R$_6$)—, —C(R$_6$)—O—, —C(R$_6$)—N(R$_8$)—, —N(R)-Q-, and —S(O)$_2$— wherein Q is selected from the group consisting of a bond, —C(O)—, —S(O)$_2$—, and —C(R$_6$)—N(R$_8$)—, $R_6$ is selected from the group consisting of =O and =S, and $R_8$ is selected from the group consisting of hydrogen, $C_{1-4}$ alkyl, and $C_{1-4}$ alkoxy$C_{1-4}$ alkylenyl; and $R_4$ is selected from the group consisting of hydrogen, alkyl, aryl, heteroaryl, and heterocyclyl; wherein alkyl is unsubstituted or substituted by one or more substituents independently selected from the group consisting of hydroxy, alkoxy, and aryl; wherein aryl is unsubstituted or substituted by one or more substituents independently selected from the group consisting of alkyl, halogen, cyano, dialkylamino, and alkoxy; and wherein heterocyclyl is unsubstituted or substituted by one or more substituents independently selected from the group consisting of alkyl and oxo.

9. The compound or salt of claim 8 wherein Y is —N($R_8$)-Q- or —C(O)— wherein $R_8$ is hydrogen, Q is —S(O)$_2$—, —C(O)—, or —C(O)—NH—, and $R_4$ is $C_{1-3}$ alkyl, pyridyl, or heterocyclyl.

10. The compound or salt of claim 1 wherein $R_3$ is —Z'—X"—$R_5$ and wherein X" is selected from the group consisting of $C_{1-3}$ alkylene and phenylene, and $R_5$ is selected from the group consisting of:

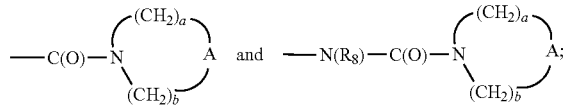

wherein A is —O—, —S—, or —SO$_2$—; $R_8$ is hydrogen or $C_{1-4}$ alkyl; and a and b are each independently an integer of 1 to 3.

11. The compound or salt of any one of claim 1 wherein $D_1$ is —CH($R_1$)—, and $D_2$ is —O— or —N(-Q$_2$-$R_4$)—; or $D_1$ is —O— or —N(-Q$_1$-$R_4$)—, and $D_2$ is —CH$_2$—.

12. The compound or salt of claim 1 wherein $R_1$ is —X$_1$—$R_4$ and wherein $R_4$ is selected from the group consisting of alkyl, aryl, arylalkylenyl, heteroaryl, and heteroarylalkylenyl, each of which is unsubstituted or substituted by one or more substituents.

13. The compound or salt of claim 1 wherein $R_1$ is selected from —X$_1$—Y—$R_4$, X$_1$—Y—X"—Y—$R_4$ or X$_1$—$R_5$.

14. The compound or salt of claim 13 wherein X$_1$ is $C_{1-4}$ alkylene and X" is arylene.

15. The compound or salt of claim 13 wherein Y is —C(O)—, —S(O)$_2$—, —N($R_8$)-Q-, or —C(O)—NH—.

16. The compound or salt of claim 15 wherein Q is —C(O)—, —S(O)$_2$, —S(O)$_2$—N($R_8$)—, or —C(O)—N($R_8$)—.

17. The compound or salt of claim 13 wherein Y is —S—, —S(O)$_2$—, or N($R_8$)-Q- wherein Q is a bond, —S(O)$_2$—, —C(O)—, —C(O)—O—, —C(O)—N($R_8$)—, —C(S)—N($R_8$)—, or —S(O)$_2$—N($R_s$)—; each $R_8$ is independently selected from the group consisting of hydrogen, $C_{1-4}$ alkyl, hydroxyC$_{1-4}$ alkyl, and $C_{1-4}$ alkoxyC$_{1-4}$ alkyl; and $R_4$ is hydrogen, alkyl, aryl, arylalkylenyl, heteroaryl, or heterocyclyl wherein alkyl, aryl, arylalkylenyl, heteroaryl, and heterocyclyl are unsubstituted or substituted by one or more substituents independently selected from the group consisting of hydroxy, halogen, alkoxy, alkyl, haloalkyl, and dialkylamino.

18. A pharmaceutical composition comprising a therapeutically effective amount of a compound or salt of claim 1 and a pharmaceutically acceptable carrier.

19. A method of inducing cytokine biosynthesis in an animal comprising administering an effective amount of a compound or salt of claim 1 or the pharmaceutical composition of claim 18 to the animal.

* * * * *